United States Patent
Swinnen et al.

(10) Patent No.: US 7,973,039 B2
(45) Date of Patent: Jul. 5, 2011

(54) SULFONYL AMINO CYCLIC DERIVATIVES AND USE THEREOF

(75) Inventors: Dominique Swinnen, Beaumont (FR); Agnes Bombrun, Chambesy (CH); Patrick Gerber, Etoy (CH); Catherine Jorand-Lebrun, Contamine-Sarzin (FR)

(73) Assignee: Merck Serono SA, Coinsins, Vaud (CH)

( * ) Notice: Subject to any disclaimer, the term of this patent is extended or adjusted under 35 U.S.C. 154(b) by 911 days.

(21) Appl. No.: 11/793,474

(22) PCT Filed: Dec. 19, 2005

(86) PCT No.: PCT/EP2005/056910
§ 371 (c)(1),
(2), (4) Date: Aug. 9, 2007

(87) PCT Pub. No.: WO2006/067114
PCT Pub. Date: Jun. 29, 2006

(65) Prior Publication Data
US 2008/0194520 A1    Aug. 14, 2008

Related U.S. Application Data

(60) Provisional application No. 60/638,257, filed on Dec. 22, 2004.

(30) Foreign Application Priority Data

Dec. 21, 2004 (EP) .................................. 04106814

(51) Int. Cl.
*A61P 29/00* (2006.01)
*A61P 37/00* (2006.01)
*A61K 31/495* (2006.01)
*A61K 31/496* (2006.01)
*C07D 211/96* (2006.01)
*C07D 213/42* (2006.01)
*C07D 213/74* (2006.01)
*C07D 243/08* (2006.01)
*C07D 295/22* (2006.01)
*C07D 317/58* (2006.01)
*C07F 7/08* (2006.01)

(52) U.S. Cl. ........... 514/235.8; 514/252.14; 514/253.01; 514/253.06; 514/254.01; 514/254.03; 514/254.11; 514/255.03; 544/121; 544/295; 544/360; 544/363; 544/367; 544/368; 544/372; 544/383

(58) Field of Classification Search .................. 514/235.8, 514/252.14, 253.01, 253.06, 254.01, 254.03, 514/254.11, 255.03; 544/121, 295, 360, 544/363, 367, 368, 372, 383
See application file for complete search history.

(56) References Cited

U.S. PATENT DOCUMENTS 5,540,938 A    7/1996    Masterson et al.

FOREIGN PATENT DOCUMENTS

| EP | 0 627 406 A1 | 12/1994 |
|---|---|---|
| WO | WO 98/48802 A1 | 11/1998 |
| WO | WO 99/55678 A1 | 11/1999 |
| WO | WO 99/67230 A1 | 12/1999 |
| WO | WO 00/12478 A1 | 3/2000 |
| WO | WO 01/45698 A1 | 6/2001 |
| WO | WO 01/47920 A1 | 7/2001 |
| WO | WO 01/83461 A1 | 11/2001 |
| WO | WO 02/028866 A2 | 4/2002 |
| WO | WO 02/080897 A1 | 10/2002 |
| WO | WO 03/068230 A1 | 8/2003 |
| WO | WO 03/070711 A1 | 8/2003 |
| WO | WO 2004/006926 A1 | 1/2004 |
| WO | WO 2004/028521 A2 | 4/2004 |
| WO | WO 2004/043965 A1 | 5/2004 |

OTHER PUBLICATIONS

International Search Report issued in International Application No. PCT/EP2005/056910, dated Apr. 5, 2006, 2 pages.
Written Opinion of the International Searching Authority issued International Application No. PCT/EP2005/056910, dated Apr. 5, 2006, 5 pages.
International Preliminary Report on Patentability issued in International Application No. PCT/EP2005/056910, dated Jun. 26, 2007, 6 pages.
Communication pursuant to Article 94(c) EPC, issued in European Application No. 05 826 371.6-2101, dated Mar. 5, 2009, 2 pages.
Basha, A., et al., "Addition of Organometallic Reagents to $N$-Glycosyl Nitrones. Enantioselective Syntheses of (+)-($R$)- and (−)-($S$)-Zileuton," *J. Org. Chem.*, 59(20): 6103-6106 (1994).
Belvisi, M., et al., "Review: The Role of Matrix Metalloproteinases (MMPs) in the Pathophysiology of Chronic Obstructive Pulmonary Disease (COPD): A Therapeutic Role for Inhibitors of MMPs?," *Inflammation Research*, 52: 95-100 (2003).
Bieber, L., et al., "Mild and Efficient Synthesis of Propargylamines by Copper-catalyzed Mannich Reaction," *Tetrahedron Letters*, 45(45): 8281-8283 (2004).
Bleicher, L., et al., "A Practical and Efficient Synthesis of the Selective Neuronal Acetylcholinegated Ion Channel Agonist ($S$)-(−)-5-Ethynyl-3-(1-methyl-2-pyrrolidinyl)pyridine Maleate (SIB-1508Y)," *J. Org. Chem.*, 63(4): 1109-1118 (1998).
Brenner, E., et al., "Nickel-catalysed Selective $N$-arylation or $N,N^1$-diarylation of Secondary Diamines," *Tetrahedron*, 58(34): 6913-6924 (2002).
Clark, I., et al., "Metalloproteinases: Their Role in Arthritis and Potential as Therapeutic Targets," *Expert Opin. Ther. Targets*, 7(1): 19-34 (2003).
Cossy, J., et al., "Synthesis of ML-3000, an Inhibitor of Cyclooxygenase and 5-Lipoxygenase," *J. Org. Chem.*, 62(23): 7900-7901 (1997).
Doherty, T., et al., "Therapeutic Developments in Matrix Metalloproteinase Inhibition," *Expert Opin. Ther. Patents*, 12(5): 665-707 (2002).

(Continued)

*Primary Examiner* — Brenda L Coleman
(74) *Attorney, Agent, or Firm* — Hamilton, Brook, Smith & Reynolds, P.C.

(57) ABSTRACT

The present invention is related to derivatives of Formula (I) and use thereof in particular for the treatment and/or prophylaxis of autoimmune disorders, inflammatory diseases, cardiovascular diseases, neurodegenerative diseases, cancer, respiratory diseases and fibrosis, including multiple sclerosis, arthritis, emphysema, chronic obstructive pulmonary disease, liver and pulmonary fibrosis.

24 Claims, No Drawings

OTHER PUBLICATIONS

Dupont, G., et al., "Étude de Quelques Monodérivés du Butyne-2 diol-1,4," *Bulletin de la Societe Chimique de France*, pp. 816-820 (1954).

Fingleton, B., et al., "Matrix Metalloproteinase Inhibitors for Cancer Therapy: The Current Situation and Future Prospects," *Expert Opin. Ther. Targets*, 7(3): 385-397 (2003).

Galis, Z., et al., "Matrix Metalloproteinases in Vascular Remodeling and Atherogenesis: The Good, the Bad, and the Ugly," *Circulation Research*, 90: 251-262 (2002).

Gómez, C., et al., "Functionalised Propargyllithium Reagents," *Tetrahedron*, 53(50), 17201-17210 (1997).

Henrotin, Y., et al., "The Inhibition of Metalloproteinases to Treat Osteoarthritis: Reality and New Perspectives," *Expert Opin. Ther. Patents*, 12(1): 29-43 (2002).

Hooper, N., et al., "Membrane Protein Secretases," *Biochem. J.*, 321: 265-279 (1997).

Horstmann, S., et al., "Profiles of Matrix Metalloproteinases, Their Inhibitors, and Laminin in Stroke Patients," *Stroke*, 34(9): 2165-2172 (2003).

Ingman, T., et al., "Matrix Metalloproteinases and Their Inhibitors in Gingival Crevicular Fluid and Saliva of Periodontitis Patients," *Journal of Clinical Periodontology*, 23: 1127-1132 (1996).

Kiritsy, J., et al., "Synthesis and Quantitative Structure-Activity Relationships of Some Antibacterial 3-Formylrifamycin SV N-(4-Substituted phenyl)piperazinoacethydrazones," *Journal of Medicinal Chemistry*, 21(12): 1301-1307 (1978).

Knight, C., et al., "A Novel Coumarin-labelled Peptide for Sensitive Continuous Assays of the Matrix Metalloproteinases," *Federation of European Biochemical Societies Letters*, 296(3): 263-266(1992).

Koller, M., et al., "278. Zum Mechanismus de α-Alkinon-Cyclisierung: Synthese und Thermolyse von 1-(1-Methylcyclopentyl)[3-$^{13}$C]prop-2-inon," *Helvetica Chimica Acta*, 66(8): 2760-2768 (1983).

Krishna, G., et al., "New Therapies for Chronic Obstructive Pulmonary Disease," *Expert Opin. Investig. Drugs*, 13(3): 255-267 (2004).

Leppert, D., et al., "Matrix Metalloproteinases: Multifunctional Effectors of Inflammation in Multiple Sclerosis and Bacterial Meningitis," *Brain Research Reviews*, 36: 249-257 (2001).

Liu, M., et al., "Association of Increased Expression of Macrophage Elastase (Matrix Metalloproteinases 12) With Rheumatoid Arthritis," *Arthritis & Rheumatism*, 50(10): 3112-3117 (2004).

Makrakis, E., et al., "Matrix Metalloproteinase-9 and Tissue Inhibitor of Metalloproteinase-1 in Plasma/serum and Urine of Women During Term and Threatened Preterm Labor: A Clinical Approach," *The Journal of Maternal-Fetal and Neonatal Medicine*, 14(3): 170-176 (2003).

Nugent, W., et al., "Cyclization of Diacetylenes to E,E Exocyclic Dienes. Complementary Procedures Based on Titanium and Zirconium Reagents," *J. Am. Chem. Soc.*, 109(9): 2788-2796 (1987).

Opdenakker, G., et al., "Functional Roles and Therapeutic Targeting of Gelatinase B and Chemokines in Multiple Sclerosis," *The Lancet Neurology*, 2: 747-756 (2003).

Peterson, J., et al., "Matrix Metalloproteinasse Inhibitor Development and the Remodeling of Drug Discovery," *Heart Failure Reviews*, 9: 63-79 (2004).

Skiles, J., et al., "The Design, Structure, and Therapeutic Application of Matrix Metalloproteinase Inhibitors," *Current Medicinal Chemistry*, 8(4): 425-474 (2001).

Skotnicki, J., et al., "Design Strategies for the Identification of MMP-13 and TACE Inhibitors," *Current Opinion in Drug Discovery & Development*, 6(5): 742-759 (2003).

Swanson, D., et al., "Identification and Biological Evaluation of 4-(3-Trifluoromethylpyridin-2-yl)piperazine-1-carboxylic acid (5-Trifluoromethylpyridin-2-61)amide, a High Affinity TRPV1 (VR1) Vanilloid Receptor Antagonist," *J. Med. Chem.*, 48(6): 1857-1872 (2005).

Visse, R., et al., "Matrix Metalloproteinases and Tissue Inhibitors of Metalloproteinases: Structure, Function, and Biochemistry," *Circulation Research*, 92: 827-839 (2003).

Vos, C., et al., "Matrix Metalloproteinase-12 is Expressed in Phagocytotic Macrophages in Active Multiple Sclerosis Lesions," *Journal of Neuroimmunology*, 138: 106-114 (2003).

Wada, C., et al., "Phenoxyphenyl Sulfone N-Formylhydroxylamines (Retrohydroxamates) as Potent, Selective, Orally Bioavailable Matrix Metalloproteinase Inhibitors," *J. Med. Chem.*, 45(1): 219-232 (2002).

Wustrow, D., et al., "Coupling of Arylboronic Acids With a Partially Reduced Pyridine Derivative," *Synthesis*, pp. 993-995 (Nov. 1991).

Zhao, S., et al., "Synthesis of Arylpiperazines via Palladium-catalyzed Aromatic Amination Reaction With Unprotected Piperazines," *Tetrahedron Letters*, 37(26): 4463-4466 (1996).

SULFONYL AMINO CYCLIC DERIVATIVES AND USE THEREOF

RELATED APPLICATIONS

This application is the U.S. National Stage of International Application No. PCT/EP2005/056910, filed Dec. 19, 2005, published in English, and claims priority under 35 U.S.C. §119 or 365 to European Application No. 04106814.9, filed Dec. 21, 2004, and to U.S. Provisional Application 60/638,257, filed Dec. 22, 2004.

FIELD OF THE INVENTION

The present invention is related to sulfonyl amino cyclic derivatives of Formula (I), pharmaceutical composition thereof, their use for the treatment and/or prophylaxis of autoimmune disorders and/or inflammatory diseases, cardiovascular diseases, neurodegenerative diseases, cancer, respiratory diseases and fibrosis and methods of preparation thereof. Specifically, the present invention is related to sulfonyl amino cyclic derivatives for the modulation, notably the inhibition of the activity or function of matrix metalloproteinases, such as gelatinases and metalloelastases.

BACKGROUND OF THE INVENTION

Metalloproteinases are a superfamily of proteinases (enzymes) named for their dependence on a metal ion (zinc) in the active site.

The matrix metalloproteinases (MMPs) form a metalloproteinase sub-family having as one of major biological function to catalyse the breakdown of connective tissue or extracellular matrix through their ability to hydrolyse various components of the tissue or matrix, such as collagens, gelatins, proteoglycans, fibronectins and elastin.

The matrix metalloproteinase family is further divided according to their function and substrates (Visse al., 2003, *Circ. Res.*, 92, 827-839) and comprises collagenases (MMP-1, MMP-8, MMP-13 and MMP-18), gelatinases (MMP-2 and MMP-9), stromelysins (MMP-3, MMP-10 and MMP-11), membrane-type MMPs (MT-MMP-1 to MT-MMP-6 and MMP-14, MMP-15, MMP-16, MMP-17, MMP-24 and MMP-25), matrilysins (MMP-7 and MMP-26) and other unclassified MMPs such as metalloelastase (MMP-12), enamelysin (MMP-20), epilysin (MMP-28), MMP-19, MMP-22 and MMP-23.

Apart from their role in degrading connective tissue, MMPs are involved in the biosynthesis of TNF-alpha and in the post-translational proteolysis processing, or shedding of biologically important membrane proteins (Hooper et al., 1997, *Biochem J.*, 321, 265-279). MMPs for example contribute to the local growth and spread of malignant lesions and therefore have been a target for anti-tumor drug development (Fingleton et al., 2003, *Expert Opin. Ther. Targets*, 7(3): 385-397). Disorders such as inflammatory disorders like arthritis (Clark et al., 2003, *Expert. Opin. Ther Targets*, 7(1): 19-34), respiratory disorders such as emphysema, atherosclerosis (Galis et al., 2002, *Circ. Res.*, 90:251-262), neurological disorders such as degenerative nervous system diseases, multiple sclerosis (Leppert et al., 2001, *Brain Res. Rev.*, 36:249-257), periodontitis (Ingman et al., 1996, *J. clin. Periodontal.*, 23:127-1132), pre-term labor (Makrakis et al., 2003, *J. Matern Fetal & Neonatal Medicine*, 14(3): 170-6) and wound healing have been demonstrated to be associated with MMPs expression and/or activity.

A wide variety of matrix metalloproteinase inhibitors (MMPIs) has been developed (Skiles et al., 2001, *Current Medicinal Chemistry*, 8, 425-474; Peterson, 2004, *Heart Failure Reviews*, 9, 63-79; Henrotin et al., 2002, *Expert Opin.* *Ther. Patents*, 12(1): 29-43). However, many MMPIs exhibit a muscoskeletal syndrome (tendonitis, fibroplasias, mylasia, arthralasia) as a dose-limiting side effect. It has been proposed that inhibition of MMP-1 or MMP-14 may be responsible for these effects.

Therefore, there is an increasing need to develop matrix metalloproteinase inhibitors with a well-defined specificity profile.

Specific inhibitors, especially towards MMP-1, have been reported, including MMP-13 inhibitors (Stotnicki et al., 2003, *Current Opinion in Drug Discovery and Development*, 6(5): 742-759), MMP-12 inhibitors (WO 01/83461; WO03/070711), MMP-2 and MMP-9 inhibitors (Wada et al., 2002, *J. Med. Chem.* 45, 219-232).

The high relevance of the metalloproteinase pathway in some widely spread diseases stresses the need to develop inhibitors, including selective inhibitors of MMPs, such as gelatinases like MMP-2 and/or MMP-9 and/or MMP-12.

SUMMARY OF THE INVENTION

It is an object of the invention to provide substances which are suitable for the treatment and/or prevention of disorders related to autoimmune disorders and/or inflammatory diseases, cardiovascular diseases, neurodegenerative diseases, stroke, cancer, respiratory diseases, preterm labor and fibrosis.

It is further an object of the present invention to provide substances which are suitable for the treatment and/or prevention of multiple sclerosis, rheumatoid arthritis, emphysema, chronic obstructive pulmonary disease and fibrosis.

It is notably an object of the present invention to provide chemical compounds which are able to modulate, especially inhibit the activity or function of matrix metalloproteinases, such as gelatinases and/or elastase in mammals, especially in humans.

It is furthermore an object of the present invention to provide a new category of pharmaceutical formulations for the treatment of and/or diseases mediated selected from autoimmune disorders, inflammatory diseases, cardiovascular diseases, neurodegenerative diseases, stroke, cancer, respiratory diseases, preterm labor and fibrosis.

It is furthermore an object of the present invention to provide processes for making chemical compounds according to the invention.

It is furthermore an object of the present invention to provide new compounds useful in such processes for making chemical compounds according to the invention.

It is finally an object of the present invention to provide a method for the treatment and/or prevention of disorders selected from autoimmune disorders, inflammatory diseases, cardiovascular diseases, neurodegenerative diseases, stroke, cancer, respiratory diseases, preterm labor and fibrosis.

In a first aspect, the invention provides sulfonyl amino cyclic derivatives of Formula (I):

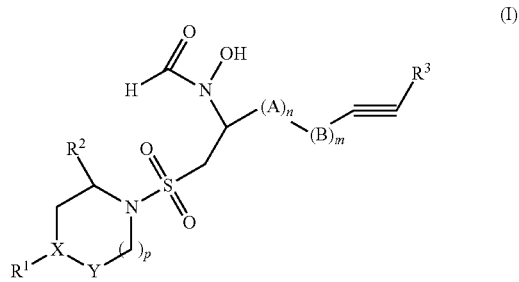

wherein A, B, $R^1$, $R^2$, $R^3$, X, Y, m, n and p are defined in the detailed description.

In a second aspect, the invention provides a sulfonyl amino cyclic derivative according to Formula (I) for use as a medicament.

In a third aspect, the invention provides a use of a sulfonyl amino cyclic derivative according to Formula (I) for the preparation of a pharmaceutical composition for the treatment of a disorder selected from autoimmune disorders, inflammatory diseases, cardiovascular diseases, neurodegenerative diseases, stroke, cancer, respiratory diseases, preterm labor and fibrosis.

In a fourth aspect, the invention provides a pharmaceutical composition comprising at least one sulfonyl amino cyclic derivative according to Formula (I) and a pharmaceutically acceptable carrier, diluent or excipient thereof.

In a fifth aspect, the invention provides a method of treatment comprising the administration of a sulfonyl amino cyclic derivative according to Formula (I) in a patient in need thereof.

In a sixth aspect, the invention provides methods of synthesis of a sulfonyl amino cyclic derivative according to Formula (I).

In a seventh aspect, the invention provides a compound according to Formula (II):

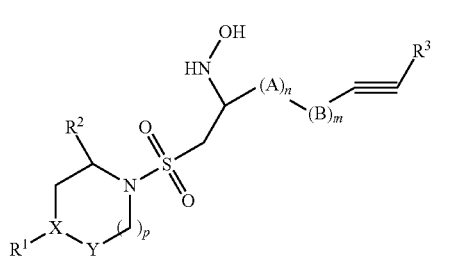

(II)

wherein A, B, $R^1$, $R^2$, $R^3$, X, Y, m, n and p are defined in the detailed description.

In an eighth aspect, the invention provides a compound according to Formula (III):

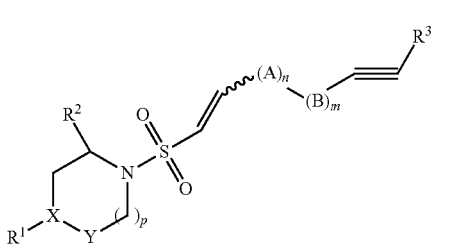

(III)

wherein A, B, $R^1$, $R^2$, $R^3$, X, Y, m, n and p are in the detailed description.

In a ninth aspect, the invention provides a compound according to Formula (VIII):

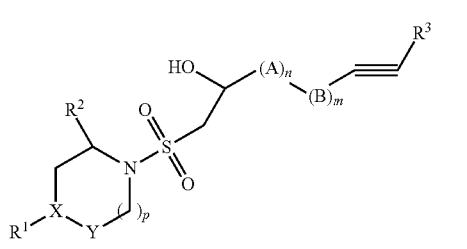

(VIII)

wherein A, B, $R^1$, $R^2$, $R^3$, X, Y, m, n and p in the detailed description.

In a tenth aspect, the invention provides a compound according to Formula (VII):

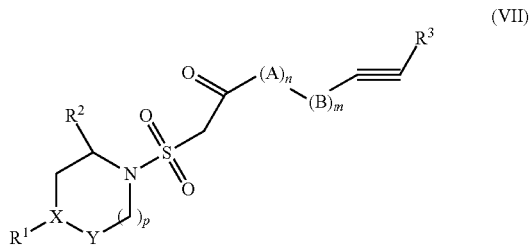

(VII)

wherein A, B, $R^1$, $R^2$, $R^3$, X, Y, m, n and p are in the detailed description.

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

The term "MMPs" refers to "matrix metalloproteinases". For recent reviews of MMPs, see Visse et al., 2003 above; Fingleton et al., 2003, above; Clark et al., 2003, above and Doherty et al., 2002, *Expert Opinion Therapeutic Patents* 12(5): 665-707.

Illustrative but not limiting examples of such MMPs are:

Collagenases: usually associated with diseases linked to breakdown of collagen-based tissue e.g. rheumatoid arthritis and osteoarthritis:

MMP-1 (also known as collagenase 1, or fibroblast collagenase), substrates: collagen I, collagen II, collagen III, gelatin, proteoglycans. Over-expression of this enzyme is believed to be associated with emphysema, with hyperkeratosis and atherosclerosis, overexpressed alone in papillary carcinoma.

MMP-8 (also known as collagenase 2, or neutrophil collagenase), substrates: collagen I, collagen II, collagen III, collagen V, collagen VII, collagen IX, gelatin over-expression of which can lead to non-healing chronic ulcers.

MMP-13 (also known as collagenase 3), substrates: collagen I, collagen II, collagen III, collagen IV, collagen IX, collagen X, collagen XIV, fibronectin, gelatin, recently identified as being over-expressed alone in breast carcinoma and involved in rheumatoid arthritis.

Stromelysins:

MMP-3 (also known as stromelysin 1), substrates: collagen III, collagen IV, collagen V, collagen IX, collagen X, larninin, nidogen, over-expression believed to be involved in atherosclerosis, aneurysm and restenosis.

Gelatinases—inhibition believed to exert a favorable effect on cancer, in particular invasion and metastasis.

MMP-2 (also known as gelatinase A, 72 kDa gelatinase, basement membrane collagenase, or proteoglycanase), substrates: Collagen I, Collagen II, Collagen IV, Collagen V, Collagen VII, Collagen X, Collagen XI, collagen XIV, elastin, fibronectin, gelatin, nidogen, believed to be associated with tumor progression through specificity for type IV Collagen (high expression observed in solid tumors and believed to be associated with their ability to grow, invade, develop new blood vessels and metastasize) and to be involved in acute lung inflammation and in respiratory distress syndrome (Krishna et al., 2004, *Expert Opin. Invest. Drugs*, 13(3): 255-267).

MMP-9 (also known as gelatinase B, or 92 kDa gelatinase), substrates: Collagen I, Collagen III, Collagen IV, Collagen V, Collagen VII, collagen X, Collagen XIV, elastin, fibronectin, gelatin, nidogen. The above enzyme is believed to be associated with tumor progression through specificity for type IV Collagen, to be released by eosinophils in response to exogenous factors such as air pollutants, allergens and viruses, to be involved in the inflammatory response in multiple sclerosis (Opdenakker et al., 2003, *The Lancet Neurology*, 2, 747-756) and asthma and to be involved in acute lung inflammation, respiratory distress syndrome, chronic obstructive pulmonary disorder (COPD) and/or asthma (Krishna et al., 2004, above). MMP-9 is also thought to be involved in stroke (Horstmann et al., 2003, *Stroke* 34(9), 2165-70).

Unclassified MMPs:

MMP-12 (also known as metalloelastase, human macrophage elastase, or HME), substrates: fibronectin, larninin. MMP-12 is believed to play a role in tumour growth inhibition and regulation of inflammation such as multiple sclerosis (Vos et al., 2003, *Journal of Neuroimmunology*, 138, 106-114) and rheumatoid arthritis (Liu et al., 2004, *Arthritis & Rheumatism*, 50(10), 3112-3117). MMP-12 is also believed to play a pathological role in emphysema, COPD (Belvisi et al., 2003, *Inflamm. Res.* 52; 95-100), in atherosclerosis, aneurysm and restenosis.

The expression "MMP-associated disorder" refers to a disorder which is treatable according to the invention and that encompasses all disorders in which the expression and/or activity of at least one MMP needs to be decreased irrespective of the cause of such disorders. Such disorders include, for example, those caused by inappropriate extracellular matrix (ECM) degradation.

Illustrative but not limiting examples of such MMP-associated disorders are:

Cancer such as breast cancer and solid tumors; inflammatory disorders such as for example inflammatory bowel diseases and neuroinflammation such as multiple sclerosis; lung diseases such as chronic obstructive pulmonary disorder (COPD), emphysema, asthma, acute lung injury, and acute respiratory distress syndrome; pre-term labor; dental diseases such as periodontal disease and gingivitis; joint and bone diseases such as osteoarthritis and rheumatoid arthritis; liver diseases such as liver fibrosis, cirrhosis and chronic liver disease; fibrotic diseases such as pulmonary fibrosis, pancreatitis, lupus, glomerulosclerosis, systemic sclerosis skin fibrosis, post-radiation fibrosis and cystic fibrosis; vascular pathologies such as aortic aneurysm, atherosclerosis, hypertension, cardiomyopathy and myocardial infarction; restenosis; opthalmological disorders such as diabetic retinopathy, dry eye syndrome, macula degeneration and corneal ulceration and degenerative diseases of the central nervous system such as amyotrophic lateral sclerosis.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, pentyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including 3-phenyl propyl, benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, 1,3 benzodioxol-5-yl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to heteroaryl groups having a $C_1$-$C_6$-alkyl substituent, including methyl furyl and the like.

"Heteroaryl $C_1$-$C_6$-alkyl" refers to $C_1$-$C_6$-alkyl groups having a heteroaryl substituent, including furyl methyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=CH$_2$), n-2-propenyl (allyl, —CH$_2$CH=CH$_2$) and the like.

"$C_2$-$C_6$-alkenyl aryl" refers to an aryl groups having a $C_2$-$C_6$-alkenyl substituent, including vinyl phenyl and the like.

"Aryl $C_2$-$C_6$-alkenyl" refers to a $C_2$-$C_6$-alkenyl groups having an aryl substituent, including phenyl vinyl and the like.

"$C_2$-$C_6$-alkenyl heteroaryl" refers to heteroaryl groups having a $C_2$-$C_6$-alkenyl substituent, including vinyl pyridinyl and the like.

"Heteroaryl $C_2$-$C_6$-alkenyl" refers to $C_2$-$C_6$-alkenyl groups having a Heteroaryl substituent, including pyridinyl vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"$C_1$-$C_6$-alkyl cycloalkyl" refers to $C_3$-$C_8$-cycloalkyl groups having a $C_1$-$C_6$-alkyl substituent, including methyl cyclopentyl and the like.

"Cycloalkyl $C_1$-$C_6$-alkyl" refers to $C_1$-$C_6$-alkyl groups having a $C_3$-$C_8$-cycloalkyl substituent, including 3-cyclopentyl propyl and the like.

"$C_1$-$C_6$-alkyl heterocycloalkyl" refers to heterocycloalkyl groups having a $C_1$-$C_6$-alkyl substituent, including 1-methylpiperazine and the like.

"Heterocycloalkyl $C_1$-$C_6$-alkyl" refers to $C_1$-$C_6$-alkyl groups having a heterocycloalkyl substituent, including 4-methyl piperidyl and the like.

"Carboxy" refers to the group —C(O)OH.

"Carboxy $C_1$-$C_6$-alkyl" refers to $C_1$-$C_6$-alkyl groups having an carboxy substituent, including 2-carboxyethyl and the like.

"Acyl" refers to the group —C(O)R where R includes "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyl $C_1$-$C_6$-alkyl" to $C_1$-$C_6$-alkyl groups having an acyl substituent, including acetyl, 2-acetylethyl and the like.

"Acyl aryl" refers to aryl groups having an acyl substituent, including 2-acetylphenyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acyloxy $C_1$-$C_6$-alkyl" refers to $C_1$-$C_6$-alkyl groups having an acyloxy substituent, including propionic acid ethyl ester and the like.

"Alkoxy" refers to the group —O—R where R includes "$C_1$-$C_6$-alkyl" or "aryl" or "heteroaryl" or "aryl $C_1$-$C_6$-alkyl" or "heteroaryl $C_1$-$C_6$-alkyl". Preferred alkoxy groups include for example, methoxy, ethoxy, phenoxy and the like.

"Alkoxy $C_1$-$C_6$-alkyl" refers to alkoxy groups having an $C_1$-$C_6$-alkyl substituent, including methoxy, methoxyethyl and the like.

"Alkoxycarbonyl" refers to the group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl" or "heteroalkyl".

"Alkoxycarbonyl $C_1$-$C_6$-alkyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Aminocarbonyl $C_1$-$C_6$-alkyl" refers to $C_1$-$C_6$-alkyl groups having an aminocarbonyl substituent, including 2-(dimethylaminocarbonyl)ethyl, N-ethyl acetamide, N,N-Diethyl acetamide and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acylamino $C_1$-$C_6$-alkyl" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl", and where R' and R", together with the nitrogen atom to which they are attached, can optionally form a 3-8-membered heterocycloalkyl ring.

"Ureido $C_1$-$C_6$-alkyl" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Amino $C_1$-$C_6$-alkyl" refers to $C_1$-$C_5$-alkyl groups having an amino substituent, including 2-(1-pyrrolidinyl)ethyl, diethylamino methyl and the like.

"Ammonium" refers to a positively charged group —N$^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Ammonium $C_1$-$C_6$-alkyl" refers to $C_1$-$C_6$-alkyl groups having an ammonium substituent, including 1-ethylpyrrolidinium and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy $C_1$-$C_6$-alkyl" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyl $C_1$-$C_6$-alkyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl", substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfinyl $C_1$-$C_6$-alkyl" refers to $C_1$-$C_6$-alkyl groups having a sulfinyl substituent, including 2-(methylsulfinyl)ethyl and the like.

"Sulfanyl" refers to groups—S—R where R includes H, "$C_1$-$C_6$-alkyl", "$C_1$-$C_6$-alkyl" substituted with halogens, e.g., a—SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "alkynylheteroaryl $C_2$-$C_6$,", "cycloalkyl $C_1$-$C_6$-alkyl", "heterocycloalkyl $C_1$-$C_6$-alkyl". Preferred sulfanyl groups include methylsulfanyl, ethylsulfanyl, and the like.

"Sulfanyl $C_1$-$C_6$-alkyl" refers to $C_1$-$C_5$-alkyl groups having a sulfanyl substituent, including 2-(ethylsulfanyl)ethyl and the like.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonylamino $C_1$-$C_6$-alkyl" refers to $C_1$-$C_6$-alkyl groups having a sulfonylamino substituent, including 2-(ethylsulfonylamino)ethyl and the like.

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$ alkynyl", "cycloalkyl $C_1$-$C_6$-alkyl", "heterocycloalkyl $C_1$-$C_6$-alkyl".

"Aminosulfonyl $C_1$-$C_6$-alkyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "aryl $C_1$-$C_6$-alkyl", "heteroaryl $C_1$-$C_6$-alkyl", "cycloalkyl $C_1$-$C_6$-alkyl", "heterocycloalkyl $C_1$-$C_6$-alkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N, N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group.

"Enantiomeric excess" (ee) refers to the products that are obtained and can be separated by an asymmetric synthesis, i.e. a synthesis involving non-racemic starting materials and/or reagents or a synthesis comprising at least one enantioselective step, whereby a surplus of one enantiomer in the order of at least about 52% ee is yielded.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as Rebif® (Serono), Avonex® (Biogen) or Betaferon® (Schering).

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably, IFN-beta is intended to mean recombinant Interferon beta-1a.

IFN-β suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogs and active fragments thereof.

Rebif® (recombinant interferon-β) is the latest development in interferon therapy for multiple sclerosis (MS) and represents a significant advance in treatment. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

The dosing of IFN-β in the treatment of relapsing-remitting MS according to the invention depends on the type of IFN-β used.

In accordance with the present invention, where IFN is recombinant IFN-β1b produced in E. Coli, commercially available under the trademark Betaseron®, it may preferably be administered sub-cutaneously every second day at a dosage of about of 250 to 300 μg or 8 MIU to 9.6 MIU per person.

In accordance with the present invention, where IFN is recombinant IFN-β1a, produced in Chinese Hamster Ovary cells (CHO cells), commercially available under the trademark Avonex®, it may preferably be administered intramuscularly once a week at a dosage of about of 30 μg to 33 μg or 6 MIU to 6.6 MIU per person.

In accordance with the present invention, when IFN is recombinant IFN-β1a, produced in Chinese Hamster Ovary cells (CHO cells), commercially available under the trademark Rebif®, it may preferably be administered sub-cutaneously three times a week (TIW) at a dosage of 22 to 44 μg or 6 MIU to 12 MIU per person.

Compounds according to the present invention also comprise pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

It has now been found that compounds of the present invention are modulators of the matrix metalloproteinases such as gelatinases and elastase, including MMP-2 and/or MMP-9, preferably MMP-12. When the matrix metalloproteinase enzyme is inhibited by the compounds of the present invention, the inhibited MMP(s) is (are) unable to exert its enzymatic, biological and/or pharmacological effects. The compounds of the present invention are therefore useful in the treatment and prevention of autoimmune disorders and/or inflammatory diseases, cardiovascular diseases, neurodegenerative diseases, stroke, cancer, pre-term labor, respiratory diseases and fibrosis.

In one embodiment, the invention provides derivatives of Formula (I):

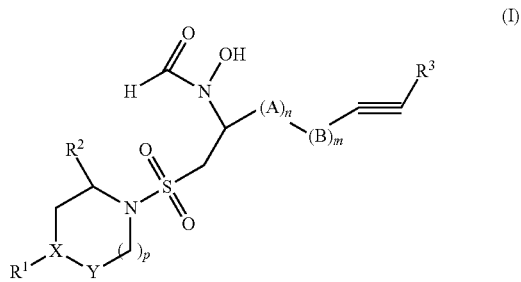

wherein:
A is —$CR^4R^5$, including gem-dimethyl;
B is —$CR^4R^{5'}$, including methylenyl;
$R^1$ is selected from optionally substituted aryl, including optionally substituted phenyl such as phenyl, halogeno phenyl (e.g. 4-fluorophenyl, 2-fluorophenyl, 4-chlorophenyl, 3-chloro phenyl), alkoxyphenyl (e.g. 4-((phenylmethyl)oxy) phenyl, 4-methoxyphenyl, 2-methoxy phenyl, 3-methoxyphenyl, 4-(phenyloxy)phenyl, 4-(ethyloxy)phenyl, 3,4-dimethoxyphenyl), optionally substituted $C_1$-$C_6$ alkyl phenyl (e.g. 4-trifluoromethylphenyl, 4-methylphenyl) and optionally substituted bi-phenyl (e.g. 4-biphenyl-4-yl); optionally substituted heteroaryl, including optionally substituted pyridinyl such as pyridinyl (e.g. pyridin-2-yl), optionally substituted $C_1$-$C_6$-alkyl pyridinyl (e.g. 5-trifluoromethylpyridin-2-yl) and halogeno pyridinyl (e.g. 5-chloropyridin-2-yl, 5-bromopyridin-2-yl), optionally substituted pyrimidinyl (e.g. pyrimidin-2-yl), optionally substituted benzodioxol (e.g. 1,3-benzodioxol-5-yl); optionally substituted $C_3$-$C_8$-cycloalkyl and optionally substituted heterocycloalkyl;
$R^2$ is selected from H; optionally substituted $C_1$-$C_6$-alkyl, including methyl; optionally substituted $C_2$-$C_6$-alkenyl and optionally substituted $C_2$-$C_6$-alkynyl;
$R^3$ is selected from H; —Si($C_1$-$C_6$-alkyl)$_3$; optionally substituted amino $C_1$-$C_6$-alkyl, including 4-diethylaminomethyl; optionally substituted $C_1$-$C_6$-alkyl, including ethyl, propyl, butyl and pentyl; optionally substituted aryl, including substituted phenyl such as phenyl, halogeno phenyl(4-fluorophenyl, 3-fluorophenyl, 2-fluorophenyl), alkoxyphenyl (e.g. 3-methoxyphenyl), optionally substituted heteroaryl phenyl such as oxadiazol phenyl (e.g. 1,2,4-oxadiazol-3-yl phenyl); optionally substituted heteroaryl, including optionally substituted pyridinyl such as pyridinyl (e.g. pyridin-3-yl), optionally substituted benzodioxol (e.g. 1,3-benzodioxol-5-yl), optionally substituted quinolinyl (e.g. 3-quinolin-3-yl); optionally substituted aryl $C_1$-$C_6$-alkyl, including aryl methyl such as phenyl methyl; optionally substituted heteroaryl $C_1$-$C_6$-alkyl; optionally substituted $C_3$-$C_8$-cycloalkyl $C_1$-$C_6$-alkyl; optionally substituted heterocycloalkyl $C_1$-$C_6$-alkyl, including morpholinomethyl (e.g. morpholino-4-ylmethyl) and pyrrolidinylmethyl (e.g. pyrrolidin-1-ylmethyl); optionally substituted $C_3$-$C_8$-cycloalkyl and optionally substituted heterocycloalkyl;
$R^4$, $R^5$, $R^{4'}$ and $R^{5'}$ are independently selected from H; halogen; optionally substituted $C_1$-$C_6$-alkyl, including methyl; optionally substituted $C_2$-$C_6$-alkenyl and optionally substituted $C_2$-$C_6$-alkynyl;
X is selected from C, CH and N;
Y is selected from CH and $CH_2$; and the group —X . . . Y— is selected from —C=CH—, —CH—$CH_2$—, and —N—$CH_2$—;
m is selected from 0, 1 and 2; n is selected from 0 and 1;
p is selected from 1 and 2;
as well as its optically active forms as enantiomers, diastereomers and its racemate forms, as well as pharmaceutically acceptable salts thereof.

In a preferred embodiment, the invention provides derivatives of Formula (I) wherein $R^1$ is optionally substituted aryl, including optionally substituted phenyl such as 4-fluororophenyl, 4-benzyloxyphenyl, 4-methoxyphenyl, 2-fluorophenyl, 4-chlorophenyl, 3-chloro phenyl, 4-((phenylmethyl)oxy)phenyl, 4-methoxyphenyl, 2-methoxy phenyl, 3-methoxyphenyl, 4-(phenyloxy)phenyl, 4-(ethyloxy)phenyl, 3,4-dimethoxyphenyl, 4-trifluoromethylphenyl, 4-methylphenyl and 4-biphenyl-4-yl.

In another preferred embodiment, the invention provides derivatives of Formula (I) wherein $R^1$ is optionally substituted heteroaryl, including optionally substituted pyridinyl such as pyridin-2-yl, 5-trifluoromethylpyridin-2-yl, 5-chloropyridin-2-yl, 5-bromopyridin-2-yl; including optionally substituted pyrimidinyl such as pyrimidin-2-yl and including optionally substituted benzodioxol such as 1,3-benzodioxol-5-yl.

In another preferred embodiment, the invention provides derivatives of Formula (I) wherein $R^2$ is H.

In another preferred embodiment, the invention provides derivatives of Formula (I) wherein $R^3$ is selected from optionally substituted aryl, including optionally substituted phenyl such as phenyl, 3-methoxyphenyl, 4-fluorophenyl, 3-fluorophenyl, 2-fluorophenyl, 1,2,4-oxadiazol-3-yl phenyl and optionally substituted heteroaryl, including optionally substituted pyridinyl such as pyridin-3-yl; including optionally substituted benzodioxol such as 1,3-benzodioxol-5-yl; including optionally substituted quinolinyl such as 3-quinolin-3-yl and including optionally substituted benzodioxolyl such as 1,3-benzodioxol-5-yl.

In another preferred embodiment, the invention provides derivatives of Formula (I) wherein $R^3$ is selected from optionally substituted $C_1$-$C_6$-alkyl, including ethyl, propyl, butyl and pentyl; optionally substituted aryl $C_1$-$C_6$-alkyl, including 4-phenyl methyl, optionally substituted heteroaryl $C_1$-$C_6$-alkyl, optionally substituted heteroaryl $C_1$-$C_6$-alkyl; optionally substituted $C_3$-$C_8$-cycloalkyl $C_1$-$C_6$-alkyl; and optionally substituted heterocycloalkyl $C_1$-$C_6$-alkyl, including morpholinomethyl such as morpholino-4-ylmethyl) and pyrrolidinylmethyl such as pyrrolidin-1-ylmethyl.

In another preferred embodiment, the invention provides derivatives of Formula (I) wherein $R^3$ is H.

In another preferred embodiment, the invention provides derivatives of Formula (I) wherein $R^3$ is optionally substituted amino $C_1$-$C_6$-alkyl, including diethyl amino methyl.

In another preferred embodiment, the invention provides derivatives of Formula (I) wherein $R^3$ is —Si(CH$_3$)$_3$.

In another preferred embodiment, the invention provides derivatives of Formula (I) wherein Y is CH$_2$.

In another preferred embodiment, the invention provides derivatives of Formula (I) wherein X is CH and Y is CH$_2$.

In another preferred embodiment, the invention provides derivatives of Formula (I) wherein X is N and Y is CH$_2$.

In another preferred embodiment, the invention provides derivatives of Formula (I) wherein A is a gem-dimethyl.

In another preferred embodiment, the invention provides derivatives of Formula (I) wherein B is methyl.

In another preferred embodiment, the invention provides derivatives of Formula (I) wherein n is 0.

In another preferred embodiment, the invention provides derivatives of Formula (I) wherein m is 0.

In another preferred embodiment, the invention provides derivatives of Formula (I) wherein n is 1.

In another preferred embodiment, the invention provides derivatives of Formula (I) wherein m is 1.

In another preferred embodiment, the invention provides derivatives of Formula (I) wherein n and m are 1.

In another preferred embodiment, the invention provides derivatives of Formula (I) wherein p is 1.

In another preferred embodiment, the invention provides derivatives of Formula (I) wherein p is 2.

In a preferred embodiment, the invention provides a sulfonyl amino cyclic derivative according to Formula (I) wherein $R^1$ is selected from optionally substituted aryl and optionally substituted heteroaryl; $R^2$ is H or methyl; Y is CH$_2$; X, A, B, n, m, p and $R^3$ is as defined above.

In another preferred embodiment, the invention provides a sulfonyl amino cyclic derivative according to Formula (I) wherein $R^1$ is selected from optionally substituted aryl and optionally substituted heteroaryl; $R^2$ is H or methyl; Y is CH$_2$; p is 1; X, A, B, n, m and $R^3$ is as defined above.

In another preferred embodiment, the invention provides a sulfonyl amino cyclic derivative according to Formula (I) wherein $R^1$ is selected from optionally substituted aryl and optionally substituted heteroaryl; $R^2$ is H or methyl; X is N; Y is CH$_2$; p is 2; A, B, n, m and $R^3$ is as defined above.

In another preferred embodiment, the invention provides a sulfonyl amino cyclic derivative according to Formula (I) wherein $R^1$ is selected from optionally substituted aryl and optionally substituted heteroaryl; $R^2$ is H or methyl; A is C(CH$_3$)$_2$; B is CH$_2$,; n and m are 1; X, Y, B, p and $R^3$ is as defined above.

In another preferred embodiment, the invention provides a sulfonyl amino cyclic derivative according to Formula (I) wherein $R^1$ is selected from optionally substituted aryl and optionally substituted heteroaryl; $R^2$ is H; X is N; Y is CH$_2$; n and m are 0; p is 1; $R^3$ is as defined above.

In a further preferred embodiment, the invention provides a sulfonyl amino cyclic derivative according to Formula (I) wherein $R^1$ is selected from optionally substituted aryl and optionally substituted heteroaryl; $R^2$ is H; X is N; Y is CH$_2$; n and m are 0; p is 1; and $R^3$ is selected from optionally substituted $C_1$-$C_6$-alkyl; optionally substituted aryl $C_1$-$C_6$-alkyl and optionally substituted heteroaryl $C_1$-$C_6$-alkyl.

In another further preferred embodiment, the invention provides a sulfonyl amino cyclic derivative according to Formula (I) wherein $R^1$ is selected from optionally substituted aryl and optionally substituted heteroaryl; $R^2$ is H; X is N; Y is CH$_2$; n and m are 0; p is 1; and $R^3$ is selected from optionally substituted aryl and optionally substituted heteroaryl.

Sulfonyl amino cyclic derivative of Formula (I) according to the invention include in particular those selected from the following group:

3-(1,3-benzodioxol-5-yl)-1-({[4-(4-fluorophenyl)-1-piperazinyl]sulfonyl}methyl)-2-propynyl(hydroxy)formamide;

1-({[4-(4-fluorophenyl)-1-piperazinyl]sulfonyl}methyl)-3-(trimethylsilyl)-2-propynyl(hydroxy)formamide;

hydroxy[1-{[(4-pyridin-2-ylpiperazin-1-yl)sulfonyl]methyl}-3-(trimethylsilyl)prop-2-yn-1-yl]formamide;

1-({[4-(4-fluorophenyl)-1-piperazinyl]sulfonyl}methyl)-3-phenyl-2-propynyl(hydroxy)formamide;

1-[({4-[4-(benzyloxy)phenyl]-1-piperazinyl}sulfonyl)methyl]-2-octynyl(hydroxy)formamide;

1-({[4-(4-fluorophenyl)-1-piperazinyl]sulfonyl}methyl)-4-phenyl-2-butynyl(hydroxy)formamide;

1-({[4-(4-fluorophenyl)-1-piperazinyl]sulfonyl}methyl)-2-octynyl(hydroxy)formamide;

1-({[4-(4-fluorophenyl)-1-piperazinyl]sulfonyl}methyl)-3-(3-pyridinyl)-2-propynyl(hydroxy)formamide;

hydroxy[1-({[4-(4-methoxyphenyl)-1-piperazinyl]sulfonyl}methyl)-3-(3-pyridinyl)-2-propynyl]formamide;

hydroxy[3-(3-methoxyphenyl)-1-({[4-(4-methoxyphenyl)-1-piperazinyl]sulfonyl}methyl)-2-propynyl]formamide;

4-(diethylamino)-1-({[4-(4-methoxyphenyl)-1-piperazinyl]sulfonyl}methyl)-2-butynyl(hydroxy)formamide;

hydroxy(1-{[(4-pyridin-2-ylpiperazin-1-yl)sulfonyl]methyl}prop-2-yn-1-yl)formamide;

hydroxy{1-[({4-[4-(methyloxy)phenyl]piperidin-1-yl}sulfonyl)methyl]-3-phenylprop-2-yn-1-yl}formamide;

hydroxy(1-{[(4-pyridin-2-ylpiperazin-1-yl)sulfonyl]methyl}hex-2-yn-1-yl)formamide;

[1-({[4-(2-fluorophenyl)piperazin-1-yl]sulfonyl}methyl)oct-2-yn-1-yl]hydroxyformamide;

hydroxy(1-{[(4-pyridin-2-ylpiperazin-1-yl)sulfonyl]methyl}oct-2-yn-1-yl)formamide;

hydroxy{1-[({4-[4-(trifluoromethyl)phenyl]piperazin-1-yl}sulfonyl)methyl]oct-2-yn-1-yl}formamide;

[1-({[4-(4-fluorophenyl)piperidin-1-yl]sulfonyl}methyl)oct-2-yn-1-yl]hydroxyformamide;

hydroxy{1-[({4-[4-(methyloxy)phenyl]piperidin-1-yl}sulfonyl)methyl]oct-2-yn-1-yl}formamide;

{1-({[4-(4-fluorophenyl)piperazin-1-yl]sulfonyl}methyl)-3-[3-(methyloxy)phenyl]prop-2-yn-1-yl}hydroxyformamide;

[1-({[4-(4-fluorophenyl)piperazin-1-yl]sulfonyl}methyl)hex-2-yn-1-yl]hydroxyformamide;

[1-({[4-(4-fluorophenyl)piperazin-1-yl]sulfonyl}methyl)-3-quinolin-3-ylprop-2-yn-1-yl]hydroxyformamide;

[1-({[4-(4-fluorophenyl)piperidin-1-yl]sulfonyl}methyl)-3-phenylprop-2-yn-1-yl]hydroxyformamide;
hydroxy(3-phenyl-1-{[(4-pyridin-2-ylpiperazin-1-yl)sulfonyl]methyl}prop-2-yn-1-yl)formamide;
hydroxy{3-phenyl-1-[({4-[4-(trifluoromethyl)phenyl]piperazin-1-yl}sulfonyl)methyl]prop-2-yn-1-yl}formamide;
hydroxy{1-[({4-[4-(methyloxy)phenyl]piperazin-1-yl}sulfonyl)methyl]-3-phenylprop-2-yn-1-yl}formamide;
{1-({[4-(4-fluorophenyl)piperazin-1-yl]sulfonyl}methyl)-3-[4-(1,2,4-oxadiazol-3-yl)phenyl]prop-2-yn-1-yl}hydroxyformamide;
hydroxy{1-[({4-[4-(methyloxy)phenyl]piperazin-1-yl}sulfonyl)methyl]oct-2-yn-1-yl}formamide;
(1-{[(4-biphenyl-4-ylpiperazin-1-yl)sulfonyl]methyl}-3-phenylprop-2-yn-1-yl)hydroxy formamide;
[1-({[4-(5-chloropyridin-2-yl)piperazin-1-yl]sulfonyl}methyl)oct-2-yn-1-yl]hydroxy formamide;
hydroxy(1-{[(4-pyrimidin-2-ylpiperazin-1-yl)sulfonyl]methyl}oct-2-yn-1-yl)formamide;
hydroxy(1-{[(4-phenylpiperazin-1-yl)sulfonyl]methyl}oct-2-yn-1-yl)formamide;
[1-({[4-(4-chlorophenyl)piperazin-1-yl]sulfonyl}methyl)oct-2-yn-1-yl]hydroxyformamide;
hydroxy{1-[({4-[2-(methyloxy)phenyl]piperazin-1-yl}sulfonyl)methyl]oct-2-yn-1-yl}formamide;
hydroxy{1-[({4-[3-(methyloxy)phenyl]piperazin-1-yl}sulfonyl)methyl]oct-2-yn-1-yl}formamide;
[1-({[4-(4-fluorophenyl)piperazin-1-yl]sulfonyl}methyl)-2,2-dimethyl-5-phenylpent-4-yn-1-yl]hydroxyformamide;
{4-(diethylamino)-1-[({4-[4-(methyloxy)phenyl]piperidin-1-yl}sulfonyl)methyl]but-2-yn-1-yl}hydroxyformamide;
hydroxy{1-[({4-[5-(trifluoromethyl)pyridin-2-yl]piperazin-1-yl}sulfonyl)methyl]oct-2-yn-1-yl}formamide;
hydroxy{1-[({4-[4-(phenyloxy)phenyl]piperazin-1-yl}sulfonyl)methyl]oct-2-yn-1-yl}formamide;
[1-({[4-(4-fluorophenyl)piperazin-1-yl]sulfonyl}methyl)hept-2-yn-1-yl]hydroxy formamide;
{3-(2-fluorophenyl)-1-[({4-[4-(methyloxy)phenyl]piperidin-1-yl}sulfonyl)methyl]prop-2-yn-1-yl}hydroxyformamide;
{3-(4-fluorophenyl)-1-[({4-[4-(methyloxy)phenyl]piperidin-1-yl}sulfonyl)methyl]prop-2-yn-1-yl}hydroxyformamide;
[1-({[4-(4-chlorophenyl)piperidin-1-yl]sulfonyl}methyl)oct-2-yn-1-yl]hydroxyformamide;
hydroxy[1-({[4-(4-methylphenyl)piperidin-1-yl]sulfonyl}methyl)oct-2-yn-1-yl]formamide;
{3-(3-fluorophenyl)-1-[({4-[4-(methyloxy)phenyl]piperidin-1-yl}sulfonyl)methyl]prop-2-yn-1-yl}hydroxyformamide;
hydroxy{1-[({4-[5-(trifluoromethyl)pyridin-2-yl]-1,4-diazepan-1-yl}sulfonyl)methyl]oct-2-yn-1-yl}formamide;
{1-[({4-[4-(ethyloxy)phenyl]piperazin-1-yl}sulfonyl)methyl]oct-2-yn-1-yl}hydroxy formamide;
[1-({[4-(5-bromopyridin-2-yl)piperazin-1-yl]sulfonyl}methyl)oct-2-yn-1-yl]hydroxy formamide;
[1-({[4-(4-fluorophenyl)piperazin-1-yl]sulfonyl}methyl)-4-morpholin-4-ylbut-2-yn-1-yl]hydroxyformamide;
[1-({[4-(3-chlorophenyl)piperazin-1-yl]sulfonyl}methyl)oct-2-yn-1-yl]hydroxyformamide;
[1-({[4-(1,3-benzodioxol-5-yl)piperazin-1-yl]sulfonyl}methyl)oct-2-yn-1-yl]hydroxy formamide;
hydroxy{1-[({4-[3-(methyloxy)phenyl]piperazin-1-yl}sulfonyl)methyl]-3-phenylprop-2-yn-1-yl}formamide;
hydroxy[1-({[4-(4-methylphenyl)piperidin-1-yl]sulfonyl}methyl)-3-phenylprop-2-yn-1-yl]formamide;
[1-({[4-(4-chlorophenyl)piperazin-1-yl]sulfonyl}methyl)-3-phenylprop-2-yn-1-yl]hydroxyformamide;
{1-[({4-[4-(ethyloxy)phenyl]piperazin-1-yl}sulfonyl)methyl]-3-phenylprop-2-yn-1-yl}hydroxyformamide;
[1-({[4-(5-bromopyridin-2-yl)piperazin-1-yl]sulfonyl}methyl)-2,2-dimethyl-5-phenylpent-4-yn-1-yl]hydroxyformamide;
{2,2-dimethyl-5-phenyl-1-[({4-[4-(trifluoromethyl)phenyl]piperazin-1-yl}sulfonyl)methyl]pent-4-yn-1-yl}hydroxyformamide;
[1-({[4-(5-chloropyridin-2-yl)piperazin-1-yl]sulfonyl}methyl)hex-2-yn-1-yl]hydroxy formamide;
{1-[({4-[4-(ethyloxy)phenyl]piperazin-1-yl}sulfonyl)methyl]-2,2-dimethyl-5-phenylpent-4-yn-1-yl}hydroxyformamide;
[1-({[4-(3,4-dimethoxyphenyl)piperazin-1-yl]sulfonyl}methyl)oct-2-yn-1-yl]hydroxy formamide;
[1-({[4-(4-ethyloxyphenyl)-1,4-diazepan-1-yl]sulfonyl}methyl)oct-2-yn-1-yl]hydroxyl formamide;
[1-({[(2R)-4-(4-fluorophenyl)-2-methylpiperazin-1-yl]sulfonyl}methyl)oct-2-yn-1-yl]hydroxyformamide;
[1-({[4-(4-fluorophenyl)piperazin-1-yl]sulfonyl}methyl)-2,2-dimethylpent-4-yn-1-yl]hydroxyformamide;
[1-({[4-(4-fluorophenyl)piperazin-1-yl]sulfonyl}methyl)-4-pyrrolidin-1-ylbut-2-yn-1-yl]hydroxyformamide;
[1-({[4-(4-fluorophenyl)piperazin-1-yl]sulfonyl}methyl)-2,2-dimethyl-6-morpholin-4-yl hex-4-yn-1-yl]hydroxyformamide;
[1-({[4-(4-fluorophenyl)piperazin-1-yl]sulfonyl}methyl)-2,2-dimethyl hept-4-yn-1-yl]hydroxyformamide.

In another embodiment of the invention, are provided a sulfonyl amino cyclic derivative according to Formula (I) for use as a medicament.

In another embodiment of the invention, is provided a pharmaceutical composition comprising a sulfonyl amino cyclic derivative according to the invention and a pharmaceutically acceptable carrier, diluent or excipient thereof.

In another embodiment of the invention, is provide a use of according to Formula (I) for the preparation of a medicament for the prophylaxis and/or treatment of a disorder selected from autoimmune disorders and inflammatory diseases, including multiple sclerosis, inflammatory bowel disease and rheumatoid arthritis; stroke, cardiovascular diseases, neurodegenerative diseases, cancer, pre-term labor, respiratory diseases including emphysema, chronic obstructive pulmonary disease (COPD); and fibrosis, including liver and pulmonary, pancreatic fibrosis and liver fibrosis.

In another embodiment of the invention, is provided a use of derivatives according to Formula (I) for the modulation, in particular for the inhibition, of the matrix metalloproteinase activity. Particularly, is provided a use according to the invention wherein said matrix metalloproteinase is selected from MMP-2, MMP-9 and MMP-12. Preferably, compounds according to the invention are selective inhibitors of metalloproteinease MMP-12 over MMP-1.

In another embodiment, the invention provides a method of treatment and/or prophylaxis of a disease comprising the administration of a compound according to Formula (I), in a patient in need thereof and wherein the disease is selected from autoimmune disorders and inflammatory diseases, including multiple sclerosis, inflammatory bowel disease and rheumatoid arthritis; stroke, cardiovascular diseases, neurodegenerative diseases, cancer, pre-term labor, respiratory diseases including emphysema, chronic obstructive pulmonary disease (COPD); and fibrosis, including liver and pulmonary, pancreatic fibrosis and liver fibrosis.

In another embodiment, the invention provides a process for the preparation of derivative of Formula (I) according to the invention, comprising the step of reacting a compound of Formula (II) with a formylating agent of Formula (FA):

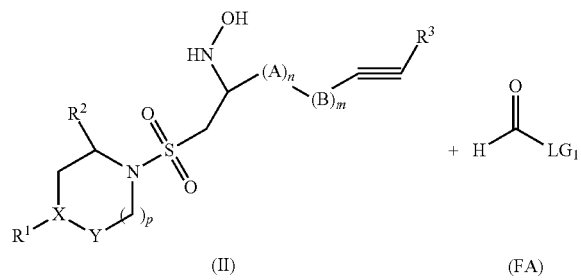

wherein A, B, R$^1$, R$^2$, R$^3$, X, Y, m, n and p are defined above; LG$_1$ is a group selected from OH, —OAc, —O—Piv, —OCH$_2$CN, —OCH$_2$—CF$_3$, —O-Phenyl and OPfp.

In another embodiment, the invention provides a compound according to Formula (II):

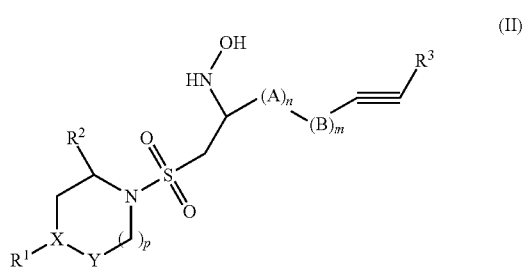

wherein A, B, R$^1$, R$^2$, R$^3$, X, Y, m, n and p are defined above.

In a further embodiment, the invention provides a compound according to Formula (II) selected from the group:

N-[3-(1,3-benzodioxol-5-yl)-1-({[4-(4-fluorophenyl)-1-piperazinyl]sulfonyl}methyl)-2-propynyl]hydroxylamine;
1-(4-fluorophenyl)-4-{[2-(hydroxyamino)-4-(trimethylsilyl)-3-butynyl]sulfonyl}piperazine;
1-{[2-(hydroxyamino)-4-(trimethylsilyl)-3-butynyl]sulfonyl}-4-(2-pyridinyl)piperazine;
1-(4-fluorophenyl)-4-{[2-(hydroxyamino)-4-phenyl-3-butynyl]sulfonyl}piperazine;
1-[4-(benzyloxy)phenyl]-4-{[2-(hydroxyamino)-3-nonynyl]sulfonyl}piperazine;
1-(4-fluorophenyl)-4-{[2-(hydroxyamino)-5-phenyl-3-pentynyl]sulfonyl}piperazine;
1-(4-fluorophenyl)-4-{[2-(hydroxyamino)-3-nonynyl]sulfonyl}piperazine;
1-(4-fluorophenyl)-4-{[2-(hydroxyamino)-4-(3-pyridinyl)-3-butynyl]sulfonyl}piperazine;
1-{[2-(hydroxyamino)-4-(3-pyridinyl)-3-butynyl]sulfonyl}-4-(4-methoxyphenyl)piperazine;
1-{[2-(hydroxyamino)-4-(3-methoxyphenyl)-3-butynyl]sulfonyl}-4-(4-methoxyphenyl)piperazine;
N,N-diethyl-4-(hydroxyamino)-5-{[4-(4-methoxyphenyl)-1-piperazinyl]sulfonyl}-2-pentyn-1-amine;
1-{[2-(hydroxyamino)but-3-yn-1-yl]sulfonyl}-4-pyridin-2-yl piperazine;
1-{[2-(hydroxyamino)-4-phenylbut-3-yn-1-yl]sulfonyl}-4-(4-methoxyphenyl)piperidine;
1-{[2-(hydroxyamino)hept-3-yn-1-yl]sulfonyl}-4-pyridin-2-ylpiperazine;
1-(2-fluorophenyl)-4-{[2-(hydroxyamino)non-3-yn-1-yl]sulfonyl}piperazine;
1-{[2-(hydroxyamino)non-3-yn-1-yl]sulfonyl}-4-pyridin-2-ylpiperazine;
1-{[2-(hydroxyamino)non-3-yn-1-yl]sulfonyl}-4-[4-(trifluoromethyl)phenyl]piperazine;
4-(4-fluorophenyl)-1-{[2-(hydroxyamino)non-3-yn-1-yl]sulfonyl}piperidine;
1-{[2-(hydroxyamino)non-3-yn-1-yl]sulfonyl}-4-(4-methoxyphenyl)piperidine;
1-(4-fluorophenyl)-4-{[2-(hydroxyamino)-4-(3-methoxyphenyl)but-3-yn-1-yl]sulfonyl}piperazine;
1-(4-fluorophenyl)-4-{[2-(hydroxyamino)hept-3-yn-1-yl]sulfonyl}piperazine;
1-{[2-(hydroxyamino)-4-phenylbut-3-yn-1-yl]sulfonyl}-4-[4-(trifluoromethyl)phenyl]piperazine;
3-[4-{[4-(4-fluorophenyl)piperazin-1-yl]sulfonyl}-3-(hydroxyamino)but-1-yn-1-yl]quinoline;
4-(4-fluorophenyl)-1-{[2-(hydroxyamino)-4-phenylbut-3-yn-1-yl]sulfonyl}piperidine;
1-{[2-(hydroxyamino)-4-phenylbut-3-yn-1-yl]sulfonyl}-4-pyridin-2-ylpiperazine;
1-{[2-(hydroxyamino)-4-phenylbut-3-yn-1-yl]sulfonyl}-4-(4-methoxyphenyl)piperazine;
1-(4-fluorophenyl)-4-({2-(hydroxyamino)-4-[4-(1,2,4-oxadiazol-3-yl)phenyl]but-3-yn-1-yl}sulfonyl)piperazine;
1-{[2-(hydroxyamino)non-3-yn-1-yl]sulfonyl}-4-(4-methoxyphenyl)piperazine;
1-biphenyl-4-yl-4-{[2-(hydroxyamino)-4-phenylbut-3-yn-1-yl]sulfonyl}piperazine;
1-(5-chloropyridin-2-yl)-4-{[2-(hydroxyamino)non-3-yn-1-yl]sulfonyl}piperazine;
2-(4-{[2-(hydroxyamino)non-3-yn-1-yl]sulfonyl}piperazin-1-yl)pyrimidine;
1-{[2-(hydroxyamino)non-3-yn-1-yl]sulfonyl}-4-phenylpiperazine;
1-(4-chlorophenyl)-4-{[2-(hydroxyamino)non-3-yn-1-yl]sulfonyl}piperazine;
1-{[2-(hydroxyamino)non-3-yn-1-yl]sulfonyl}-4-(2-methoxyphenyl)piperazine;
1-{[2-(hydroxyamino)non-3-yn-1-yl]sulfonyl}-4-(3-methoxyphenyl)piperazine;
1-(4-fluorophenyl)-4-{[2-(hydroxyamino)-3,3-dimethyl-6-phenylhex-5-yn-1-yl]sulfonyl}piperazine;
N,N-diethyl-4-(hydroxyamino)-5-{[4-(4-methoxyphenyl)piperidin-1-yl]sulfonyl}pent-2-yn-1-amine;
1-{[2-(hydroxyamino)non-3-yn-1-yl]sulfonyl}-4-[5-(trifluoromethyl)pyridin-2-yl]piperazine;
1-{[2-(hydroxyamino)non-3-yn-1-yl]sulfonyl}-4-(4-phenoxyphenyl)piperazine;
1-(4-fluorophenyl)-4-{[2-(hydroxyamino)oct-3-yn-1-yl]sulfonyl}piperazine;
1-{[4-(2-fluorophenyl)-2-(hydroxyamino)but-3-yn-1-yl]sulfonyl}-4-(4-methoxy phenyl)piperidine;
1-{[4-(4-fluorophenyl)-2-(hydroxyamino)but-3-yn-1-yl]sulfonyl}-4-(4-methoxy phenyl)piperidine;
4-(4-chlorophenyl)-1-{[2-(hydroxyamino)non-3-yn-1-yl]sulfonyl}piperidine;
1-{[2-(hydroxyamino)non-3-yn-1-yl]sulfonyl}-4-(4-methylphenyl)piperidine;
1-{[4-(3-fluorophenyl)-2-(hydroxyamino)but-3-yn-1-yl]sulfonyl}-4-(4-methoxy phenyl)piperidine;
1-{[2-(hydroxyamino)non-3-yn-1-yl]sulfonyl}-4-[5-(trifluoromethyl)pyridin-2-yl]-1,4-diazepane;

1-(4-ethoxyphenyl)-4-{[2-(hydroxyamino)non-3-yn-1-yl]sulfonyl}piperazine;
1-(5-bromopyridin-2-yl)-4-{[2-(hydroxyamino)non-3-yn-1-yl]sulfonyl}piperazine;
4-[5-{[4-(4-fluorophenyl)piperazin-1-yl]sulfonyl}-4-(hydroxyamino)pent-2-yn-1-yl]morpholine;
1-(3-chlorophenyl)-4-{[2-(hydroxyamino)non-3-yn-1-yl]sulfonyl}piperazine;
1-(1,3-benzodioxol-5-yl)-4-{[2-(hydroxyamino)non-3-yn-1-yl]sulfonyl}piperazine;
1-{[2-(hydroxyamino)-4-phenylbut-3-yn-1-yl]sulfonyl}-4-(3-methoxyphenyl)piperazine;
1-{[2-(hydroxyamino)-4-phenylbut-3-yn-1-yl]sulfonyl}-4-(4-methylphenyl)piperidine;
1-(4-chlorophenyl)-4-{[2-(hydroxyamino)-4-phenylbut-3-yn-1-yl]sulfonyl}piperazine;
1-(4-ethoxyphenyl)-4-{[2-(hydroxyamino)-4-phenylbut-3-yn-1-yl]sulfonyl}piperazine;
1-(5-bromopyridin-2-yl)-4-{[2-(hydroxyamino)-3,3-dimethyl-6-phenylhex-5-yn-1-yl]sulfonyl}piperazine;
1-{[2-(hydroxyamino)-3,3-dimethyl-6-phenylhex-5-yn-1-yl]sulfonyl}-4-[4-(trifluoro methyl)phenyl]piperazine;
1-(5-chloropyridin-2-yl)-4-{[2-(hydroxyamino)hept-3-yn-1-yl]sulfonyl}piperazine;
1-(4-ethoxyphenyl)-4-{[2-(hydroxyamino)-3,3-dimethyl-6-phenylhex-5-yn-1-yl]sulfonyl}piperazine;
1-(3,4-dimethoxyphenyl)-4-{[2-(hydroxyamino)non-3-yn-1-yl]sulfonyl}piperazine;
1-(4-ethoxyphenyl)-4-{[2-(hydroxyamino)non-3-yn-1-yl]sulfonyl}-1,4-diazepane;
(2R)-4-(4-fluorophenyl)-1-{[2-(hydroxyamino)non-3-yn-1-yl]sulfonyl}-2-methyl piperazine;
1-(4-fluorophenyl)-4-{[2-(hydroxyamino)-3,3-dimethylhex-5-yn-1-yl]sulfonyl}piperazine
1-(4-fluorophenyl)-4-{[2-(hydroxyamino)-5-pyrrolidin-1-ylpent-3-yn-1-yl]sulfonyl}piperazine;
4-[7-{[4-(4-fluorophenyl)piperazin-1-yl]sulfonyl}-6-(hydroxyamino)-5,5-dimethylhept-2-yn-1-yl]morpholine;
1-(4-fluorophenyl)-4-{[2-(hydroxyamino)-3,3-dimethyloct-5-yn-1-yl]sulfonyl}piperazine.

In another embodiment, the invention provides a process for the preparation of derivative of Formulae (I) or (II) according to the invention, comprising the step of reacting a compound of Formula (III) with hydroxylamine or a hydroxylamine derivative of Formula (HA):

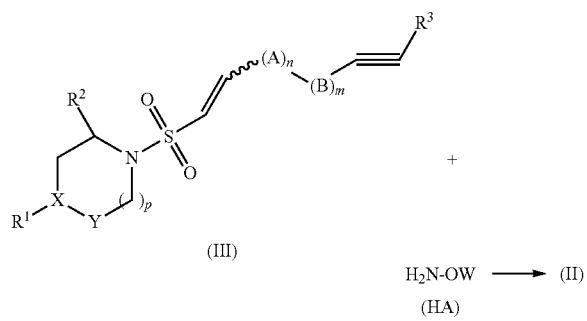

$H_2N-OW \longrightarrow$ (II)

(HA)

wherein A, B, $R^1$, $R^2$, $R^3$, X, Y, m, n and p are defined above; W is selected from H, Benzyl, TMS, TBDMS and THP.

In another embodiment, the invention provides a compound according to Formula (III):

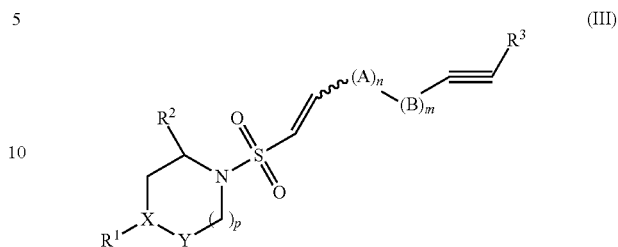

wherein A, B, $R^1$, $R^2$, $R^3$, X, Y, m, n and p are defined above.

In a further embodiment, the invention provides a compound according to Formula (III) selected from the group:
1-{[(1E)-4-(1,3-benzodioxol-5-yl)-1-buten-3-ynyl]sulfonyl}-4-(4-fluorophenyl)piperazine;
1-{[(1Z)-4-(1,3-benzodioxol-5-yl)-1-buten-3-ynyl]sulfonyl}-4-(4-fluorophenyl)piperazine;
1-(4-fluorophenyl)-4-{[(1E)-4-(trimethylsilyl)-1-buten-3-ynyl]sulfonyl}piperazine;
1-(4-fluorophenyl)-4-{[(1Z)-4-(trimethylsilyl)-1-buten-3-ynyl]sulfonyl}piperazine;
1-(2-pyridinyl)-4-{[(1E)-4-(trimethylsilyl)-1-buten-3-ynyl]sulfonyl}piperazine;
1-(2-pyridinyl)-4-{[(1Z)-4-(trimethylsilyl)-1-buten-3-ynyl]sulfonyl}piperazine;
1-(4-fluorophenyl)-4-{[(1E)-4-phenyl-1-buten-3-ynyl]sulfonyl}piperazine;
1-(4-fluorophenyl)-4-{[(1Z)-4-phenyl-1-buten-3-ynyl]sulfonyl}piperazine;
benzyl 4-{4-[(1E)-1-nonen-3-ynylsulfonyl]-1-piperazinyl}phenyl ether;
benzyl 4-{4-[(1Z)-1-nonen-3-ynylsulfonyl]-1-piperazinyl}phenyl ether;
1-(4-fluorophenyl)-4-{[(1E)-5-phenyl-1-penten-3-ynyl]sulfonyl}piperazine;
1-(4-fluorophenyl)-4-{[(1Z)-5-phenyl-1-penten-3-ynyl]sulfonyl}piperazine;
1-(4-fluorophenyl)-4-[(1E)-1-nonen-3-ynylsulfonyl]piperazine;
1-(4-fluorophenyl)-4-[(1Z)-1-nonen-3-ynylsulfonyl]piperazine;
1-(4-fluorophenyl)-4-{[(1E)-4-(3-pyridinyl)-1-buten-3-ynyl]sulfonyl}piperazine;
1-(4-fluorophenyl)-4-{[(1Z)-4-(3-pyridinyl)-1-buten-3-ynyl]sulfonyl}piperazine;
1-(4-methoxyphenyl)-4-{[(1E)-4-(3-pyridinyl)-1-buten-3-ynyl]sulfonyl}piperazine;
1-(4-methoxyphenyl)-4-{[(1Z)-4-(3-pyridinyl)-1-buten-3-ynyl]sulfonyl}piperazine;
1-(4-methoxyphenyl)-4-{[(1E)-4-(3-methoxyphenyl)-1-buten-3-ynyl]sulfonyl}piperazine;
1-(4-methoxyphenyl)-4-{[(1Z)-4-(3-methoxyphenyl)-1-buten-3-ynyl]sulfonyl}piperazine;
N,N-diethyl-N-((4E)-5-{[4-(4-methoxyphenyl)-1-piperazinyl]sulfonyl}-4-penten-2-ynyl)amine;
N,N-diethyl-N-((4Z)-5-{[4-(4-methoxy phenyl)-1-piperazinyl]sulfonyl}-4-penten-2-ynyl)amine;
1-[(1E)-but-1-en-3-yn-1-ylsulfonyl]-4-pyridin-2-ylpiperazine;
1-[(1Z)-but-1-en-3-yn-1-ylsulfonyl]-4-pyridin-2-ylpiperazine;

4-(4-methoxyphenyl)-1-{[-4-phenylbut-1-en-3-yn-1-yl]sulfonyl}piperidine;
1-[-hept-1-en-3-yn-1-ylsulfonyl]-4-pyridin-2-ylpiperazine;
1-(2-fluorophenyl)-4-[-non-1-en-3-yn-1-ylsulfonyl]piperazine;
1-[-non-1-en-3-yn-1-ylsulfonyl]-4-pyridin-2-ylpiperazine;
1-[-non-1-en-3-yn-1-ylsulfonyl]-4-[4-(trifluoromethyl)phenyl]piperazine;
4-(4-fluorophenyl)-1-[-non-1-en-3-yn-1-ylsulfonyl]piperidine;
4-(4-methoxyphenyl)-1-[-non-1-en-3-yn-1-ylsulfonyl]piperidine;
1-(4-fluorophenyl)-4-{[-4-(3-methoxyphenyl)but-1-en-3-yn-1-yl]sulfonyl}piperazine;
1-(4-fluorophenyl)-4-[-hept-1-en-3-yn-1-ylsulfonyl]piperazine;
1-{[-4-phenylbut-1-en-3-yn-1-yl]sulfonyl}-4-[4-(trifluoromethyl)phenyl]piperazine;
3-((3E)-4-{[4-(4-fluorophenyl)piperazin-1-yl]sulfonyl}but-3-en-1-yn-1-yl)quinoline;
4-(4-fluorophenyl)-1-{[-4-phenylbut-1-en-3-yn-1-yl]sulfonyl}piperidine;
1-{[-4-phenylbut-1-en-3-yn-1-yl]sulfonyl}-4-pyridin-2-ylpiperazine;
1-(4-methoxyphenyl)-4-{[-4-phenylbut-1-en-3-yn-1-yl]sulfonyl}piperazine;
1-(4-fluorophenyl)-4-({-4-[4-(1,2,4-oxadiazol-3-yl)phenyl]but-1-en-3-yn-1-yl}sulfonyl)piperazine;
1-(4-methoxyphenyl)-4-[-non-1-en-3-yn-1-ylsulfonyl]piperazine;
1-biphenyl-4-yl-{[-4-phenylbut-1-en-3-yn-1-yl]sulfonyl}piperazine;
1-(5-chloropyridin-2-yl)-4-[-non-1-en-3-yn-1-ylsulfonyl]piperazine;
2-{4-[-non-1-en-3-yn-1-ylsulfonyl]piperazin-1-yl}pyrimidine;
1-[-non-1-en-3-yn-1-ylsulfonyl]-4-phenylpiperazine;
1-(4-chlorophenyl)-4-[-non-1-en-3-yn-1-ylsulfonyl]piperazine;
1-(2-methoxyphenyl)-4-[-non-1-en-3-yn-1-ylsulfonyl]piperazine;
1-(3-methoxyphenyl)-4-[-non-1-en-3-yn-1-ylsulfonyl]piperazine;
1-{[-3,3-dimethyl-6-phenylhex-1-en-5-yn-1-yl]sulfonyl}-4-(4-fluorophenyl)piperazine;
N,N-diethyl-5-{[4-(4-methoxyphenyl)piperidin-1-yl]sulfonyl}pent-4-en-2-yn-1-amine;
1-[-non-1-en-3-yn-1-ylsulfonyl]-4-[5-(trifluoromethyl)pyridin-2-yl]piperazine;
1-[-non-1-en-3-yn-1-ylsulfonyl]-4-(4-phenoxyphenyl)piperazine;
1-(4-fluorophenyl)-4-[-oct-1-en-3-yn-1-ylsulfonyl]piperazine;
1-{[-4-(2-fluorophenyl)but-1-en-3-yn-1-yl]sulfonyl}-4-(4-methoxyphenyl)piperidine;
1-{[-4-(4-fluorophenyl)but-1-en-3-yn-1-yl]sulfonyl}-4-(4-methoxyphenyl)piperidine;
4-(4-chlorophenyl)-1-[-non-1-en-3-yn-1-ylsulfonyl]piperidine;
4-(4-methylphenyl)-1-[-non-1-en-3-yn-1-ylsulfonyl]piperidine;
1-{[-4-(3-fluorophenyl)but-1-en-3-yn-1-yl]sulfonyl}-4-(4-methoxyphenyl)piperidine;
1-[-non-1-en-3-yn-1-ylsulfonyl]-4-[5-(trifluoromethyl)pyridin-2-yl]-1,4-diazepane;
1-(4-ethoxyphenyl)-4-[-non-1-en-3-yn-1-ylsulfonyl]piperazine;
1-(5-bromopyridin-2-yl)-4-[-non-1-en-3-yn-1-ylsulfonyl]piperazine;
4-(-5-{[4-(4-fluorophenyl)piperazin-1-yl]sulfonyl}pent-4-en-2-yn-1-yl)morpholine;
1-(3-chlorophenyl)-4-[-non-1-en-3-yn-1-ylsulfonyl]piperazine;
1-(1,3-benzodioxol-5-yl)-4-[-non-1-en-3-yn-1-ylsulfonyl]piperazine;
1-(3-methoxyphenyl)-4-{[-4-phenylbut-1-en-3-yn-1-yl]sulfonyl}piperazine;
4-(4-methylphenyl)-1-{[-4-phenylbut-1-en-3-yn-1-yl]sulfonyl}piperidine;
1-(4-chlorophenyl)-4-{[-4-phenylbut-1-en-3-yn-1-yl]sulfonyl}piperazine;
1-(4-ethoxyphenyl)-4-{[-4-phenylbut-1-en-3-yn-1-yl]sulfonyl}piperazine;
1-(5-bromopyridin-2-yl)-4-{[-3,3-dimethyl-6-phenylhex-1-en-5-yn-1-yl]sulfonyl}piperazine;
1-{[-3,3-dimethyl-6-phenylhex-1-en-5-yn-1-yl]sulfonyl}-4-[4-(trifluoromethyl)phenyl]piperazine;
1-(5-chloropyridin-2-yl)-4-[-hept-1-en-3-yn-1-ylsulfonyl]piperazine;
1-{[-3,3-dimethyl-6-phenylhex-1-en-5-yn-1-yl]sulfonyl}-4-(4-ethoxyphenyl)piperazine;
1-(3,4-dimethoxyphenyl)-4-[-non-1-en-3-yn-1-ylsulfonyl]piperazine;
1-(4-ethoxyphenyl)-4-[-non-1-en-3-yn-1-ylsulfonyl]-1,4-diazepane;
(2R)-4-(4-fluorophenyl)-2-methyl-1-[-non-1-en-3-yn-1-ylsulfonyl]piperazine;
1-{[-3,3-dimethylhex-1-en-5-yn-1-yl]sulfonyl}-4-(4-fluorophenyl)piperazine;
1-(4-fluorophenyl)-4-{[-5-pyrrolidin-1-ylpent-1-en-3-yn-1-yl]sulfonyl}piperazine;
4-(7-{[4-(4-fluorophenyl)piperazin-1-yl]sulfonyl}-5,5-dimethylhept-6-en-2-yn-1-yl)morpholine;
1-{[-3,3-dimethyloct-1-en-5-yn-1-yl]sulfonyl}-4-(4-fluorophenyl)piperazine.

In another embodiment, the invention provides a process for the preparation of derivative of Formulae (I), (II) or (III) according to the invention, comprising the step of reacting a compound of Formula (VIII) with a reagent such as MsCl, TMSCl, DBU, HCl.

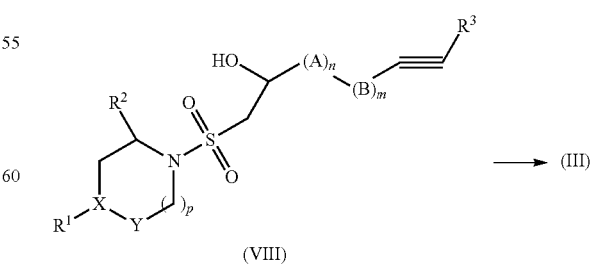

wherein A, B, $R^1$, $R^2$, $R^3$, X, Y, m, n and p are defined above.

In another embodiment, the invention provides a compound according to Formula (VIII):

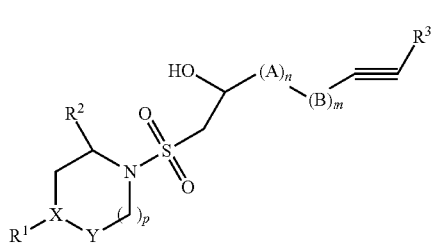

wherein A, B, $R^1$, $R^2$, $R^3$, X, Y, m, n and p are defined above.

In another embodiment, the invention provides a process for the preparation of derivative of Formulae (I), (II), (III) or (VIII) according to the invention, comprising the step of reducing the ketone group of a compound of Formula (VII) in the presence of a reducing agent such as $NaBH_4$ in alcoholic solvent like MeOH or EtOH.

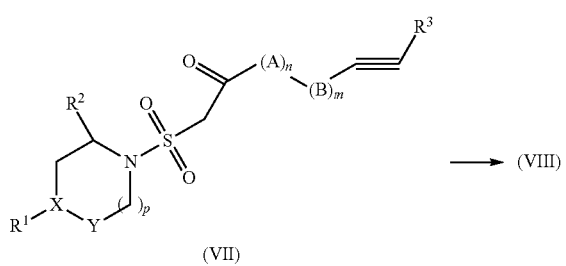

wherein A, B, $R^1$, $R^2$, $R^3$, X, Y, m, n and p are defined above.

In another embodiment, the invention provides a compound according to Formula (VII):

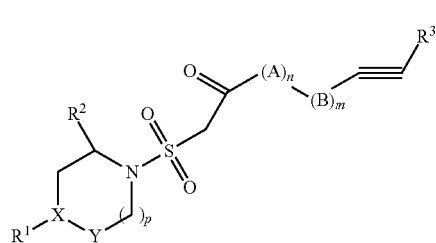

wherein A, B, $R^1$, $R^2$, $R^3$, X, Y, m, n and p are defined above.

The compounds of invention have been named according the standards used in the program "ACD/Name" from Advanced Chemistry Development Inc., ACD/Labs (7.06 Release).

The compounds of Formula (I) are useful for the treatment and/or prophylaxis of autoimmune disorders, inflammatory diseases, cardiovascular diseases, neurodegenerative diseases, stroke, cancer, pre-term labor, respiratory diseases and fibrosis, including multiple sclerosis, arthritis, emphysema, chronic obstructive pulmonary disease, liver and pulmonary fibrosis.

Compounds according to the present invention also comprise their tautomers, geometrical isomers, optically active forms as enantiomers, diastereomers and racemate forms, as well as pharmaceutically acceptable salts thereof. Preferred pharmaceutically acceptable salts of the compounds according to Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of the invention and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

In another embodiment, the compounds of the invention can be used in the treatment of autoimmune diseases, especially demyelinating diseases such as multiple sclerosis, alone or in combination with a co-agent useful in the treatment of autoimmune diseases, wherein the co-agent is for example selected from the following compounds:

(a) Interferons, e. g. pegylated or non-pegylated interferons, e. g. administered by subcutaneous, intramuscular or oral routes, preferably interferon beta;
(b) Glatiramer, e. g. in the acetate form;
(c) Immunosuppressants with optionally antiproliferative/antineoplastic activity, e. g. mitoxantrone, methotrexate, azathioprine, cyclophosphamide, or steroids, e. g. methylprednisolone, prednisone or dexamethasone, or steroid-secreting agents, e. g. ACTH;
(d) Adenosine deaminase inhibitors, e. g. Cladribine;
(e) Inhibitors of VCAM-1 expression or antagonists of its ligand, e. g. antagonists of the α4/β1 integrin VLA-4 and/or alpha-4-beta-7 integrins, e. g. natalizumab (ANTEGREN).

Further co-agents such as anti-inflammatory agents (in particular for demyelinating diseases such as multiple sclerosis) are described below:

A further anti-inflammatory agent is Teriflunomide which is described in WO 02/080897

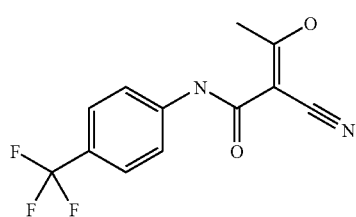

Still a further anti-inflammatory agent is Fingolimod which is described in EP-727406, WO 2004/028251 and WO 2004/028251.

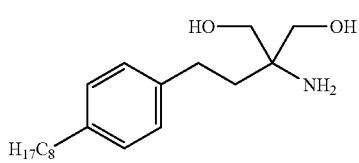

Still a further anti-inflammatory agent is Laquinimod which is described in WO 99/55678.

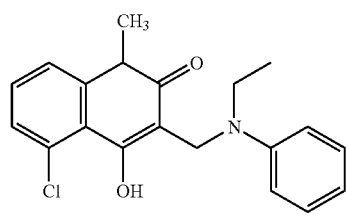

Still a further anti-inflammatory agent is Tensirolimus which is described in WO 02/28866.

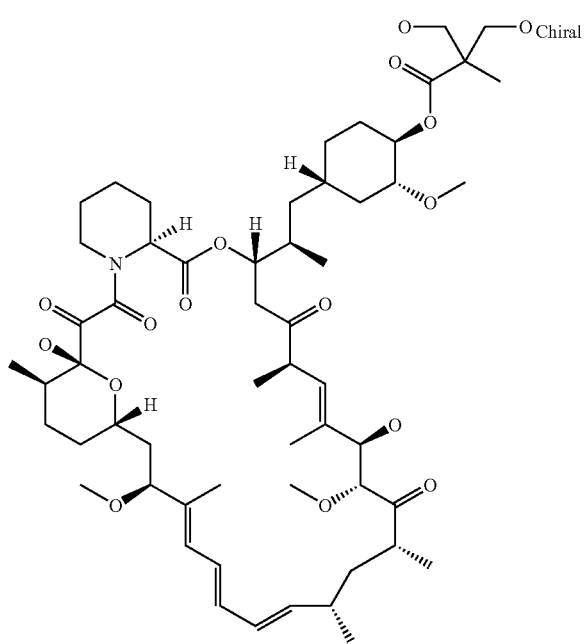

Still a further anti-inflammatory agent is Xaliprodene which is described in WO 98/48802.

Still a further anti-inflammatory agent is Deskar Pirfenidone which is described in WO 03/068230.

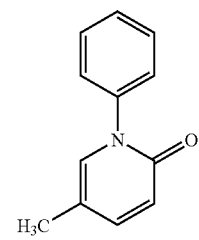

Still a further anti-inflammatory agent is the below benzothiazole derivative which is described in WO 01/47920.

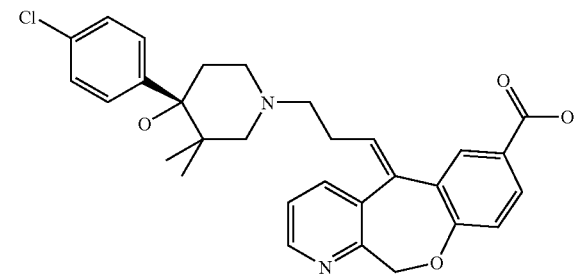

Still a further anti-inflammatory agent is one of the hydroxamic acid derivatives described in WO 03/070711.

Still a further anti-inflammatory agent is MLN3897 which is described in WO 2004/043965.

Still a further anti-inflammatory agent is CDP323 which is described in WO 99/67230.

Still a further anti-inflammatory agent is Simvastatin which is described in WO 01/45698.

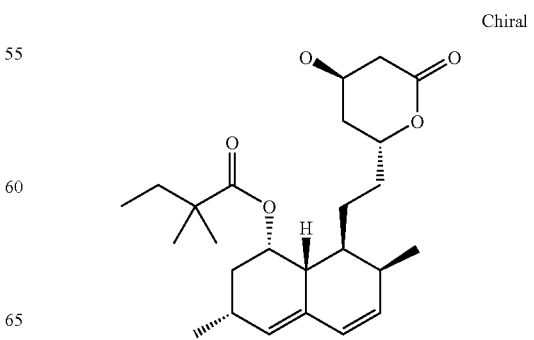

Still a further anti-inflammatory agent is Fampridine which is described in U.S. Pat. No. 5,540,938.

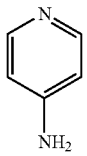

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the derivative of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the sulfonyl amino cyclic derivatives of Formula (I) in such compositions is typically a minor component, frequently ranging between 0.05 to 10% by weight with the remainder being the injectable carrier and the like.

The above described components for orally administered or injectable compositions are merely representative. The compounds of this invention can also be administered in sustained release forms or from sustained release drug delivery systems. Further materials as well as processing techniques and the like are set out in *Remington's Pharmaceutical Sciences*, 20$^{th}$ Edition, 2000, Marck Publishing Company, Easton, Pa. (for example in Part 5) which is incorporated herein by reference.

Synthesis of Compounds of the Invention:

The novel derivatives according to Formula (I) can be prepared from readily available starting materials by several synthetic approaches, using both solution-phase and solid-phase chemistry protocols or mixed solution and solid phase protocols. Examples of synthetic pathways for the will be described.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq. (equivalent), mL (milliliter), μL (microliter), ACN (acetonitrile), BINAP (2,2'-bis(di phenylphosphino)-1,1'-binaphthalene), Boc (tert-Butoxycarbonyl), BuLi (Butyl Lithium), $CDCl_3$ (deuterated chloroform), $CD_3OD$ (Deuterated methanol), c-Hex (Cyclohexane), DBU (1,5-diazabicyclo(5,4,0) undec-5-ene), DCC (dicyclohexyl carbodiimide), DCM (Dichloromethane), DEA (diethylamine), DEAD (Diethyl azodicarboxylate), DIC (Diisopropyl carbo diimide), DIEA (Diisopropylethylamine), DMF (Dimethylformamide), DMSO (Dimethyl sulfoxide), DMSO-$d_6$ (Deuterated dimethylsulfoxide), EDC (1-(3-Dimethyl-amino-propyl)-3-ethyl-carbodiimide), EtOAc (Ethyl acetate), ESI (Electro-spray ionization), $Et_2O$ (Diethyl ether), EtOH (Ethanol), FA (Formic acid), Fmoc (9-Fluorenyl methoxycarbonyl), HATU (Dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), LC (Liquid Chromatography), LDA (Litium diisopropyl amide), LiHMDS (Litium Hexa methyl) MeOH (Methanol), MS (mass spectrometry), MsCl (Mesylchloride), MTBE (Methyl tert-butyl ether), MW (micro-wave irradiation), NMM (N-methyl morpholine), NMR (Nuclear Magnetic Resonance), OMs (O-mesyl), O—Piv (O—Pivaloyl), OPfp (O-pentafluorophenol), OTs (O-Tosyl), rt (room temperature), SPE (solid phase extraction), TBDMS (tert-Butyldimethylsilyl), TBTU (2-(1-H-benzotriazole-1-yl)-1,1,3,3-tetramethyluromium tetrafluoro borate), TEA (Triethylamine), TFA (Trifluoroacetic acid), THF (Tetrahydrofuran), THP (Tetrahydropyranyl), TLC (Thin Layer Chromatography), TMAD (N,N,N',N'-tetrametyl azodicarboxamide), TMS (Trimethylsilyl), TMSCl (Trimethylsilyl chloride), TsCl (Tosyl chloride), UV (Ultraviolet), Z (Benzyloxycarbonyl).

Synthetic Approaches:

Generally, compounds of Formula (I) may be obtained by formylation of a compound of Formula (II) wherein $R^1$, $R^2$, $R^3$, X, Y, A, B, n and m are defined as above (Scheme 1 below).

General protocols for such formylation are given below in the examples, and use formylating agents well known from those skilled in the art such as formylating agents of Formula (FA) wherein LG$_1$ is a group selected from OH, —OAc, —O—Piv, —OCH$_2$CN, —OCH$_2$—CF$_3$, —O-Phenyl and OPfp.

For example formylating agent may be obtained by reacting formic acid with acetic anhydride.

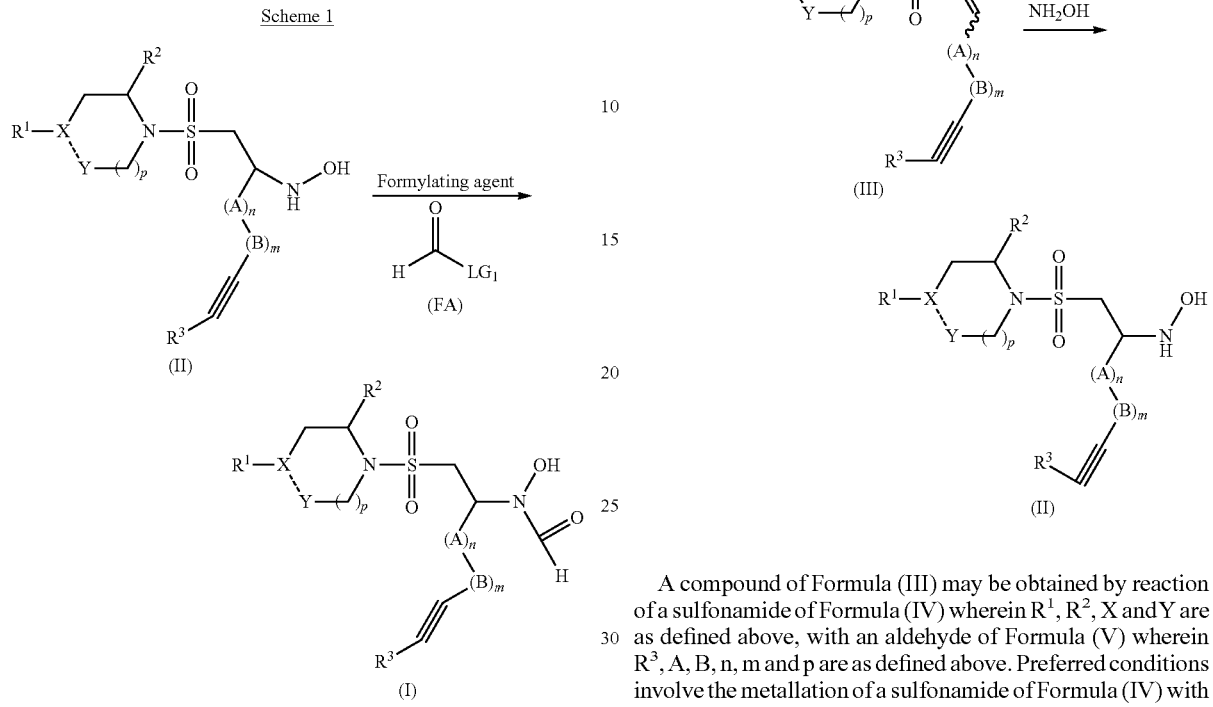

A preferred process for preparing a compound of Formula (II) consists in reacting hydroxylamine with a compound of Formula (III) wherein R$^1$, R$^2$, R$^3$, X, Y, A, B, n, m and p are as defined above, in a suitable solvent like THF at a temperature between 0° C. and 100° C. (Scheme 2 below).

A compound of Formula (III) may be obtained by reaction of a sulfonamide of Formula (IV) wherein R$^1$, R$^2$, X and Y are as defined above, with an aldehyde of Formula (V) wherein R$^3$, A, B, n, m and p are as defined above. Preferred conditions involve the metallation of a sulfonamide of Formula (IV) with a base like, but not limited to LiHMDS, LDA or BuLi, followed by the reaction of the resulting metallated sulfonamide with a chlorophosphate such as ClPO(OEt)$_2$ and an aldehyde of Formula (V) in a suitable solvent such as THF. Others conditions may involve the metallation of a sulfonamide of Formula (IV) with a base followed directly by the reaction of the resulting metallated sulfonamide with an aldehyde of Formula (V) in the presence or not of an additive such as TMSCl, MsCl or TsCl.

An alternative route for the preparation of compounds of Formula (II) may be the initial reaction of a sulfonamide of Formula (IV), that has been first metallated as described above, with an ester of Formula (VI) wherein R is a C$_1$-C$_6$ alkyl or C$_3$-C$_8$ cycloalkyl or benzyl and R$^3$, A, B, n and m are defined as above to lead to a ketone of Formula (VII) wherein R$^1$, R$^2$, R$^3$, X, Y, A, B, n, m and p are as defined above (Scheme 3 below).

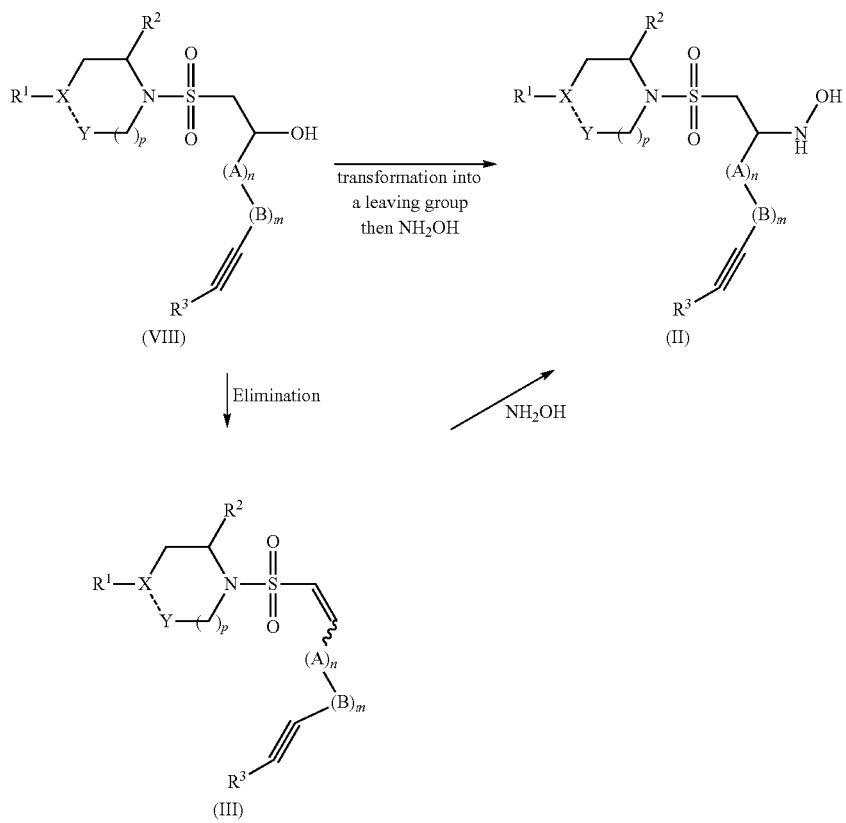

Compounds of Formula (II) may result from the reaction of a ketone of Formula (VII) with hydroxylamine in a suitable solvent such as DCM followed by the chemoselective reduction of the formed oxime of Formula (IX) wherein $R^1$, $R^2$, $R^3$, X, Y, A, B, n, m and p are as defined above. Preferred reducing agent for this transformation may be for example $NaBH_3CN$.

Alternatively, a ketone of Formula (VII) may be chemoselectively reduced in the presence of reducing agent (such as $NaBH_4$ in alcoholic solvent like MeOH or EtOH) into an alcohol of Formula (VIII) wherein $R^1$, $R^2$, $R^3$, X, Y, A, B, n, m and p are as defined above (Scheme 3 above).

The alcohol group of the alcohol of Formula (VIII) can be eliminated to give an alkene of Formula (III) by reaction with a base such as NaOH, DBU, DIEA or in the presence of MsCl, TMSCl or TsCl. A compound of Formula (II) may then be obtained by reacting hydroxylamine with an alkene of Formula (III) wherein $R^1$, $R^2$, $R^3$, X, Y, A, B, n, m and p are as defined above, in a suitable solvent like THF at a temperature between 0° C. and 100° C. (Scheme 3 above).

A complementary route for the preparation of compounds of Formula (II) may result from the transformation of the hydroxy group of an alcohol of Formula (VIII) into a leaving group such as OMs, OTs, Cl, Br or I, following conditions well known to those skilled in the art followed by its displacement with hydroxylamine. Similarly, an alcohol of Formula (VIII) can be reacted with phosphines (e.g. $PPh_3$, $P(nBu)_3$) in the presence of diazodicarboxylic derivatives such as DEAD, TMAD and hydroxylamine or hydroxylamine derivatives (such as BocO—NHBoc, ZO—NHZ, wherein Z is Benzyloxy carbonyl).

Intermediates of Formula (IV) are prepared by reacting a compound of Formula (X) wherein X, Y, $R^1$, $R^2$ and p are as defined above with mesyl chloride in conditions well known to those skilled in the art (Scheme 4 below).

Scheme 4

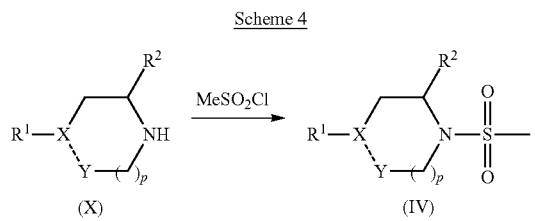

Intermediates of Formula (X) are commercially available or may be prepared using conditions well known to those skilled in the art. For example, intermediates of Formula (X) wherein X is a carbon atom may be prepared following procedure described in Wustrow et al., *Synthesis*, 1991, 993. Intermediates of Formula (X) wherein X is a nitrogen atom may be prepared following procedure described in Brenner et al., *Tetrahedron*, 2002, 58(34), 6913-6924 or in *Tetrahedron Letters*, 1996, 37(26), 4463-4466.

Intermediates of Formula (V) are either commercially available or can be obtained by methods and conditions well known to those skilled in the art. One preferred method to obtain intermediates of Formula (V) consists in the oxidation of an alcohol of Formula (XI) wherein A, B, m, n and $R^3$ are as defined above using oxidation conditions well known to those skilled in the art like (such as Dess-Martin reagent or MnO$_2$ when m and n are 0) (Scheme 5 below).

Scheme 5

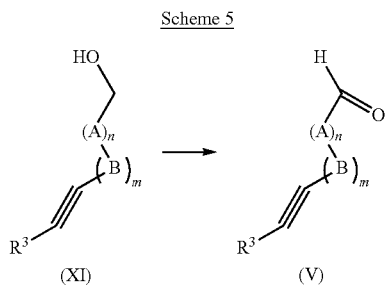

Intermediates of Formula (VI) are either commercially available or can be obtained by methods and conditions well known to those skilled in the art. One preferred method to is obtain intermediates of Formula (VI) with at least m or n is not 0 and R$^3$ is an optionally substituted aryl or a optionally substituted heteroaryl consists in the reaction of a compound of Formula (XII) wherein A, B, n and m are as above described and R is a C$_1$-C$_6$ alkyl or cycloalkyl or benzyl with R$^3$-LG$_2$ wherein R$^3$ is an optionally substituted aryl or a optionally substituted heteroaryl and LG$_2$ is an halogen or —OSO$_2$CF$_3$ in the presence of a Pd(0) catalyst (Scheme 6 below).

Scheme 6

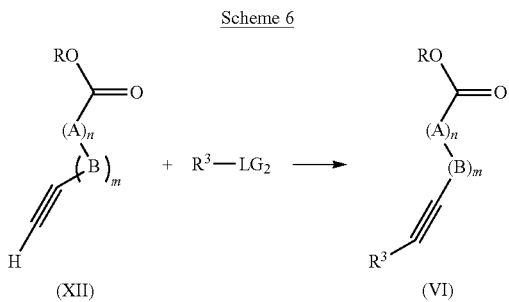

Another preferred method to obtain intermediates of formula (VI) wherein n and m are 1 consists in the reaction of a compound of Formula (XIII) wherein, A and R are defined as above and n is 1 with a compound of formula (XIV) wherein LG$_3$ is a leaving group such as OMs, OTs, Cl, Br or I, m is 1, and R$^3$ and B are defined as above. Preferred conditions involve the metallation of intermediate (XIII) with a base like, but not limited to LiHMDS, LDA or BuLi in a suitable solvent such as THF (Scheme 7 below).

Scheme 7

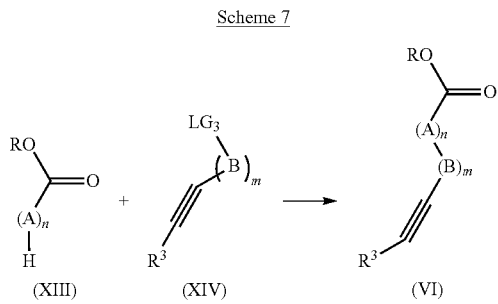

According to a further general process, compounds of Formula (I) can be converted to alternative compounds of Formula (I), employing suitable interconversion techniques well known by a person skilled in the art.

Compounds of Formula (I) and its precursors of Formulae (II) and (VIII) contain at least one chiral center, and all individual optically active forms and combinations of these are disclosed as individual and specific embodiments of the invention, as well as their corresponding racemates. The processes outlined in the above Schemes, in particular Schemes 1 and 2, afford compounds of Formula (I) and its precursors of Formulae (II) and (VIII) in racemic form or as mixtures of diastereomers, in cases where additional chiral centers are present. Pure stereoisomers can be obtained from the mixtures using procedures well known to those skilled in the art including for example separation of isomers by chiral HPLC or formation of diastereoisomeric derivatives having convenient optically active auxiliary species followed by separation and then cleavage of the auxiliary species (see for example Basha et al., 1994, *J. Org. Chem.*, 59, 6103-6106)

In the following the present invention shall be illustrated by means of some examples, which are not construed to be viewed as limiting the scope of the invention.

The following commercially available reagents/resins were used: propargyl alcohol (from Fluka), manganese(IV) oxide or MnO$_2$ (from Aldrich), 4-diethylamino-2-butyn-1-ol (from Aldrich), 3-(3-methoxyphenyl)prop-2-yn-1-ol (from GFS), 2-bromopyrimidine (from Aldrich), copper(I) iodide or CuI (from Aldrich), 2,2-dimethylbut-3-ynoic acid benzylester (from Betapharma), 1-(4-fluorophenyl)piperazine dihydrochloride (from Aldrich), methane sulfonyl chloride (from Fluka), 1-(2-pyridyl)piperazine (from Aldrich), 1-[4-(benzyloxy)phenyl]piperazine hydrochloride (from EmkaChem), 1-(4-methoxyphenyl)piperazine (from Chess), lithiumbis(trimethylsilyl)amide (from Aldrich), diethylchloro phosphate (from Aldrich), hydroxylamine (from Aldrich), acetic anhydride (from Fluka), formic acid (from Fluka), 3-trimethylsilylpropinal (from ABCR), phenylpropioaldehyde (from Fluka), 2-octynal (from Aldrich), ethyl isobutyrate (from Aldrich), 4-(4-methoxyphenyl)piperidine (from Astatech), 1-(4-trifluoromethylphenyl)piperazine (from Emkachem), 4-(4-fluorophenyl)piperidine.HCl (from Astatech), 1-(biphenyl-4-yl)piperazine (from Apollo), 1-(2-pyrimidyl)piperazine (from Emkachem), 1-(4-chlorophenyl)piperazine (from Acros), 1-(3-methoxyphenyl)-piperazine (from Chess), 1-[5-(trifluoromethyl)pyridin-2-yl]piperazine (from Maybridge), 1-[4-trifluoromethyl)pyrimidin-2-yl]-1,4-diazepane (from Acros), 4-(4-chlorophenyl)piperidine (from Astatech), 4-(4-methylphenyl)piperidine (from Astatech), 1-[5-(trifluoromethyl)pyrid-2-yl]-1,4-diazepane (from Fluorochem), 1-(4-ethoxyphenyl)piperazine (from Emkachem), 1-(5-bromopyridin-2-yl) piperazine (from J&W Pharmlab), 1-(1,3-benzodioxol-5-yl)piperazine (from Fluorochem), 1-(3,4-dimethoxyphenyl)-piperazine hydrochloride (from Fluorochem), 1-bromoethoxybenzene (from Aldrich), 1,4-diazepane (from Aldrich), 1-bromo-4-fluorobenzene (from Aldrich), (R)-2-methylpiperazine (from Astatech), Butyradehyde (from Aldrich), 2-hexyn-1-ol (from Aldrich), 3-Quinolin-3-yl-prop-2-yn-1-ol (from Chembridge), 3-hydroxyprop-1-ynyl)benzonitrile (from Maybridge), 1-(methylsulfonyl)-4-phenylpiperazine (from Ambinter), 1-(2-fluorophenyl)-4-(methylsulfonyl)piperazine (from Ambinter), 1-(4-chlorophenyl)-4-(methylsulfonyl)piperazine (from Ambinter), 1-(2-methoxyphenyl)-4-(methylsulfonyl)piperazine (from Ambinter), 4-diethylamino-2-butyl-1-ol (from Aldrich), 2-heptyn-1-ol (Aldrich), 3-(3-fluorophenyl)pro-2-yn-1-ol (from Apollo), 1-(3-chlorophenyl)-4-(methylsulfonyl)piperazine (from Ambinter).

The HPLC data provided in the examples described below were obtained as followed. HPLC columns: Waters Xterra® MS $C_8$ column 50 mm×4.6 mm at a flow of 2 mL/min, 8 min gradient from 0.1% TFA in $H_2O$ to 0.07% TFA in $CH_3CN$.

The preparative HPLC were obtained with a Waters Xterra® Prep MS $C_8$ 10 μm column is 300 mm×30 mm; UV detection (254 nM and 220 nM); flow: 30 mL/min. The MS data provided in the examples described below were obtained as followed: Mass spectrum: LC/MS Waters ZMD (ESI). The GC/MS were obtained with an Agilent 6890 Gas Chromatograph; Column: DB-1HS, 10 m×0.1 mm I.D.×0.1 μm; Carrier Gas: Helium at 45 cm/sec at 50° C. (0.6 mL/min); constant flow mode; Oven: 50° C. 1 min; 50° C./min to 330° C., hold for 5 min. Injector: 250° C., 0.2 μL. Detector: Agilent 5973 MSD; transfer line at 325° C., EI SIM. The $^1$H-NMR data provided in the examples described below were obtained with a Bruker DPX-300 MHz NMR machine. Experiences under microwave irradiation were performed using the Emrys Optimizer (from Biotage, previously Personal Chemistry) at the power of 300 W.

Intermediate A1:
3-(1,3-benzodioxol-5-yl)-2-propynal

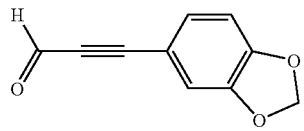

Intermediate A1

To a solution of 3-(1,3-benzodioxol-5-yl)prop-2-yn-1-ol (242 mg, 1.37 mmol, obtained as described in Nugent et al., 1987, *J. Am. Chem. Soc.,* 109, 2788) in anhydrous DCM (12 mL) was added $MnO_2$ (2.70 g, 31.1 mmol) portion wise over 2 h. The resulting mixture was stirred at rt for one additional hour, then filtered on a bed of Celite and the filtrates were evaporated under reduced pressure to give 123 mg (51%) of the title compound as a brown solid. HPLC, Rt: 2.76 min (purity: 98.9%). $^1$H NMR (CDCl$_3$) δ: 9.37 (s, 1H), 7.18 (m, 1H), 7.00 (m, 1H), 6.82 (d, J=8.3 Hz, 1H), 6.03 (s, 2H).

Intermediate A2: phenyl-2-butynal

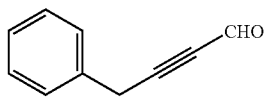

Intermediate A2

4-Phenyl-2-butyn-1-ol (550 mg; 3.76 mmol, obtained as described in *Bull. Soc. Chim. Fr,* 1954, 816) was dissolved in DCM (10 mL) and $MnO_2$ (1.64 g; 18.8 mmol) was added. The mixture was stirred at rt and the reaction was monitored by TLC (EtOAc/c-Hex 10/90, staining with iodine). $MnO_2$ was regularly added (1.64 g; 18.8 mmol; three times). $MnO_2$ was removed by filtration on a bed of celite. After washing the celite with DCM, the filtrates were then concentrated under reduced pressure. Purification of the crude by flash chromatography on silica (gradient EtOAc/c-Hex 5:95 to 30:70) gave the title compound as an range oil (60 mg, 11% yield). $^1$H NMR (CDCl$_3$) δ: 9.22 (s, 1H), 7.26 (m, 5H), 3.80 (s, 2H).

Intermediate A3: 3-(3-pyridinyl)-2-propynal

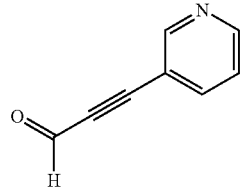

Intermediate A3

To a solution of 3-(3-pyridinyl)-2-propyn-1-ol (250 mg, 1.88 mmol, obtained as described in *J. Org Chem.* 1998, 63, 1109-1118) in anhydrous DCM (10 ml) under argon was added $MnO_2$ (3.66 g, 42 mmol) portion wise over 1.5 h. The reaction mixture was stirred at rt for one additional hour. Then the reaction mixture was poured on the top of a column of silica gel and eluted with cHex/EtOAc (2:1 then 1:1) to give 43 mg (17%) of the title compound as a yellow powder. $^1$H NMR (CDCl$_3$) δ: 9.46 (s, 1H), 8.85 (dd, J=2.1, 0.8 Hz, 1H), 8.71 (dd, J=5.0, 1.7 Hz, 1H), 7.91 (ddd, J=8.0, 2.1, 1.7 Hz, 1H), 7.38 (ddd, J=8.0, 5.0, 0.8 Hz, 1H).

Intermediate A4: 4-(diethylamino)-2-butynal

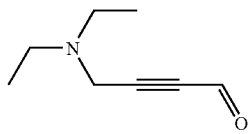

Intermediate A4

To a solution of 4-diethylamino-2-butyn-1-ol (1.00 g, 7.08 mmol) in anhydrous DCM (60 mL) was added $MnO_2$ (20 g, 230 mmol) portion wise on one hour. The resulting mixture was stirred at rt for two additional hours, then filtered on a bed of Celite. The filtrates were evaporated under reduced pressure to give 352 mg (36%) the title compound as an orange oil (352 mg, 36% yield). $^1$H NMR (CDCl$_3$) δ: 9.22 (s, 1H), 3.65 (s, 2H), 2.58 (q, J=7.2 Hz, 4H), 1.08 (t, J=7.2 Hz, 6H).

Intermediate A5: 3-(3-methoxyphenyl)-2-propynal

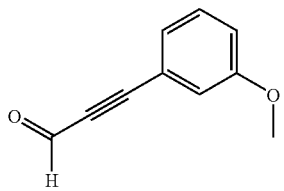

Intermediate A5

To a solution of 3-(3-methoxyphenyl)prop-2-yn-1-ol (500 mg, 3.08 mmol) in anhydrous DCM (20 ml) under argon was added $MnO_2$ (7.8 g, 90 mmol) portion wise over 2 h. The reaction mixture was stirred at rt for one additional hour. Then the reaction mixture was filtered and the solvent was removed under reduced pressure. Purification by flash chromatography on silica gel (cHex:EtOAc, gradient 9:1 to 4:1) gave 122 mg (25%) of the title compound as a yellow oil. HPLC, Rt: 2.9 min (purity: 99.9%). ¹H NMR (CDCl₃) δ: 9.43 (s, 1H), 7.32 (dd, J=8.3, 7.7 Hz, 1H), 7.22 (ddd, J=7.7, 1.4, 1.1 Hz, 1H), 7.12 (dd, J=2.6, 1.4 Hz, 1H), 7.05 (ddd, J=8.3, 2.6, 1.1 Hz, 1H), 3.83 (s, 3H).

Intermediate A6:
2,2-dimethyl-6-morpholin-4-ylhex-4-ynal

Step a) Formation of Ethyl
2,2-dimethyl-6-morpholin-4-ylhex-4-ynoate

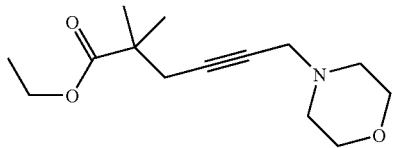

To a solution of ethyl isobutyrate (530 μl; 4.08 mmol) in THF (5 mL) was added lithium bis(trimethylsilyl)amide (7.30 mL; solution 1.00 M in THF; 7.30 mmol) at −78° C. The mixture was removed from the cooling bath and stirred for 30 min. It was then cannulated over a suspension of 4-(4-chlorobut-2-yn-1-yl)morpholine hydrochloride (prepared as described by Gomez et al., 1997 *Tetrahedron*, 53(50), 17201-17210; 714 mg; 3.40 mmol) in THF (5 mL) maintained at −78° C. The reaction mixture was left in the cooling bath and allowed to warm up to rt. After 3 h, it was quenched with water and extracted twice with EtOAc. Combined organic phases were washed with brine, dried over magnesium sulfate, filtrated and concentrated. Purification of the crude by flash chromatography on silica (gradient DCM:MeOH 100:0 to 90:10) gave the title compound as a colorless oil (600 mg, 70% yield). ¹H NMR (DMSO-d6) δ: 4.11 (qd, J=7.1 Hz, 2H), 4.14 (m, 4H), 3.31 (t, J=2.1Hz, 0.6H), 3.25 (m, 1.4H), 2.52 (m, 4H), 2.43 (t, J=2.3 Hz, 2H), 1.25 (s, 6H), 1.23 (t, J=7.0 Hz, 3H).

Step b) Formation of
2,2-dimethyl-6-morpholin-4-ylhex-4-yn-1-ol

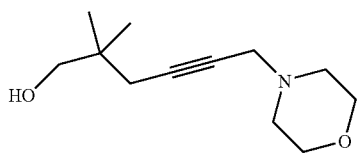

To a solution of ethyl 2,2-dimethyl-6-morpholin-4-ylhex-4-ynoate (380 mg; 1.50 mmol) in THF (5 mL) at 0° C. was added LiAlH₄ (2.25 mL; solution 1.00 M in THF; 2.25 mmol). The mixture was stirred at 0° C. for 1 h and quenched with water (80 μL), 80 μL NaOH 15% (80 μL) and water (3×80 μL). The suspension thus obtained was then filtrated through a celite pad and rinsed several times with EtOAc. The filtrate was concentrated under reduced pressure to give 302 mg of the title compound as an orange oil (307 mg, 97% yield). GC/MS, m/z: 211, Rt: 4.13 min.

Step c) Formation of
2,2-dimethyl-6-morpholin-4-ylhex-4-ynal (A6)

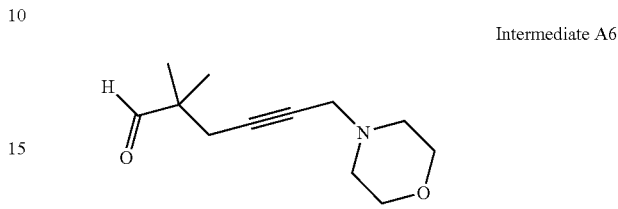

To a solution of oxalyl chloride (152 μl; 1.74 mmol) in DCM (4 mL) at −78° C. was added a solution of DMSO (237 μl; 3.34 mmol) in DCM (2 mL). The mixture was stirred for 5 min before the addition of a solution of 2,2-dimethyl-6-morpholin-4-ylhex-4-yn-1-ol (307 mg; 1.45 mmol) in DCM (2 mL). The mixture was stirred again at −78° C. for 15 min and TEA (1.05 mL) was added. It was then brought back to rt and stirred for 2 h. Water was added. Organic phase was washed with a saturated solution of NaHCO₃ and brine. It was dried over magnesium sulfate, filtrated and concentrated to give the title compound as a colorless oil (303 mg, quantitative). ¹H NMR (CDCl₃) δ: 9.51 (s, 1H), 3.73 (m, 4H), 3.27 (m, 2H), 2.56 (m, 4H), 2.36 (m, 2H), 1.14 (s, 6H).

Intermediate B1:
1-(4-fluorophenyl)-4-(methylsulfonyl)piperazine

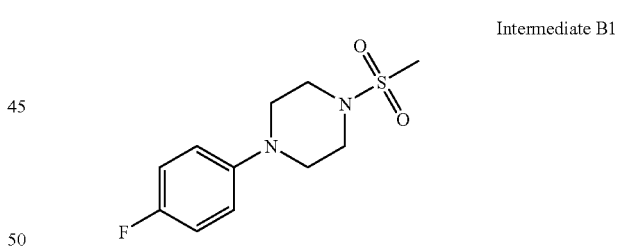

To a suspension of 1-(4-fluorophenyl)piperazine dihydrochloride (2.53 g; 10.0 mmol; 1.0 eq.) in anhydrous DCM (50 mL) was added TEA (3.33 g; 33.0 mmol; 3.3 eq.) and the resulting mixture was chilled at 0° C. A 1N solution of methanesulfonyl chloride (1.26 g; 11.0 mmol; 1.1 eq.) in DCM (11 mL) was added dropwise. After 20 min at 0° C., the reaction mixture was stirred at rt for 3 h. Water was added and the mixture extracted with DCM. The combined organic layers were washed with an aqueous saturated solution of NaHCO₃, water, brine then dried over MgSO₄, filtered and evaporated to give a white powder. Crystallization from EtOAc gave a white solid (1.98 g, 76% yield). HPLC, Rt: 2.3 min (purity: 100%). ¹H NMR (CDCl₃) δ: 7.08-6.83 (m, 4H), 3.41 (m, 4H), 3.22 (m, 4H), 2.85 (s, 3H).

Intermediate B2: 1-(methylsulfonyl)-4-(2-pyridinyl)piperazine

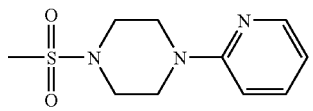

The title compound was prepared following procedure described for Intermediate B1, but starting from 1-(2-pyridyl)piperazine (3.59 g, 22 mmol, 1.0 eq.) as a white powder (3.14 g, 65% yield). $^1$H NMR (CDCl$_3$) δ: 8.22 (d, 4.3 Hz, 1H), 7.54 (m, 1H), 6.71 (m, 2H), 3.71 (m, 4H), 3.35 (m, 4H), 2.82 (s, 3H).

Intermediate B3: 1-[4-(benzyloxy)phenyl]-4-(methylsulfonyl)piperazine

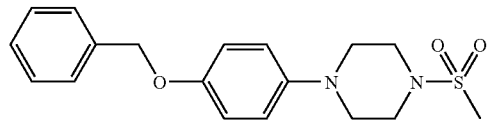

The title compound was prepared following procedure described for Intermediate B1, but starting from 1-[4-(benzyloxy)phenyl]piperazine hydrochloride (2.0 g, 6.56 mmol, 1 eq.) as a white powder (1.85 g, 82% yield). HPLC, Rt: 1.2 min (purity: 99.8%). LC/MS, M$^+$(ESI): 347.1, M$^-$(ESI): 345.0.

Intermediate B4: 1-(4-methoxyphenyl)-4-(methylsulfonyl)piperazine

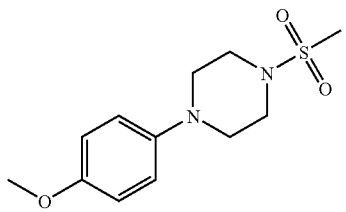

The title compound was prepared following procedure described for Intermediate B1, but starting from 1-(4-methoxyphenyl)piperazine (1920 mg, 10.0 mmol), as an off-white powder (2180 mg, 81% yield). HPLC, Rt: 1.2 min (purity: 99.8%). LC/MS, M$^+$(ESI): 271.1. $^1$H NMR (CDCl$_3$) δ: 6.91 (m, 2H), 6.83 (m, 2H), 3.77 (s, 3H), 3.37 (m, 4H), 3.15 (m, 4H), 2.82 (s, 3H).

Intermediate B5: 4-(4-methoxyphenyl)-1-(methylsulfonyl)piperidine

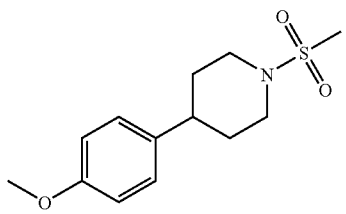

The title compound was prepared, following procedure described for Intermediate B1, but starting from 4-(4-methoxyphenyl)piperidine (2.0 g) as a white powder (2.2 g, 78.11%). HPLC, Rt: 3.04 min (purity: 100%). LC/MS, M$^+$(ESI): 270.1.

Intermediate B6: 1-(methylsulfonyl)-4-[4-(trifluoromethyl)phenyl]piperazine

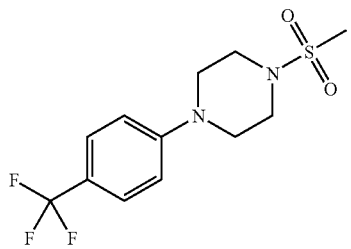

The title compound was prepared, following procedure described for Intermediate B1, but starting from 1-(4-trifluoromethylphenyl)piperazine (2.3 g) as a yellow powder (2.34 g, 76% yield). HPLC, Rt: 3.56 min (purity: 99.9%). LC/MS, M$^+$(ESI): 309.1.

Intermediate B7: 4-(4-fluorophenyl)-1-(methylsulfonyl)piperidine

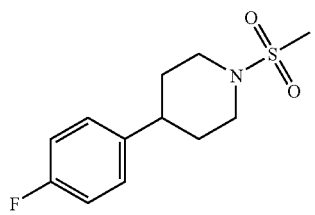

The title compound was prepared, following procedure described for Intermediate B1, but starting from 4-(4-fluorophenyl)piperidine.HCl (2.15 g) as a beige powder (1.79 g, 70% yield). HPLC, Rt: 3.18 min (purity: 100%). LC/MS, M$^+$(ESI): 258.1.

Intermediate B8: 1-[1,1'-biphenyl]-4-yl-4-(methylsulfonyl)piperazine

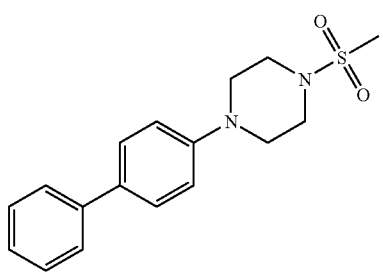

The title compound was prepared, following procedure described for Intermediate B1, but starting from 1-(biphenyl-4-yl)piperazine (1.79 g), as a white powder (2.12 g, 89% yield). HPLC, Rt: 3.60 min (purity: 99.8%). LC/MS, M$^+$(ESI): 317.2.

Intermediate B9: 1-(5-chloropyridin-2-yl)-4-(methylsulfonyl)piperazine

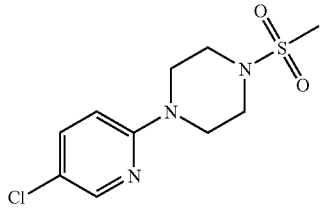
Intermediate B9

The title compound was prepared, following procedure described for Intermediate B1, but starting from 1-(5-chloro-2-pyridinyl)piperazine (prepared as described by Swanson et al., 2005, *Journal of Medicinal Chemistry*, 48(6), 1857-1872, 395 mg, 2 mmol) as a beige powder (379 mg, 69% yield). HPLC, Rt: 1.60 min (purity: 100%). LC/MS, M$^+$(ESI): 276.2.

Intermediate B10: 2-[4-(methylsulfonyl)piperazin-1-yl]pyrimidine

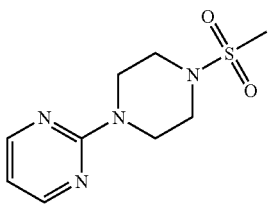
Intermediate B10

The title compound was prepared, following procedure described for Intermediate B1, but starting from, 1-(2-pyrimidyl)piperazine (2.10 g) as a white powder (2.49 g, 80% yield). HPLC, Rt: 1.14 min (purity: 100%). LC/MS, M$^+$(ESI): 243.3.

Intermediate B11: 1-(4-chlorophenyl)-4-(methylsulfonyl)piperazine

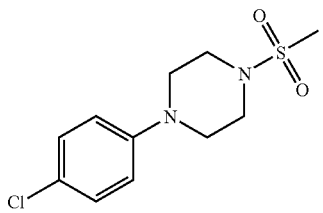
Intermediate B11

The title compound was prepared, following procedure described for Intermediate B1, but starting from 1-(4-chlorophenyl)piperazine (1.97 g, 10 mmol) as a white powder (2.08 g, 75% yield). HPLC, Rt: 3.02 min (purity: 100%). LC/MS, M$^+$(ESI): 275.2.

Intermediate B12: 1-(3-methoxyphenyl)-4-(methylsulfonyl)piperazine

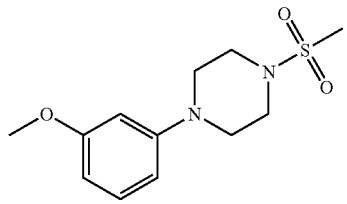
Intermediate B12

The title compound was prepared, following procedure described for Intermediate B1, but starting from 1-(3-methoxyphenyl)-piperazine (2.27 g) as a white powder (2.58 g, 81% yield). HPLC, Rt: 2.13 min (purity: 100%). LC/MS, M$^+$(ESI): 271.3.

Intermediate B13: 1-(Methylsulfonyl)-4-[5-(trifluoromethyl)pyridin-2-yl]piperazine

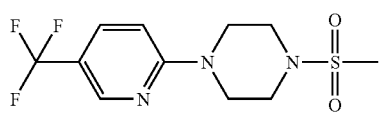
Intermediate B13

To a solution of 1-[5-(trifluoromethyl)pyridin-2-yl]piperazine (23 g, 0.099 mol) and TEA (42 mL 0.298 mol) in dry dichloromethane (400 mL) maintained at 0° C. under nitrogen atmosphere, was added methanesulfonylchloride (12.6 g, 0.109 mol) over a period of 20 min. The reaction mixture was stirred at room temperature for 6 h and diluted with water. The organic layer was separated, washed with brine, dried over magnesium sulfate, filtrated and concentrated. The crude product was recrystallized from petrol ether:EtOAc (9:1) to afford the title compound as a solid (27 g, 87% yield). TLC: R$_f$=0.75 (Chloroform:MeOH; 9:1). $^1$H NMR (CDCl$_3$, 300 MHz) δ: 2.82 (3H, s), 3.32 (4H, m), 3.79 (4H, m), 6.68 (1H, d, J=9 Hz), 7.68 (1H, d, J=9 Hz), 8.42 (1H, s).

Intermediate B14: 1-(methylsulfonyl)-4-(4-phenoxyphenyl)piperazine

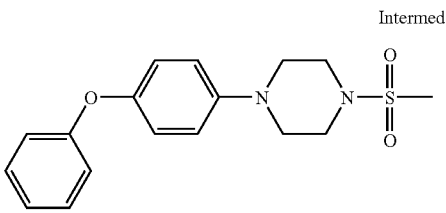
Intermediate B14

The title compound was prepared, following procedure described for Intermediate B1, but starting from 1-(4-phenoxyphenyl)piperazine (prepared as described by Kiritsy et al., 1978, in *Journal of Medicinal Chemistry*, 21(12), 1301-1307;

1.0 g; 3.93 mmol) as a beige powder (1.16 g, 89% yield). HPLC, Rt: 2.38 min (purity: 99.7%). LC/MS, M⁺(ESI): 333.1, M-(ESI): 331.2.

Intermediate B15: 4-(4-chlorophenyl)-1-(methylsulfonyl)piperidine

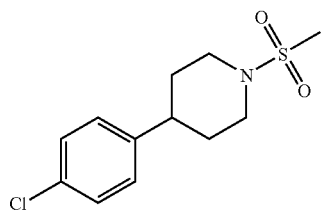

Intermediate B15

The title compound was prepared, following procedure described for Intermediate B1, but starting from 4-(4-chlorophenyl)piperidine (700 mg; 3.02 mmol), as a yellow powder (473 mg, 57% yield). HPLC, Rt: 3.80 min (purity: 97.5%). LC/MS, M⁺(ESI): 274.1.

Intermediate B16: 4-(4-methylphenyl)-1-(methylsulfonyl)piperidine

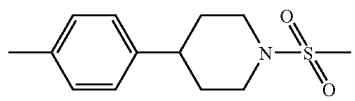

Intermediate B16

The title compound was prepared, following procedure described for Intermediate B1, but starting from 4-(4-methylphenyl)piperidine (700 mg; 3.02 mmol), as a white solid (769 mg, 53% yield). HPLC, Rt: 3.69 min (purity: 97.7%). LC/MS, M⁺(ESI): 254.1.

Intermediate B17: 1-(methylsulfonyl)-4-[5-(trifluoromethyl)pyridin-2-yl]-1,4-diazepane

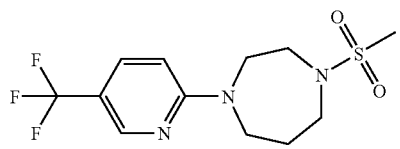

Intermediate B17

The title compound was prepared, following procedure described for Intermediate B1, but starting from 1-[5-(trifluoromethyl)pyrid-2-yl]-1,4-diazepane (500 mg; 2.04 mmol), as an off-white powder (472 mg, 72%). HPLC, Rt: 2.09 min (purity: 99.9%). ¹H NMR (CDCl₃, 300 MHz) δ: 8.39 (brs, 1H), 7.64 (dd, J=9.0, 2.2 Hz, 1H), 6.56 (d, J=9.0 Hz, 1H), 3.96 (t, J=5.2 Hz, 2H), 3.83 (t, J=6.4 Hz, 2H), 3.51 (t, J=5.2 Hz, 2H), 3.28 (t, J=6.3 Hz, 2H), 2.80 (s, 3H), 2.08 (m, 2H).

Intermediate B18: 1-(4-ethoxyphenyl)-4-(methylsulfonyl)piperazine

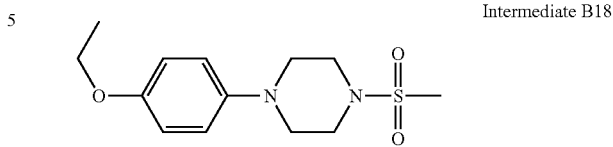

Intermediate B18

The title compound was prepared, following procedure described for Intermediate B1, but starting from 1-(4-ethoxyphenyl)piperazine (2.0 g, 9.7 mmol), as a beige powder (2.55 g, 92%). HPLC, Rt: 1.74 min (purity: 99.5%). LC/MS, M⁺(ESI): 285.1.

Intermediate B19: 1-(5-Bromopyridin-2-yl)-4-(methylsulfonyl)piperazine

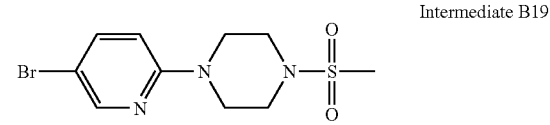

Intermediate B19

The title compound was prepared, following procedure described for Intermediate B1, but starting from 1-(5-bromopyridin-2-yl) piperazine (28 g, 0.116 mol), as a beige solid (29 g, 78%). ¹H NMR (CDCl₃) δ: 2.82 (3H, s), 3.33 (4H, t), 3.67 (4H, t), 6.59 (1H, d, J=9 Hz), 7.58-7.59 (1H, m), 8.22 (1H, d, J=2.4Hz).

Intermediate B20: 1-(1,3-benzodioxol-5-yl)-4-(methylsulfonyl)piperazine

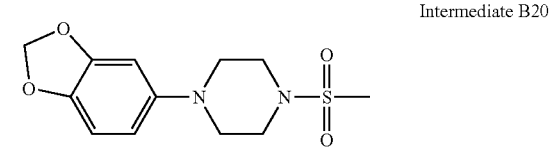

Intermediate B20

The title compound was prepared, following procedure described for Intermediate B1, but starting from 1-(1,3-benzodioxol-5-yl)piperazine (638 mg; 3.09 mmol) as a beige powder (527 mg, 60% yield). HPLC, Rt: 1.63 min (purity: 100%). LC/MS, M⁺(ESI): 285.1.

Intermediate B21: 1-(3,4-dimethoxyphenyl)-4-(methylsulfonyl)piperazine

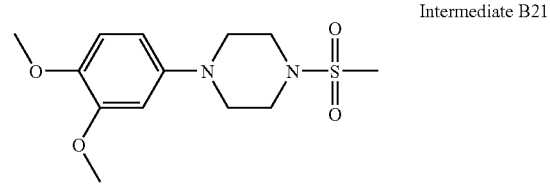

Intermediate B21

The title compound was prepared, following procedure described for Intermediate B1, but starting from 1-(3,4-dimethoxyphenyl)-piperazine hydrochloride (2.0 g; 7.73 mmol), as a white powder (1.89 g, 81% yield). HPLC, Rt: 1.58 min (purity: 99.6%). LC/MS, M+(ESI): 301.1.

Intermediate B22: 1-(4-ethoxyphenyl)-4-(methylsulfonyl)-1,4-diazepane

Step a) Formation of 1-(4-ethoxyphenyl)-1,4-diazepane dihydrochloride

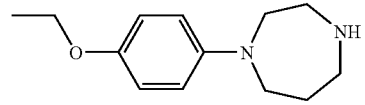

A solution of homopiperazine (2.74 g), 4-bromophenetole (5.0 g) and sodium tert-butoxide (3.6 g) was prepared in anhydrous toluene (50 ml). Argon was bubbled in the solution for 5 min, then Pd(OAc)$_2$ (280 mg) and (+/−)-BINAP (620 mg) were added and the reaction mixture was heated at reflux for 15 hrs. The reaction mixture was evaporated under reduced pressure to give a dark brown solid, which was taken up in DCM and adsorbed on silica. Purification by flash chromatography on silica (DCM/MeOH) gave the parent compound as a yellow oil. Precipitation in Et$_2$O of the dihydrochloride salt by addition of a 1M solution of HCl in Et$_2$O in excess gave 1.06 g (15%) of the title compound as a beige powder. LC/MS, M+(ESI): 221.2.

Step b) Formation of 1-(4-ethoxyphenyl)-4-(methylsulfonyl)-1,4-diazepane

Intermediate B22

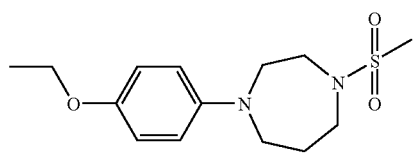

The title compound was prepared, following procedure described for Intermediate B1, but starting from 1-(4-ethoxyphenyl)-1,4-diazepane dihydrochloride (250 mg; 0.85 mmol), as a orange solid (141 mg, 55% yield). HPLC, Rt: 1.59 min (purity: 94.7%). LC/MS, M+(ESI): 299.2.

Intermediate B23: (2R)-4-(4-fluorophenyl)-2-methyl-1-(methylsulfonyl)piperazin

Step a) Formation of (3R)-1-(4-Fluorophenyl)-3-methylpiperazine

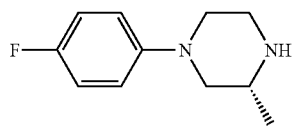

To a mixture of 1-bromo-4-fluorobenzene (5.0 g, 0.0285 mol), (R)-2-methylpiperazine (3.15 g, 0.0313 mol) and sodium-tert-butoxide (4 g, 0.042 mol) in dry toluene (100 mL) under nitrogen was added Pd(OAc)$_2$ (0.25 g, 0.0011 mol) followed by BINAP (0.75 g, 0.0012 mol). The reaction mixture was then refluxed for 18 h and cooled down to rt. The reaction mixture was washed with water, dried over magnesium sulfate, filtrated and concentrated. Purification of the crude by chromatography on silica (chloroform:MeOH, 8:2) gave the title compound as a liquid (2.5 g, 46% yield). TLC: R$_f$=0.25 (Chloroform/MeOH: 9/1).

Step b) Formation of (2R)-4-(4-fluorophenyl)-2-methyl-1-(methylsulfonyl)piperazine Intermediate B23

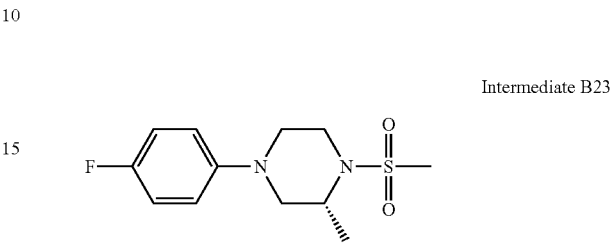

The title compound was prepared, following procedure described for Intermediate B1, but starting from 1-(4-fluorophenyl)-(3R)-methylpiperazine (500 mg; 2.57 mmol), as a yellow solid (458 mg, 65% yield). HPLC, Rt: 2.85 min (purity: 96.9%). LC/MS, M+(ESI): 273.1.

Example 1

3-(1,3-benzodioxol-5-yl)-1-({[4-(4-fluorophenyl)-1-piperazinyl]sulfonyl}methyl)-2-propynyl(hydroxy)formamide (1)

Step a) Formation of a mixture of 1-{[(1E)-4-(1,3-benzodioxol-5-yl)-1-buten-3-ynyl]sulfonyl}-4-(4-fluorophenyl)piperazine and 1-{[(1Z)-4-(1,3-benzodioxol-5-yl)-1-buten-3-ynyl]sulfonyl}-4-(4-fluorophenyl)piperazine

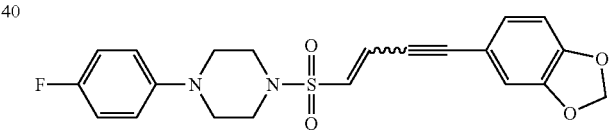

To a solution of 1-(4-fluorophenyl)-4-(methylsulfonyl)piperazine (Intermediate B1, 175 mg; 0.68 mmol) in THF (5 mL), lithium bis(trimethylsilyl)amide (1.49 mL; solution 1.00M in toluene; 1.49 mmol) was slowly added at −78° C. under inert atmosphere. The mixture was then stirred at −78° C. for 1 h. After this time, diethylchlorophosphate (98 μl; 0.68 mmol) was added and the mixture stirred at −78° C. for a further 1 hour. A solution of 3-(1,3-benzodioxol-5-yl)-2-propynal (Intermediate A1, 124 mg; 0.71 mmol) in THF (1 mL) was cannulated and the mixture was allowed to warm to room temperature and stirred for 18 h. Saturated aqueous ammonium chloride solution was added and the reaction mixture was extracted with EtOAc. Organic layer was washed with brine, dried over magnesium sulfate, filtrated and concentrated. Purification by flash chromatography on silica (EtOAc:c-Hex, 10:90 to 30:70) gave the title compounds (171 mg of the E isomer and 23 mg of the Z isomer, 69% total yield). E isomer: HPLC, Rt: 4.56 min (purity: 93.0%). LC/MS, M+(ESI): 415.2. $^1$H NMR (CDCl$_3$) δ: 6.79-7.00 (m, 6H), 6.78 (dd, J=11.5, 3.6 Hz, 2H), 6.53 (d, J=15.1 Hz, 1H), 5.99 (s, 2H), 3.45 (m, 4H), 3.19 (m, 4H); Z-isomer: HPLC, Rt: 4.33 min (purity: 96.6%). $^1$H NMR (CDCl$_3$) δ: 7.08 (dd, J=8.1, 1.5 Hz, 1H), 6.83-6.93 (m, 5H), 6.77 (d, J=8.1 Hz, 1H), 6.42 (AB, Δ=41 Hz, J=11 Hz, 2H), 5.98 (s, 2H), 3.43 (m, 4H), 3.16 (m, 4H).

Step b) Formation of N-[3-(1,3-benzodioxol-5-yl)-1-({[4-(4-fluorophenyl)-1-piperazinyl]sulfonyl}methyl)-2-propynyl]hydroxylamine

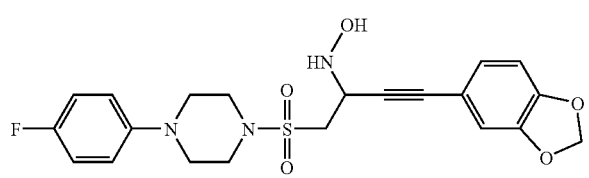

1-{[(1E)-4-(1,3-benzodioxol-5-yl)-1-buten-3-ynyl]sulfonyl}-4-(4-fluorophenyl)piperazine (171 mg; 0.41 mmol) was dissolved in THF (6 mL) and a 50% aqueous solution of hydroxylamine (0.70 mL; 11.87 mmol) was added. The mixture was stirred at 60° C. for 5 h. THF was removed under reduced pressure and the residue was dissolved in DCM and washed with brine. Organic layer was dried over magnesium sulfate, filtrated and concentrated to give 148 mg of a white foam. Purification by flash chromatography on silicagel (EtOAc:c-Hex, 50:50) gave the title compound as a white foam (150 mg, 81% yield). HPLC, Rt: 3.39 min (purity: 83.7%). LC/MS, M⁺ (ESI): 448.1. ¹H NMR (CDCl₃) δ: 6.85-6.94 (m, 6H), 6.41 (d, J=8.3 Hz, 1H), 5.95 (s, 2H), 4.49 (dd, J=7.8, 4.6 Hz, 1H), 3.63 (dd, J=14.1, 7.9 Hz, 1H), 3.66 (m, 4H), 3.30 (dd, J=14.1, 4.5 Hz, 1H), 3.16 (m, 4H).

Step c) Formation of 3-(1,3-benzodioxol-5-yl)-1-({[4-(4-fluorophenyl)-1-piperazinyl]sulfonyl}methyl)-2-propynyl(hydroxy)formamide (1)

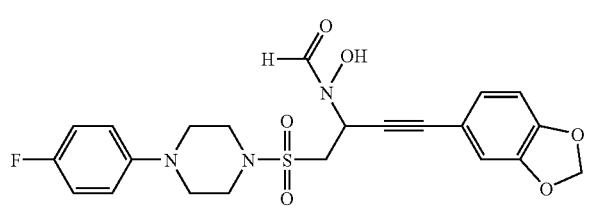

Acetic anhydride (1.00 mL; 10.59 mmol) was added dropwise to formic acid (5 mL) at 0° C. and the mixture was stirred for 30 min. 1 mL of this solution was then added to a solution of N-[3-(1,3-benzodioxol-5-yl)-1-({[4-(4-fluorophenyl)-1-piperazinyl]sulfonyl}methyl)-2-propynyl]hydroxylamine (150.0 mg; 0.34 mmol) in THF (3 mL) and formic acid (0.7 mL) and the mixture was stirred overnight. The reaction mixture was then evaporated to dryness, the residue dissolved in MeOH and heated at 60° C. for 3 h. The solution was allowed to cool down to rt and the precipitate obtained was filtered. It was redissolved in EtOAc and precipitated again in pentane, filtered and dried under reduced pressure to give the title compound (1) (80 mg, 50% yield) as a white solid. HPLC, Rt: 3.58 min (purity: 96.9%). LC/MS, M⁺(ESI): 476.3, M⁻(ESI): 474.3. ¹H NMR (CDCl₃) δ: 9.55 (s, 0.5H), 9.12 (s, 0.5H), 8.1 (m, 1H), 6.90-7.09 (m, 7H), 6.05 (s, 2H), 4.81 (s, 0.5H), 4.61 (s, 0.5H), 3.62 (m, 2H), 3.31 (m, 4H), 3.14 (m, 4H).

Example 2

1-({[4-(4-fluorophenyl)-1-piperazinyl]sulfonyl}methyl)-3-(trimethylsilyl)-2-propynyl(hydroxy)formamide (2)

Step a) Formation of a mixture of 1-(4-fluorophenyl)-4-{[(1E)-4-(trimethylsilyl)-1-buten-3-ynyl]sulfonyl}piperazine and 1-(4-fluorophenyl)-4-{[(1Z)-4-(trimethylsilyl)-1-buten-3-ynyl]sulfonyl}piperazine

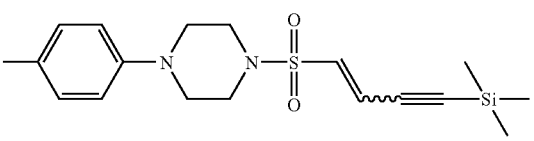

The title compound was prepared, following procedure described in Example 1, step a), but starting from 1-(4-fluorophenyl)-4-(methylsulfonyl) piperazine (Intermediate B1, 258 mg, 1.0 mmol, 1.0 eq.) and 3-trimethylsilylpropinal (132 mg, 1.05 mmol, 1.05 eq.) as a white powder. (240 mg, 65% yield). HPLC, Rt: 5.03 min (purity: 99.7%). LC/MS, M⁺(ESI): 367.1. ¹H NMR (CDCl₃) δ: 7.07-6.86 (m, 4H), 6.60 (m, 2H), 3.36 (m, 4H), 3.21 (m, 4H), 0.26 (s, 9H).

Step b) Formation of 1-(4-fluorophenyl)-4-{[2-(hydroxyamino)-4-(trimethylsilyl)-3-butynyl]sulfonyl}piperazine

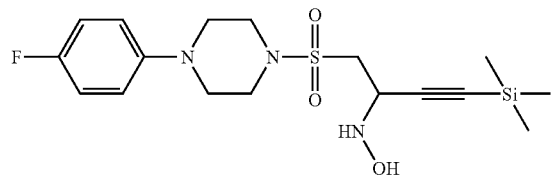

The title compound (2) was prepared, following procedure described in Example 1, step b), but starting from 1-(4-fluorophenyl)-4-{[(1E)-4-(trimethylsilyl)-1-buten-3-ynyl]sulfonyl}piperazine (240 mg, 0.65 mmol, 1.0 eq.), as a white powder. (161 mg, 62% yield). HPLC, Rt: 3.89 min (purity: 96.0%). LC/MS, M⁺(ESI): 400.1. ¹H NMR (CDCl₃) δ: 7.13-6.84 (m, 4H), 5.35 (brs, 2H), 4.35 dd (J: 4.35 Hz, J=8.23 Hz, 1H), 3.61 (m, 1H), 3.52 (m, 4H), 3.26 (m, 1H), 3.21 (m, 4H), 0.22 (s, 9H).

Step c) Formation of 1-({[4-(4-fluorophenyl)-1-piperazinyl]sulfonyl}methyl)-3-(trimethylsilyl)-2-propynyl(hydroxy)formamide (2)

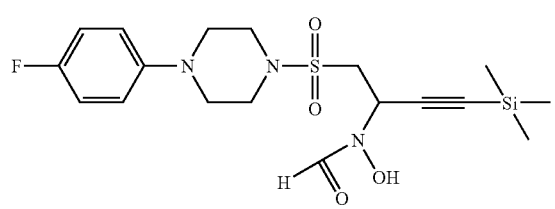

The title compound (2) was prepared, following procedure described in Example 1, step c), but starting from 1-(4-fluorophenyl)-4-{[2-(hydroxyamino)-4-(trimethylsilyl)-3-butynyl]sulfonyl}piperazine (40 mg, 0.1 mmol, 1.0 eq.) as a colorless oil. HPLC, Rt: 3.80 min (purity: 61.3%). LC/MS, M⁺(ESI): 428.0.

Example 3 hydroxy[1-({[4-(2-pyridinyl)-1-piperazinyl]sulfonyl}methyl)-3-(trimethyl silyl)-2-propynyl]formamide (3)

Step a) Formation of a mixture of 1-(2-pyridinyl)-4-{[(1E)-4-(trimethylsilyl)-1-buten-3-ynyl]sulfonyl}piperazine and 1-(2-pyridinyl)-4-{[(1Z)-4-(trimethylsilyl)-1-buten-3-ynyl]sulfonyl}piperazine

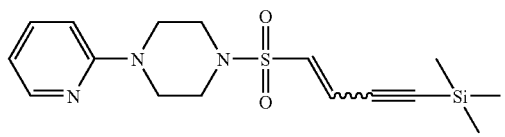

The title compound was prepared, following procedure described in Example 1, step a), but starting from 1-(methylsulfonyl)-4-(2-pyridinyl)piperazine (Intermediate B2, 1291 mg, 5.0 mmol, 1.0 eq.) and 3-trimethylsilylpropinal (1325 mg, 10.5 mmol, 1.05 eq.) as a brownish powder. (1901 mg, 54% yield). HPLC, Rt: 3.11 min (purity: 97.6%). LC/MS, M⁺(ESI): 350.2. ¹H NMR (CDCl₃) δ: 8.23 (m, 1H), 7.54 (m, 1H), 6.76-6.62 (m, 2H), 6.61-6.55 (m, 2H), 3.75-3.65 (m, 4H), 3.35-3.36 (m, 4H), 0.25 (s, 9H).

Step b) Formation of 1-{[2-(hydroxyamino)-4-(trimethylsilyl)-3-butynyl]sulfonyl}-4-(2-pyridinyl)piperazine

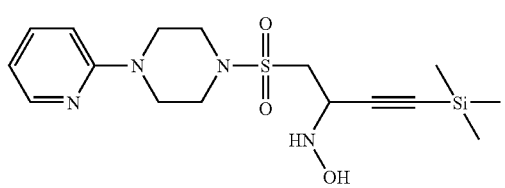

The title compound was prepared, following procedure described in Example 1, step b), but starting from 1-(2-pyridinyl)-4-{[(1E)-4-(trimethylsilyl)-1-buten-3-ynyl]sulfonyl}piperazine (349 mg, 1.0 mmol, 1.0 eq.) as a colorless oil. (306 mg, 80% yield). HPLC, Rt: 2.08 min (purity: 94.8%). LC/MS, M⁺(ESI): 383.3. ¹H NMR (CDCl₃) δ: 8.22 (m, 1H), 7.52 (m, 1H), 6.76 (brs, 1H), 6.66 (m, 2H), 5.62 (brs, 1H), 4.35-4.22 (m, 1H), 3.73-3.52 (m, 5H), 3.49-3.34 (m, 4H), 3.29-3.15 (m, 1H), 0.16 (s, 9H).

Step c) Formation of hydroxy[1-({[4-(2-pyridinyl)-1-piperazinyl]sulfonyl}methyl)-3-(trimethylsilyl)-2-propynyl]formamide

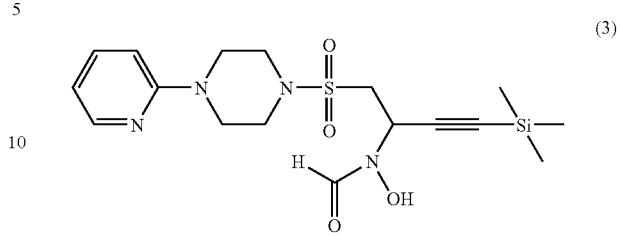

The title compound (3) was prepared, following procedure described in Example 1, step c), but starting from 1-{[2-(hydroxyamino)-4-(trimethylsilyl)-3-butynyl]sulfonyl}-4-(2-pyridinyl)piperazine (650 mg, 1.61 mmol, 1.0 eq.) as a white powder. (192 mg, 57% yield). HPLC, Rt: 2.33 min (purity: 98.2%). LC/MS, M⁺(ESI): 411.2.

Example 4

1-({[4-(4-fluorophenyl)-1-piperazinyl]sulfonyl}methyl)-3-phenyl-2-propynyl(hydroxy)formamide (4)

Step a) Formation of a mixture of 1-(4-fluorophenyl)-4-{[(1E)-4-phenyl-1-buten-3-ynyl]sulfonyl}piperazine and 1-(4-fluorophenyl)-4-{[(1Z)-4-phenyl-1-buten-3-ynyl]sulfonyl}piperazine

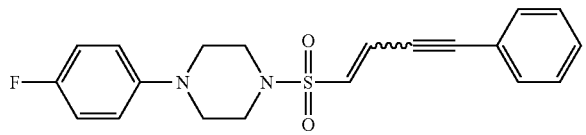

The title compound was prepared, following procedure described in Example 1, step a), but starting from 1-(4-fluorophenyl)-4-(methylsulfonyl)piperazine (Intermediate B1, 1291 mg, 5.0 mmol, 1.0 eq.) and phenylpropioaldehyde (683 mg, 5.25 mmol, 1.05 eq.), as a white powder. (820 mg, 44% yield). HPLC, Rt: 4.71 min (purity: 98.9%). LC/MS, M⁺(ESI): 371.1. ¹H NMR (CDCl₃) δ: 7.35-7.08 (m, 5H), 6.83-6.53 (m, 5H), 6.38 (d, J=15.1 Hz, 1H), 3.15 (m, 4H), 2.97 (m, 4H).

Step b) Formation of 1-(4-fluorophenyl)-4-{[2-(hydroxyamino)-4-phenyl-3-butynyl]sulfonyl}piperazine

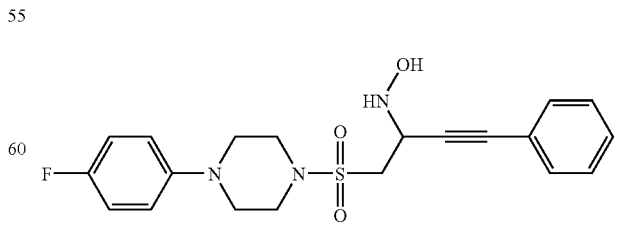

The title compound was prepared, following procedure described in Example 1, step b), but starting from 1-(4-fluorophenyl)-4-{[(1E)-4-phenyl-1-buten-3-ynyl]

sulfonyl}piperazine (800 mg, 2.16 mmol, 1.0 eq.) as a white powder. (665 mg, 76% yield). HPLC, Rt: 3.51 min (purity: 98.8%). LC/MS, M⁺(ESI): 404.1. ¹H NMR (CDCl₃) δ: 7.62-7.51 (m, 2H), 7.50-7.31 (m, 3H), 7.16-6.90 (m, 4H), 5.81 (brs, 1H), 5.06 (brs, 1H), 4.65 (dd, J=4.5 Hz, J=7.9 Hz, 1H), 3.77 (dd, J=17.7 Hz, J=13.9 Hz, 1H), 3.62 (m, 4H), 3.45 (dd, J=4.5 Hz, J=14.2 Hz, 1H), 3.30 (m, 4H).

Step c) Formation of 1-({[4-(4-fluorophenyl)-1-piperazinyl]sulfonyl}methyl)-3-phenyl-2-propynyl(hydroxy)formamide (4)

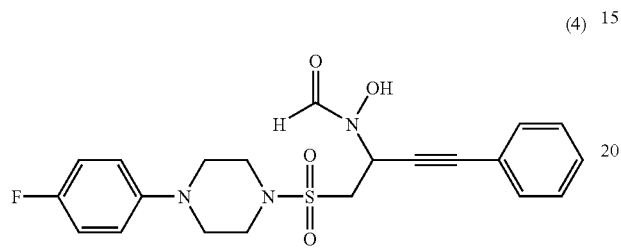

The title compound (4) was prepared, following procedure described in Example 1, step c), but starting from 1-(4-fluorophenyl)-4-{[2-(hydroxyamino)-4-phenyl-3-butynyl]sulfonyl}piperazine (650 mg, 1.61 mmol, 1.0 eq.), as a white powder. (512 mg, 74% yield). HPLC, Rt: 3.71 min (purity: 98.9%). LC/MS, M⁺(ESI): 432.2, M⁻(ESI): 430.0. ¹H NMR (CDCl₃) δ: 8.27 (brs, 0.35H), 7.97 (brs, 0.65H), 7.29-7.20 (m, 2H), 7.19-7.06 (m, 3H), 6.87-6.61 (m, 4H), 5.60 (brs, 0.45H), 5.08 (brs, 0.55H), 3.75-3.41 (m, 1H), 3.27 (m, 4H), 2.96 (m, 4H).

Examples 4a, 4b

[(1S)-1-({[4-(4-fluorophenyl)piperazin-1-yl]sulfonyl}methyl)-3-phenylprop-2-yn-1-yl]hydroxyformamide (4a) and [(1R)-1-({[4-(4-fluorophenyl)piperazin-1-yl]sulfonyl}methyl)-3-phenylprop-2-yn-1-yl]hydroxyformamide (4b)

(4a)

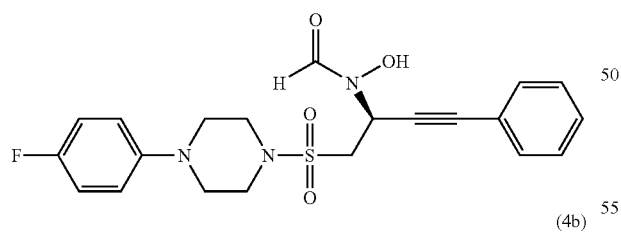

(4b)

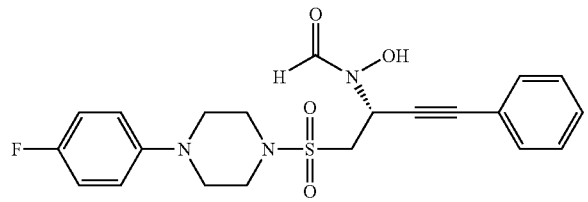

The two enantiomers of 1-({[4-(4-fluorophenyl)-1-piperazinyl]sulfonyl}methyl)-3-phenyl-2-propynyl(hydroxy)formamide (prepared as in Example 4) were separated by chiral HPLC using a semi-prep CHIRALPACK AD column (MeOH:i-PrOH:FA, 50:50:0.1, flow=10 mL/min). First compound (presumably R enantiomer): HPLC, Rt: 3.67 min (purity: 98.9%). LC/MS, M⁺(ESI): 432.2, M⁻(ESI): 430.0; chiral HPLC (CHIRALPACK AD-H), Rt=9.17 min (hexane:EtOH:DEA, 50:50: 0.1, flow=1 mL/min). Second compound (presumably S enantiomer): HPLC, Rt: 3.61 min (purity: 95.5%). LC/MS, M⁺(ESI): 432.2, M⁻(ESI): 430.2; chiral HPLC (CHIRALPACK AD-H), Rt=12.8 min (hexane:EtOH:DEA, 50:50: 0.1, flow=1 mL/min).

Example 5

1-[({4-[4-(benzyloxy)phenyl]-1-piperazinyl}sulfonyl)methyl]-2-octynyl(hydroxy)formamide (5)

Step a) Formation of a mixture of benzyl 4-{4-[(1E)-1-nonen-3-ynylsulfonyl]-1-piperazinyl}phenyl ether and benzyl 4-{4-[(1Z)-1-nonen-3-ynylsulfonyl]-1-piperazinyl}phenyl ether

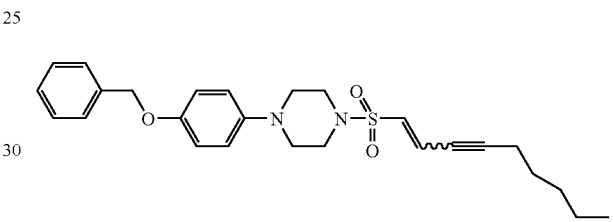

The title compound was prepared, following procedure described in Example 1, step a), but starting from 1-[4-(benzyloxy)phenyl]-4-(methylsulfonyl)piperazine (Intermediate B3, 346 mg, 1.0 mmol, 1.0 eq.) and 2-octynal (130 mg, 1.05 mmol, 1.05 eq.), as a white solid (238 mg, 55% yield). HPLC, Rt: 5.27 min (purity: 84.9%). LC/MS, M⁺(ESI): 453.4. ¹H NMR (CDCl₃) δ: 7.48-7.28 (m, 5H), 6.95-6.83 (m, 4H), 6.61 (m, 0.35H), 6.56 (m, 0.65H), 6.45 (s, 0.65H), 6.41 (s, 0.35H), 5.01 (s, 2H), 3.30 (m, 4H), 3.13 (m, 4H), 2.37 (m, 2H), 1.56 (m, 2H), 1.45-1.15 (m, 6H), 0.90 (m, 3H).

Step b) Formation of 1-[4-(benzyloxy)phenyl]-4-{[2-(hydroxyamino)-3-nonynyl]sulfonyl}piperazine

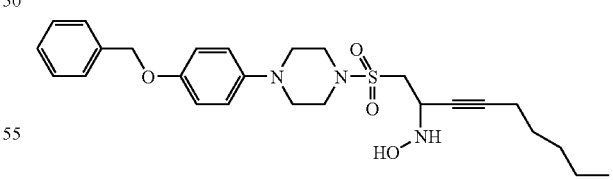

The title compound was prepared, following procedure described in Example 1, step b), but starting from benzyl 4-{4-[(1E)-1-nonen-3-ynylsulfonyl]-1-piperazinyl}phenyl ether (238 mg, 0.53 mmol, 1 eq.) as a white solid (211 mg, 83% yield). HPLC, Rt: 3.89 min (purity: 60.6%). LC/MS, M⁺(ESI): 486.3. ¹H NMR (CDCl₃) δ: 7.44-7.27 (m, 5H), 6.95-6.83 (m, 4H), 5.36 (brs, 1H), 5.02 (s, 2H), 4.28 (m, 1H), 3.60-3.43 (m, 5H), 3.16 (m, 5H), 2.20 (m, 2H), 1.50 (m, 2H), 1.45-1.24 (m, 4H), 0.89 (m, 3H).

Step c) Formation of 1-[({4-[4-(benzyloxy)phenyl]-1-piperazinyl}sulfonyl)methyl]-2-octynyl(hydroxy)formamide

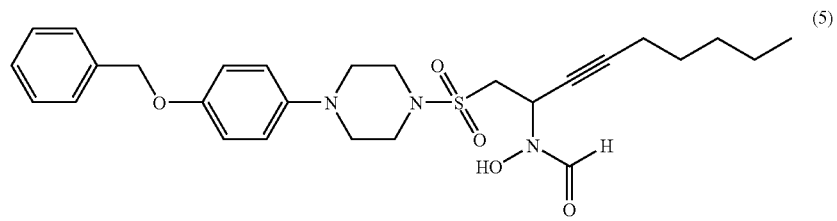
(5)

The title compound (5) was prepared, following procedure described in Example 1, step c), but starting from 1-[4-(benzyloxy)phenyl]-4-{[2-(hydroxyamino)-3-nonynyl]sulfonyl}piperazine (160 mg, 0.33 mmol, 1.0 eq.) as a pink solid. (70 mg, 41% yield). HPLC, Rt: 4.15 min (purity: 93.8%). LC/MS, M$^+$(ESI): 514.4, M$^-$(ESI): 512.2. $^1$H NMR (CDCl$_3$) δ: 8.41 (brs, 0.37H), 8.11 (brs, 0.63H), 7.45-7.27 (m, 5H), 6.96-6.83 (m, 4H), 5.55 (brs, 0.5H), 5.00 (brs, 2.5H), 3.80-3.56 (m, 1H), 3.41 (m, 3H), 3.23-3.18 (m, 1H), 3.11 (m, 4H), 2.19 (m, 2H), 165-1.43 (m, 4H), 1.40-1.24 (m, 4H), 0.88 (m, 3H).

Example 6

1-({[4-(4-fluorophenyl)-1-piperazinyl]sulfonyl}methyl)-4-phenyl-2-butynyl (hydroxy)formamide (6)

Step a) Formation of a mixture of 1-(4-fluorophenyl)-4-{[(1E)-5-phenyl-1-penten-3-ynyl]sulfonyl}piperazine and 1-(4-fluorophenyl)-4-{[(1Z)-5-phenyl-1-penten-3-ynyl]sulfonyl}piperazine

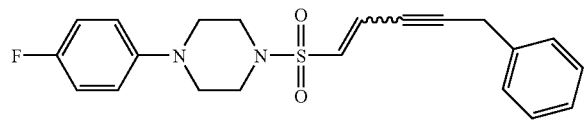

To a solution of 1-(4-fluorophenyl)-4-(methylsulfonyl)piperazine (Intermediate B1, 107.5 mg; 0.42 mmol) in THF (10 mL) was added lithiumbis(trimethylsilyl)amide (0.92 mL; 1 M solution in toluene; 0.92 mmol) at −78° C. under nitrogen atmosphere. The mixture was stirred at −78° C. for 30 min. Diethylchlorophosphonate (60 μl; 0.42 mmol) was then added and the mixture stirred at −78° C. for an additional 30 min. A solution of 4-phenyl-2-butynal (Intermediate A2, 60 mg; 0.42 mmol) in THF (3 mL) was then cannulated and the mixture was stirred at −78° C. for 1.5 h. The mixture was then quenched with saturated NH$_4$Cl solution and extracted with EtOAc. Organic layer was washed with brine, dried over magnesium sulfate, filtrated and concentrated. Purification of the crude (190 mg) by flash chromatography on silica (EtOAc/c-Hex 10-90 then 20:80) gave the title compounds (133 mg of the E isomer and 28 mg of the Z isomer, 98% total yield). E-isomer: HPLC, Rt: 4.68 min (purity: 94.6%). LC/MS, M$^+$(ESI): 385.2, M$^-$(ESI): 383.2. $^1$H NMR (CDCl$_3$) δ: 7.30 (m, 5H), 6.81-6.89 (m, 4H), 6.63 (dt, J=15.3, 2.2 Hz, 1H), 6.48 (d, J=15.3 Hz, 1H), 3.78 (d, J=2.1 Hz, 2H), 3.31 (m, 4H), 3.15 (m, 4H); Z-isomer: HPLC, Rt: 4.41 min (purity: 76%). LC/MS, M$^+$(ESI): 385.2, M$^-$ (ESI): 383.2. $^1$H NMR (CDCl$_3$) δ: 7.35 (m, 5H), 6.99 (m, 4H), 6.36 (d, J=3.0 Hz, 2H), 3.84 (s, 2H), 3.42 (m, 4H), 3.13 (m, 4H).

Step b) Formation of 1-(4-fluorophenyl)-4-{[2-(hydroxyamino)-5-phenyl-3-pentynyl]sulfonyl}piperazine

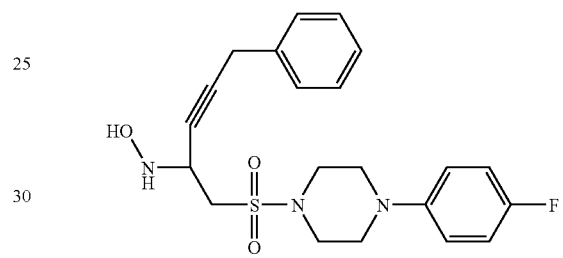

To a solution of 1-(4-fluorophenyl)-4-{[(1E)-5-phenyl-1-penten-3-ynyl]sulfonyl}piperazine (155 mg; 0.40 mmol) in THF (8 mL) was added hydroxylamine (0.71 mL; 12.1 mmol). The reaction mixture was heated at 60° C. for 1 h. It was then diluted with EtOAc, washed with brine, dried over magnesium sulfate, filtrated and concentrated. Purification of the crude (135 mg) by flash chromatography on silica gave the title compound (50 mg, 30% yield). HPLC, Rt: 3.84 min (purity: 94.5%). LC/MS, M$^+$(ESI): 418.3, M$^-$(ESI): 416.2. $^1$H NMR (CDCl$_3$) δ: 7.22-7.31 (m, 5H), 7.01 (m, 4H), 4.33 (m, 1H), 3.62 (d, J=1.9 Hz, 2H), 3.53-3.60 (m, 5H), 3.20-3.27 (m, 5H). $^1$H NMR (CDCl$_3$) δ: 7.30 (m, 5H), 6.95 (m, 4H), 6.32 (d, J=15.6 Hz, 1H), 6.07 (dt, J=16.1, 7.4 Hz, 1H), 3.90 (s, 2H), 3.78 (d, J=6.6 Hz, 2H), 3.22 (m, 4H), 2.91 (m, 4H).

Step d) Formation of 1-({[4-(4-fluorophenyl)-1-piperazinyl]sulfonyl}methyl)-4-phenyl-2-butynyl(hydroxy)formamide

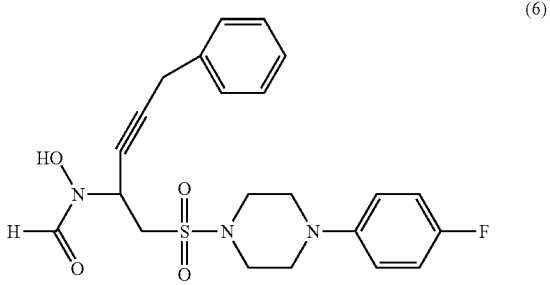
(6)

The title compound (6) was prepared following procedure described in Example 1, step d), but starting from 1-(4-fluorophenyl)-4-{[2-(hydroxyamino)-5-phenyl-3-pentynyl]sulfonyl}piperazine (50 mg, 0.12 mmol), as a yellow oil (40 mg, 75% yield). HPLC, Rt: 3.72 min (purity: 85.2%). LC/MS, M⁺(ESI): 446.3, M⁻(ESI): 444.2. ¹H NMR (CDCl₃) δ: 8.44 (brs, 0.4H), 8.10 (brs, 0.6H), 7.36-7.20 (m, 5H), 7.05-6.85 (m, 4H), 5.62 (brs, 0.5H), 5.10 (brs, 0.5H), 3.62 (s, 2H), 3.55-3.25 (m, 5H), 3.15 (brs, 5H).

Example 7

1-({[4-(4-fluorophenyl)-1-piperazinyl]sulfonyl}methyl)-2-octynyl(hydroxy)formamide (7)

Step a) Formation of a mixture of 1-(4-fluorophenyl)-4-[(1E)-1-nonen-3-ynylsulfonyl]piperazine and 1-(4-fluorophenyl)-4-[(1Z)-1-nonen-3-ynylsulfonyl]piperazine

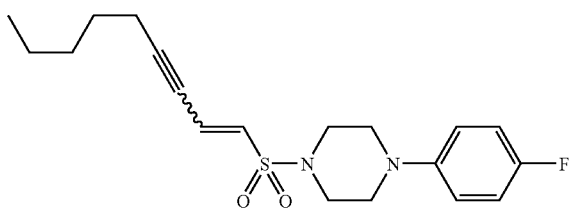

The title compound was prepared, following procedure described in Example 1, step a), but starting from 1-(4-fluorophenyl)-4-(methylsulfonyl)piperazine (Intermediate B1, 258 mg, 1.0 mmol) and 2-octynal (130 mg, 1.05 mmol), as a orange solid. (261 mg, 72% yield). HPLC, Rt: 5.17 min (purity: 99.9%). LC/MS, M⁺(ESI): 365.3, M⁻(ESI): 363.2. ¹H NMR (CDCl₃) δ: 7.04-6.86 (m, 4H), 6.63 (m, 0.35H), 6.56 (m, 0.65H), 6.45 (s, 0.65H), 6.40 (s, 0.35H), 3.35 (m, 4H), 3.18 (m, 4H), 2.37 (m, 2H), 1.53 (m, 4H), 1.45-1.15 (m, 4H), 0.90 (m, 3H).

Step b) Formation of 1-(4-fluorophenyl)-4-{[2-(hydroxyamino)-3-nonynyl]sulfonyl}piperazine

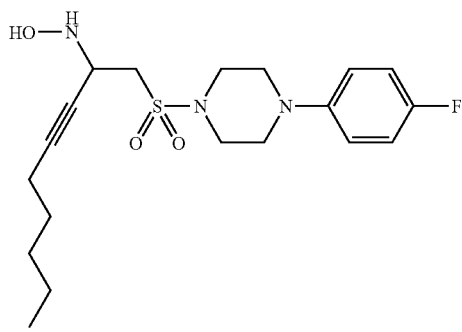

The title compound was prepared, following procedure described in Example 1, step b), but starting from benzyl 1-(4-fluorophenyl)-4-[(1E)-1-nonen-3-ynylsulfonyl]piperazine (264 mg, 0.72 mmol, 1.0 eq.), as a white solid. (169 mg, 69% yield). HPLC, Rt: 3.54 min (purity: 73.7%). LC/MS, M⁺(ESI): 398.2, M⁻(ESI): 396.2. ¹H NMR (CDCl₃) δ: 6.97 (m, 2H), 6.87 (m, 2H), 4.29 (m, 1H), 3.52-3.43 (m, 1H), 3.40 (m, 4H), 3.16 (m, 1H), 3.11 (m, 4H), 2.19 (m, 2H), 1.50 (m, 2H), 1.40-1.22 (m, 4H), 0.88 (m, 3H).

Step c) Formation of 1-({[4-(4-fluorophenyl)-1-piperazinyl]sulfonyl}methyl)-2-octynyl(hydroxy)formamide

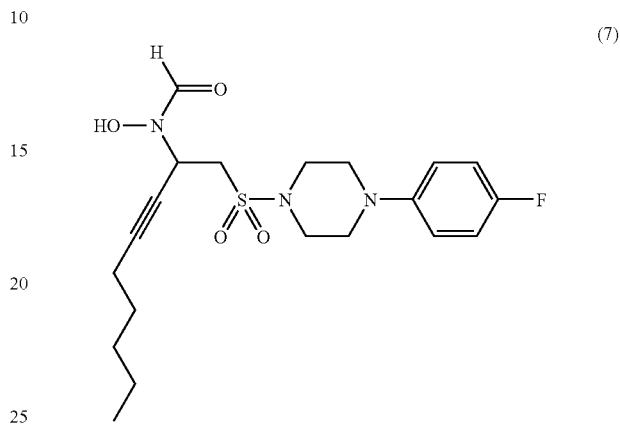

The title compound (7) was prepared, following procedure described in Example 1, step c), but starting from 1-({[4-(4-fluorophenyl)-1-piperazinyl]sulfonyl}methyl)-2-octynyl(hydroxy)formamide (162 mg, 0.41 mmol, 1.0 eq.), as an orange solid. (110 mg, 63% yield). HPLC, Rt: 3.87 min (purity: 99.2%). LC/MS, M⁺(ESI): 426.3, M⁻(ESI): 424.2. ¹H NMR (CDCl₃) δ: 8.41 (brs, 0.4H), 8.08 (brs, 0.6H), 6.97 (m, 2H), 6.88 (m, 2H), 5.55 (brs, 0.36H), 5.01 (brs, 0.64H), 3.82-3.55 (m, 1H), 3.42 (m, 4H), 3.27-3.20 (m, 1H), 3.14 (m, 4H), 2.18 (m, 2H), 1.50 (m, 2H), 1.40-1.20 (m, 4H), 0.89 (m, 3H).

Example 8

1-({[4-(4-fluorophenyl)-1-piperazinyl]sulfonyl}methyl)-3-(3-pyridinyl)-2-propynyl(hydroxy)formamide (8)

Step a) Formation of a mixture of 1-(4-fluorophenyl)-4-{[(1E)-4-(3-pyridinyl)-1-buten-3-ynyl]sulfonyl}piperazine and 1-(4-fluorophenyl)-4-{[(1Z)-4-(3-pyridinyl)-1-buten-3-ynyl]sulfonyl}piperazine

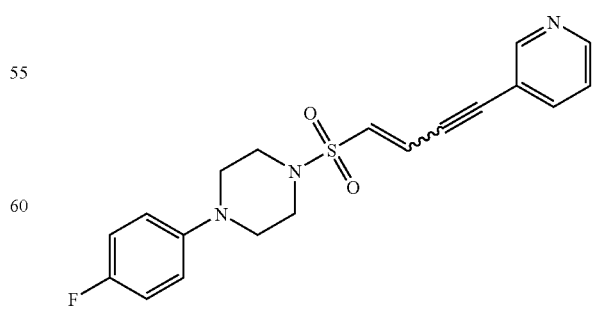

The title compound was prepared, following procedure described in Example 1, step a), but starting from 1-(4-fluorophenyl)-4-(methylsulfonyl)piperazine (Intermediate B1, 75 mg, 0.29 mmol) and 3-(3-pyridinyl)-2-propynal (Intermediate A3, 40 mg, 0.30 mmol), as a pale yellow powder (40 mg, 37% yield). HPLC, Rt: 3.1 min (purity: 94.7%). LC/MS, M⁺(ESI): 372.2, M⁻(ESI): 370.0. ¹H NMR (CDCl₃) δ: 8.72 (m, 1H), 8.61 (m, 1H), 7.78 (m, 1H), 7.31 (dd, J=7.9, 4.9 Hz, 1H), 7.04-6.94 (m, 2H), 6.93-6.83 (m, 2H), 6.84 (d, J=15.5 Hz, 1H), 6.68 (d, J=15.5 Hz, 1H), 3.37 (m, 4H), 3.18 (m, 4H).

Step b) Formation of 1-(4-fluorophenyl)-4-{[2-(hydroxyamino)-4-(3-pyridinyl)-3-butynyl]sulfonyl}piperazine

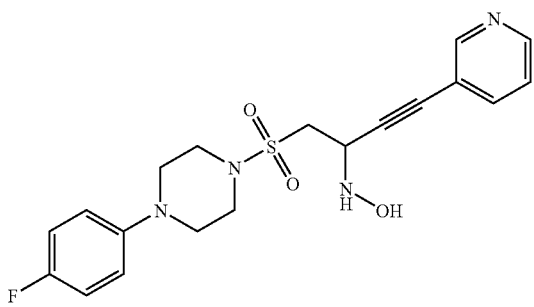

The title compound was prepared, following procedure described in Example 1, step b), but starting from 1-(4-fluorophenyl)-4-{[(1E)-4-(3-pyridinyl)-1-buten-3-ynyl]sulfonyl}piperazine (36 mg, 0.1 mmol), as a pale yellow powder (15 mg, 38% yield). HPLC, Rt: 1.9 min (purity: 94.7%). LC/MS, M⁺(ESI): 405.2.

Step c) Formation of 1-({[4-(4-fluorophenyl)-1-piperazinyl]sulfonyl}methyl)-3-(3-pyridinyl)-2-propynyl(hydroxy)formamide (8)

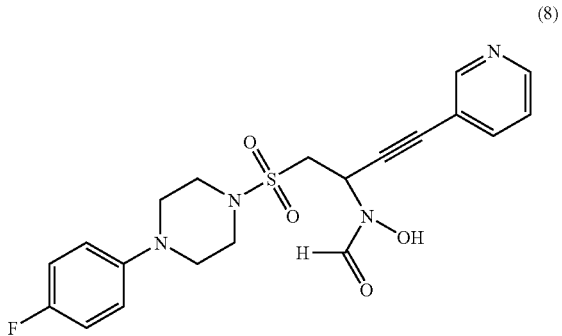

The title compound (8) was prepared, following procedure described in Example 1, step c), but starting from 1-(4-fluorophenyl)-4-{[2-(hydroxyamino)-4-(3-pyridinyl)-3-butynyl]sulfonyl}piperazine (15 mg, 0.04 mmol) as a pale yellow powder (6.4 mg, 40% yield). HPLC, Rt: 2.1 min (purity: 99.0%). LC/MS, M⁺(ESI): 433.3, M⁻(ESI): 431.1. ¹H NMR (CDCl₃) δ: 8.66-8.44 (m, 2.6H), 8.15 (brs, 0.4H), 7.78 (d, J=7.5 Hz, 1H), 7.32 (m, 1H), 7.05-6.86 (m, 4H), 5.91 (brs, 0.6H), 5.31 (brs, 0.4H), 3.95-3.65 (m, 1H), 3.60-3.37 (m, 6H), 3.20 (m, 4H).

Example 9 hydroxy[1-({[4-(4-methoxyphenyl)-1-piperazinyl]sulfonyl}methyl)-3-(3-pyridinyl)-2-propynyl]formamide (9)

Step a) Formation of a mixture of 1-(4-methoxyphenyl)-4-{[(1E)-4-(3-pyridinyl)-1-buten-3-ynyl]sulfonyl}piperazine and 1-(4-methoxyphenyl)-4-{[(1Z)-4-(3-pyridinyl)-1-buten-3-ynyl]sulfonyl}piperazine

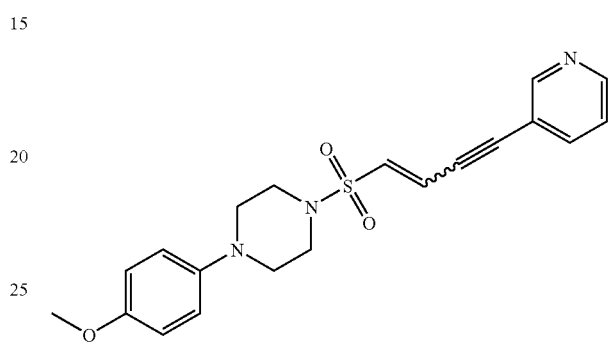

The title compound was prepared, following procedure described in Example 1, step a), but starting from 1-(4-methoxyphenyl)-4-(methylsulfonyl)piperazine (Intermediate B4, 338 mg, 1.25 mmol) and 3-(3-pyridinyl)-2-propynal (Intermediate A3, 246 mg, 1.88 mmol), as a yellow powder (31 mg, 6.5% yield). HPLC, Rt: 2.4 min (purity: 88.1%). LC/MS, M⁺(ESI): 384.2. ¹H NMR (CDCl₃) δ: 8.72 (m, 1H), 8.61 (m, 1H), 7.77 (m, 1H), 7.31 (m, 1H), 7.04-6.85 (m, 4H), 6.81 (d, J=15.4 Hz, 1H), 6.67 (d, J=15.4 Hz, 1H), 3.77 (s, 3H), 3.39 (m, 4H), 3.17 (m, 4H).

Step b) Formation of 1-{[2-(hydroxyamino)-4-(3-pyridinyl)-3-butynyl]sulfonyl}-4-(4-methoxyphenyl)piperazine

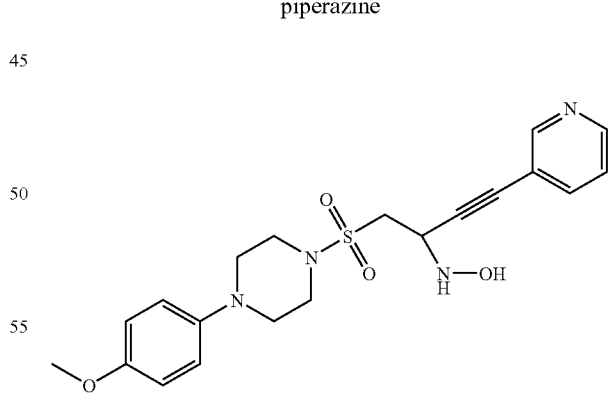

The title compound was prepared, following procedure described in Example 1, step b), but starting from 1-(4-methoxyphenyl)-4-{[(1E)-4-(3-pyridinyl)-1-buten-3-ynyl]sulfonyl}piperazine (27 mg, 0.07 mmol), as a white powder (15 mg, 51% yield). HPLC, Rt: 1.5 min (purity: 97.1%). LC/MS, M⁺(ESI): 417.3. ¹H NMR (CDCl₃) δ: 8.71 (brs, 1H), 8.55 (brd, J=4.7 Hz, 1H), 7.75 (brd, J=7.9 Hz, 1H), 7.26 (dd, J=7.9, 4.7 Hz, 1H), 6.93 (m, 2H), 6.85 (m, 2H), 4.58 (dd, J=8.2, 4.4 Hz, 1H), 3.78 (s, 3H), 3.70 (dd, J=14.2, 8.2 Hz, 1H), 3.52 (m, 4H), 3.34 (dd, J=14.2, 4.4 Hz, 1H), 3.17 (m, 4H).

Step c) Formation of hydroxy[1-({[4-(4-methoxyphenyl)-1-piperazinyl]sulfonyl}methyl)-3-(3-pyridinyl)-2-propynyl]formamide

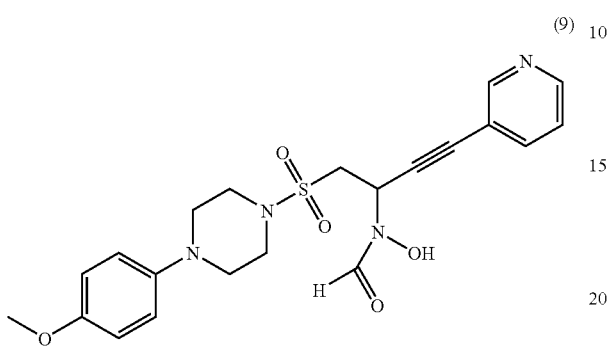

(9)

The title compound (9) was prepared, following procedure described in Example 1, step c), but starting from 1-{[2-(hydroxyamino)-4-(3-pyridinyl)-3-butynyl]sulfonyl}-4-(4-methoxy phenyl)piperazine (15 mg, 0.04 mmol), as a pale yellow powder (11 mg, 70% yield). HPLC, Rt: 1.6 min (purity: 99.2%). LC/MS, M+(ESI): 445.3, M−(ESI): 443.2. ¹H NMR (CDCl₃) δ: 8.64 (brs, 1H), 8.60-8.44 (m, 1.6H), 8.15 (brs, 0.4H), 7.76 (d, J=7.9 Hz, 1H), 7.30 (m, 1H), 6.93 (m, 2H), 6.83 (m, 2H), 5.93 (brs, 0.6H), 5.13 (brs, 0.4H), 4.00-3.65 (m, 1H), 3.76 (s, 3H), 3.49 (m, 6H), 3.16 (m, 4H).

Example 10 hydroxy[3-(3-methoxyphenyl)-1-({[4-(4-methoxyphenyl)-1-piperazinyl]sulfonyl}methyl)-2-propynyl]formamide (10)

Step a) Formation of diethyl {[4-(4-methoxyphenyl)-1-piperazinyl]sulfonyl}methyl phosphonate

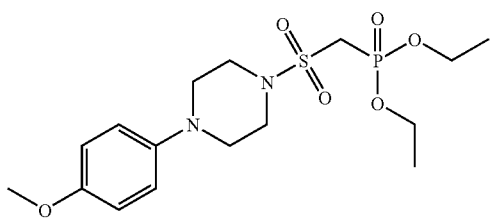

To a solution of 1-(4-methoxyphenyl)-4-(methylsulfonyl)piperazine (Intermediate B4, 338 mg; 1.25 mmol) in anhydrous THF (10 mL) was added a 1M solution of lithiumbis (trimethylsilyl)amide in toluene (2.75 mL, 2.75 mmol) at −20° C. under inert atmosphere. The resulting mixture was stirred at −20° C. for 30 min. Then diethylchlorophosphate (180 µl; 1.25 mmol) was added and the mixture stirred at −20° C. for 4 additional hours. A saturated aqueous solution of NH₄Cl was added and the reaction mixture was extracted with EtOAc (2×). The organic layers were washed with a saturated aqueous solution of NaHCO₃. The combined organic layers were dried (MgSO₄) and the solvents were removed under reduced pressure. Purification by flash chromatography on silica (cHex:EtOAc, gradient 80:20 to 0:100) gave 255 mg (50%) of the title compound as a yellow powder. HPLC, Rt: 2.22 min (purity: 99.8%). LC/MS, M+(ESI): 407.3, M−(ESI): 405.2. ¹H NMR (CDCl₃) δ: 6.87 (m, 4H), 4.26 (m, 4H), 3.78 (s, 3H), 3.59 (s, 1H), 3.53 (s, 1H), 3.50 (m, 4H), 3.16 (m, 4H), 1.39 (t, J=7.0 Hz, 6H).

Step b) Formation of a mixture of 1-(4-methoxyphenyl)-4-{[(1E)-4-(3-methoxyphenyl)-1-buten-3-ynyl]sulfonyl}piperazine and 1-(4-methoxyphenyl)-4-{[(1Z)-4-(3-methoxyphenyl)-1-buten-3-ynyl]sulfonyl}piperazine

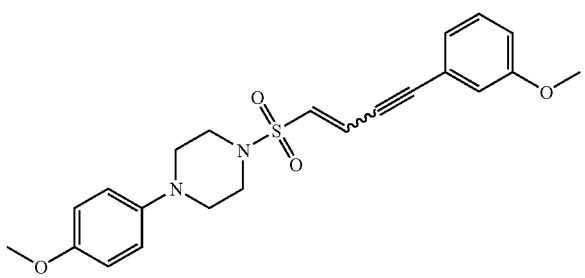

To a solution of {[4-(4-methoxyphenyl)-1-piperazinyl]sulfonyl}methylphosphonate (250 mg, 0.62 mmol) in anhydrous THF (5 mL) was added a 1M solution of lithiumbis (trimethylsilyl)amide in toluene (0.74 mL, 0.74 mmol) at −10° C. under inert atmosphere. After 15 min, a solution of 3-(3-methoxyphenyl)-2-propynal (117 mg, 0.74 mmol, Intermediate A5) in anhydrous THF (0.7 mL) was added. The resulting mixture was stirred at −10° C. for 12 hours. A saturated aqueous solution of NH₄Cl was added and the reaction mixture was extracted with EtOAc (2×). The organic layers were washed with a saturated aqueous solution of NaHCO₃. The combined organic layers were dried (MgSO₄) and the solvents were removed under reduced pressure. Purification by flash chromatography on silica (cHex:EtOAc, gradient 80:20 to 50:50) gave 172 mg (67%) of the title compound as a white powder. HPLC, Rt: 4.1 min (purity: 99.8%). LC/MS, M+(ESI): 413.3. ¹H NMR (CDCl₃) δ: 7.29 (m, 1H), 7.10 (m, 1H), 7.02-6.85 (m, 6H), 6.83 (d, J=15.1 Hz, 1H), 6.63 (d, J=15.1 Hz, 1H), 3.83 (s, 3H), 3.79 (s, 3H), 3.38 (m, 4H), 3.18 (m, 4H).

Step c) Formation of 1-{[2-(hydroxyamino)-4-(3-methoxyphenyl)-3-butynyl]sulfonyl}-4-(4-methoxyphenyl)piperazine

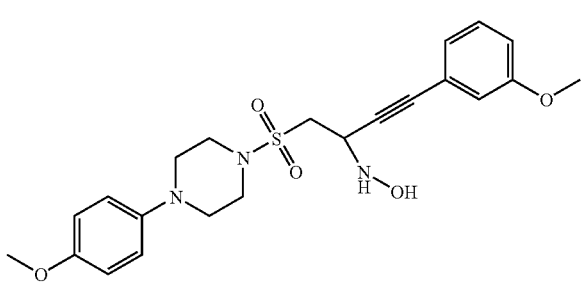

The title compound was prepared, following procedure described in Example 1, step b), but starting from 1-(4-methoxyphenyl)-4-{[(1E)-4-(3-methoxyphenyl)-1-buten-3-ynyl]sulfonyl}piperazine (91 mg, 0.22 mmol), as a white foam (126 mg, 71% yield). HPLC, Rt: 2.9 min (purity: 99.1%). LC/MS, M+(ESI): 446.4. ¹H NMR (CDCl₃) δ: 7.21 (m, 1H), 7.05 (m, 1H), 6.99-6.85 (m, 6H), 5.91 (brs, 1H), 5.08 (brs, 1H), 4.54 (dd, J=8.3, 4.2 Hz, 1H), 3.78 (s, 3H), 3.77 (s, 3H), 3.66 (dd, J=14.3, 8.3 Hz, 1H), 3.52 (m, 4H), 3.35 (dd, J=14.3, 4.2 Hz, 1H), 3.16 (m, 4H).

Step d) Formation of hydroxy[3-(3-methoxyphenyl)-1-({[4-(4-methoxyphenyl)-1-piperazinyl]sulfonyl}methyl)-2-propynyl]formamide

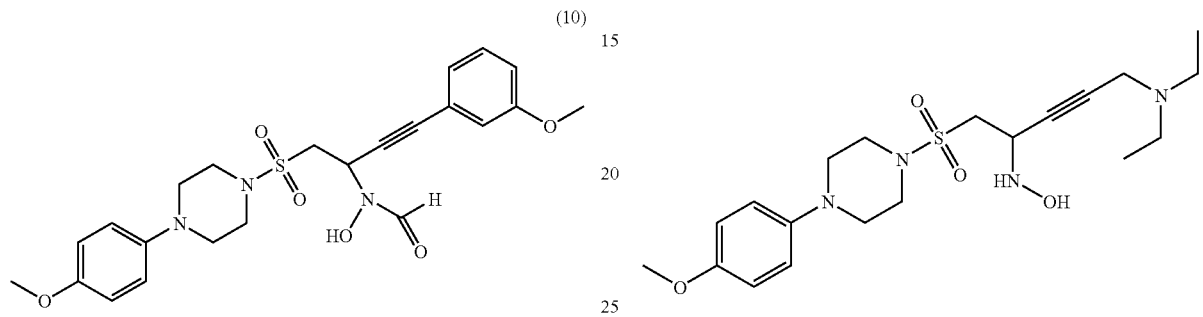

(10)

The title compound (10) was prepared, following procedure described in Example 1, step c), but starting from 1-{[2-(hydroxyamino)-4-(3-methoxyphenyl)-3-butynyl]sulfonyl}-4-(4-methoxyphenyl)piperazine (123 mg, 0.8 mmol, 1 eq.), as a pink foam (131 mg, 95% yield). HPLC, Rt: 3.0 min (purity: 99.7%). LC/MS, M+(ESI): 474.3, M⁻(ESI): 472.1. ¹H NMR (CDCl₃) δ: 8.47 (brs, 0.4H), 8.17 (brs, 0.6H), 7.22 (t, 1H, J=8.1Hz), 7.03 (m, 1H), 6.98-6.81 (m, 6H), 5.81 (brs, 0.5H), 5.28 (brs, 0.5H), 3.78 (s, 3H), 3.76 (s, 3H), 3.47 (m, 4H), 3.14 (m, 4H).

Example 11

4-(diethylamino)-1-({[4-(4-methoxyphenyl)-1-piperazinyl]sulfonyl}methyl)-2-butynyl(hydroxy)formamide (11)

Step a) Formation of a mixture of N,N-diethyl-N-((4E)-5-{[4-(4-methoxyphenyl)-1-piperazinyl]sulfonyl}-4-penten-2-ynyl)amine and N,N-diethyl-N-((4Z)-5-{[4-(4-methoxy phenyl)-1-piperazinyl]sulfonyl}-4-penten-2-ynyl)amine

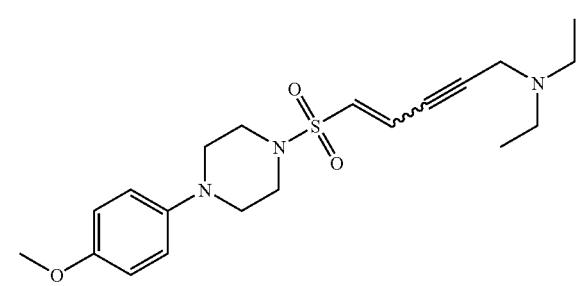

The title compound was prepared, following procedure described in Example 1, step a), but starting from 1-(4-methoxyphenyl)-4-(methylsulfonyl)piperazine (Intermediate B4, 450 mg, 1.66 mmol) and 4-(diethylamino)-2-butynal (Intermediate A4, 347 mg, 2.5 mmol), as a yellow powder (391 mg, 60% yield). HPLC, Rt: 2.0 min (purity: 93.3%). LC/MS, M+(ESI): 392.3. ¹H NMR (CDCl₃) δ: 6.94-6.84 (m, 4H), 6.63 (dt, J=15.0, 1.7 Hz, 1H), 6.52 (d, J=15.0 Hz, 1H), 3.78 (s, 3H), 3.63 (d, J=1.7 Hz, 2H), 3.34 (m, 4H), 3.15 (m, 4H), 2.58 (q, J=7.1 Hz, 4H), 1.10 (t, J=7.1 Hz, 6H).

Step b) Formation of N,N-diethyl-4-(hydroxyamino)-5-{[4-(4-methoxyphenyl)-1-piperazinyl]sulfonyl}-2-pentyn-1-amine The title compound was prepared, following procedure described in Example 1, step b), but starting from N, N-diethyl-N-((4E)-5-{[4-(4-methoxyphenyl)-1-piperazinyl]sulfonyl}-4-penten-2-ynyl)amine (391 mg, 1 mmol, 1 eq.), as a yellow oil (165 mg, 39% yield). HPLC, Rt: 1.50 min (purity: 53.8%). LC/MS, M+(ESI): 425.3. ¹H NMR (CDCl₃) δ: 6.95-6.81 (m, 4H), 4.33 (m, 1H), 3.76 (brs, 3H), 3.60-3.50 (m, 1H), 3.50-3.38 (m, 5H), 3.18-3.05 (m, 4H), 2.53 (q, 4H, J=7.1Hz), 1.05 (t, 6H, J=7.1Hz)

Step c) Formation of 4-(diethylamino)-1-({[4-(4-methoxyphenyl)-1-piperazinyl]sulfonyl}methyl)-2-butynyl(hydroxy)formamide (11)

The title compound (11) was prepared, following procedure described in Example 1, step c), but starting from N, N-diethyl-4-(hydroxyamino)-5-{[4-(4-methoxyphenyl)-1-piperazinyl]sulfonyl}-2-pentyn-1-amine (163 mg, 0.38 mmol), as a pale yellow foam (70 mg, 40% yield). HPLC, Rt: 1.5 min (purity: 99.8%). LC/MS, M+(ESI): 453.3, M⁻(ESI): 451.2. ¹H NMR (CD₃OD) δ: 8.34 (brs, 0.5H), 8.19 (brs, 0.5H), 7.01 (m, 2H), 6.89 (m, 2H), 5.70 (brs, 0.5H), 5.38 (brs, 0.5H), 3.80 (s, 2H), 3.78 (s, 3H), 3.55 (m, 2H), 3.16 (m, 4H), 2.96 (m, 4H), 1.23 (t, J=7.2 Hz, 6H).

Example 12 hydroxy(1-{[(4-pyridin-2-ylpiperazin-1-yl)sulfonyl]methyl}prop-2-yn-1-yl)formamide (12)

Step a) Formation of a mixture of 1-[(1E)-but-1-en-3-yn-1-ylsulfonyl]-4-pyridin-2-ylpiperazine and 1-[(1Z)-but-1-en-3-yn-1-ylsulfonyl]4-pyridin-2-ylpiperazine

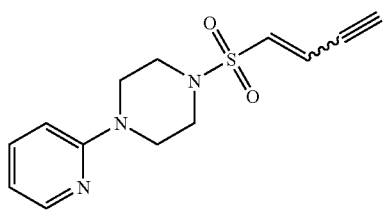

To a solution of 1-(2-pyridinyl)-4-{[(1E)-4-(trimethylsilyl)-1-buten-3-ynyl]sulfonyl}piperazine (prepared as in Example 3, step a; 174.8 mg; 0.50 mmol; 1.0 eq.) in THF (4 mL) at −20° C. was added a 1N solution of tetrabutylammonium fluoride (0.75 mL; 0.75 mmol; 1.50 eq). After 1 h, a saturated aqueous solution of NH$_4$Cl was added. The mixture was extracted with EtOAc and the combined organic layers were washed with water, brine, dried over MgSO$_4$, filtered and evaporated to give a brown oil. Purification on silicagel (EtOAc/c-Hex 40/60) gave the title product as a colorless oil (30 mg, 21%). $^1$H NMR (CDCl$_3$) δ: 8.01 (m, 1H), 7.25 (m, 1H), 6.50-6.21 (m, 4H), 3.42 (m, 4H), 3.20 (s, 1H), 3.05 (m, 4H).

Step b) Formation of 1-{[2-(hydroxyamino)but-3-yn-1-yl]sulfonyl}-4-pyridin-2-yl piperazine

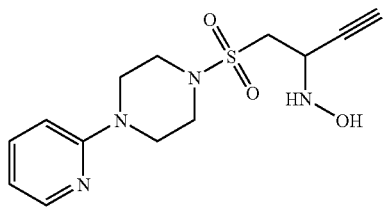

To a solution of 1-[(1E)-1-buten-3-ynylsulfonyl]-4-(2-pyridinyl)piperazine (30 mg; 0.11 mmol; 1.00 eq.) in THF (3 mL) was added an aq. solution of hydroxylamine (50%, 0.10 mL; 1.62 mmol; 15.0 eq.) and the resulting reaction mixture was stirred at 60° C. for 4 h. Evaporation of the solvents (rotavap gave an oil). Purification on silicagel (50/50 up to 70/30 AcOEt-c-Hex) a colorless oil (15 mg, 44% yield). LC/MS, M$^+$ (ESI): 311.1, M$^-$(ESI): 311.1, M$^-$ (ESI): 309.0.

Step c) Formation of hydroxy(1-{[(4-pyridin-2-ylpiperazin-1-yl)sulfonyl]methyl}prop-2-yn-1-yl) formamide

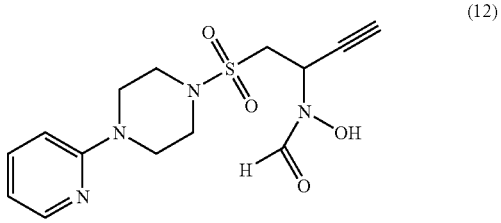

Acetic anhydride (25 mg; 0.24 mmol; 5.0 eq.) was added to cold (0° C.) formic acid (111 mg; 2.42 mmol; 50.0 eq.). The mixture was stirred 1 h, then a 1 M solution of 1-{[2-(hydroxyamino)-3-butynyl]sulfonyl}-4-(2-pyridinyl)piperazine (15 mg; 0.05 mmol; 1.0 eq.) in THF was added. After 4 h, the solvents were evaporated and the crude product was purified on silicagel (80/20 EtOAc/c-Hex) to give the title compound (12) as a colorless oil (2.3 mg, 14% yield). LC/MS, M$^+$(ESI): 339.2, M$^-$(ESI): 337.1.

Example 13

Hydroxy[1-({[4-(4-methoxyphenyl)piperidin-1-yl]sulfonyl}methyl)-3-phenylprop-2-yn-1-yl]formamide (13)

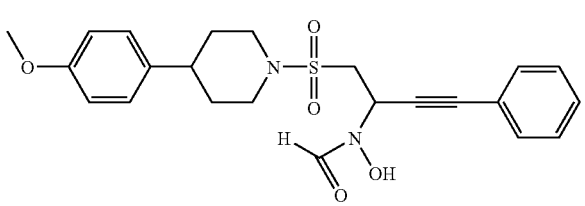

A solution of 4-(4-methoxyphenyl)-1-(methylsulfonyl)piperidine (Intermediate B5; 100 mg, 0.37 mmol) was prepared in anhydrous THF (3 mL) and cooled at 0° C. A solution of LiHMDS (1M in THF, 0.8 mL, 0.82 mmol) was added dropwise. After 5 min., diethyl chlorophosphate (54 μL, 0.37 mmol) was added. After 5 min., 3-phenylpropionaldehyde (55 μl, 0.45 mmol) was added and the reaction mixture was stirred at room temperature for 40 min. Then a 50% aqueous solution of NH$_2$OH (0.33 mL) was added and the resulting biphasic mixture was heated at 60° C. for 2.5 hours. Brine (5 mL) was added and the layers were separated. The aqueous layer was extracted with EtOAc (2×10 mL). The organic layers were combined, dried (MgSO$_4$) and the solvents were removed under reduced pressure to give a yellow oil. A mixture of formic acid (1.05 mL) and acetic anhydride (260 mL) was stirred at 0° C. for 30 min., then a solution of the previous oil in anhydrous THF (2 mL) was added and the resulting mixture was stirred at 0° C. for 30 min. The mixture was evaporated under reduced pressure. The residue was taken up in MeOH (4 mL) and heated at 60° C. for 30 min. The mixture was evaporated under reduced pressure to give a yellow oil, which was taken up in EtOAc (5 mL) and washed with a saturated aqueous solution of NaHCO$_3$ (5 mL). The aqueous layer was extracted with EtOAc (2×5 mL). The organic layers were combined, dried (MgSO₄) and the solvent was removed under reduced pressure. Purification by flash chromatography on silica gel (gradient cHex:EtOAc 2:1 to 1:2) gave the title compound as an orange foam (53 mg, 32% yield). HPLC, Rt: 4.0 min (purity: 96.3%). LC/MS, M⁺(ESI): 443.3, M⁻(ESI): 441.1.

Example 14

Hydroxy(1-{[(4-pyridin-2-ylpiperazin-1-yl)sulfonyl]methyl}hex-2-yn-1-yl)formamide (14)

Step a) Formation of 1-[(1E)-hept-1-en-3-yn-1-ylsulfonyl]-4-pyridin-2-ylpiperazine

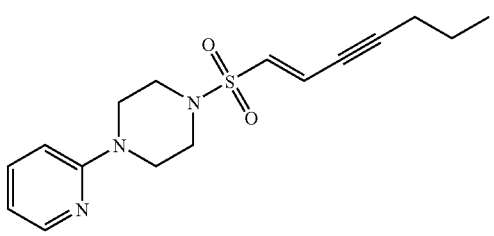

The title compound was prepared, following procedure described in Example 1, step a), but starting from 1-(methylsulfonyl)-4-(2-pyridinyl)piperazine (Intermediate B2, 502 mg; 2.08 mmol) and butyraldehyde (200 mg; 2.08 mmol) as a white powder (246 mg, 37% yield). HPLC, Rt: 2.48 min (purity: 98.9%). LC/MS, M⁺(ESI): 320.3, M⁻(ESI): 318.3. ¹H NMR (DMSO-d6) δ: 8.16 (m, 1H), 7.46 (m, 1H), 6.67 (m, 2H), 6.56 (dt, J=15.3, 2.3 Hz, 1H), 6.38 (d, J=15.3 Hz, 1H), 4.09 (t, J=5.2 Hz, 4H), 3.23 (t, J=5.0 Hz, 4H), 2.32 (td, J=7.0, 2.1 Hz, 2H), 1.55 (sx, J=7.2 Hz, 2H), 0.96 (t, J=7.3 Hz, 3H).

Step b) Formation of 1-{[2-(hydroxyamino)hept-3-yn-1-yl]sulfonyl}-4-pyridin-2-ylpiperazine

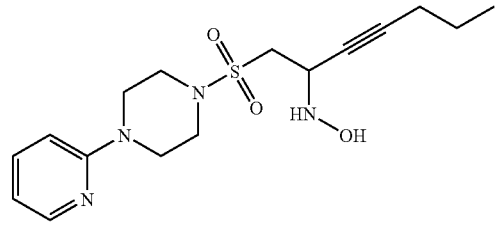

The title compound was prepared, following the procedure described in Example 1, step b) but starting from 1-[(1E)-hept-1-en-3-yn-1-ylsulfonyl]-4-pyridin-2-ylpiperazine (246 mg; 0.77 mmol) as a colorless oil (158 mg, 58% yield). HPLC, Rt: 1.21 min (purity: 100%). LC/MS, M⁺(ESI): 353.3. ¹H NMR (DMSO-d6) δ: 8.16 (m, 1H), 7.49 (m, 1H), 6.65 (m, 2H), 5.5 (brs, 2H), 4.25 (m, 1H), 3.63 (m, 4H), 3.51 (dd, J=14.1, 7.7 Hz, 1H), 3.52 (m, 4H), 3.15 (dd, J=14.0, 4.8 Hz, 1H), 2.12 (td, J=7.1, 2.1 Hz, 2H), 1.47 (sx, J=7.3 Hz, 2H), 0.92 (t, J=7.3 Hz, 3H).

Step c) Formation of hydroxy(1-{[(4-pyridin-2-ylpiperazin-1-yl)sulfonyl]methyl}hex-2-yn-1-yl)formamide

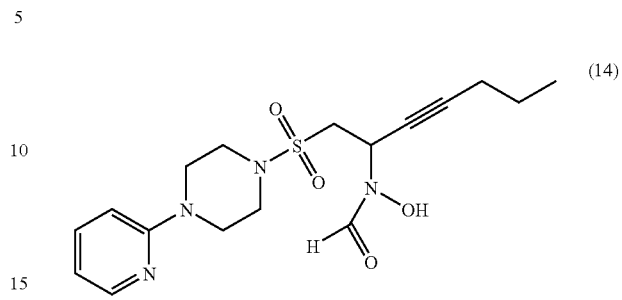

To a solution of 1-{[2-(hydroxyamino)hept-3-yn-1-yl]sulfonyl}-4-pyridin-2-ylpiperazine (157 mg; 0.45 mmol) in THF (5 mL) was added a solution of acetyl formate (200 mg, prepared as described by Kolle et al., 1983, *Helvetica Chimica Acta*, 66(8), 2760-8) in THF (2 mL). The reaction mixture was stirred at rt for 5 h and concentrated under reduced pressure. Purification of the crude by flash chromatography on silica (EtOAc:c-Hex, gradient from 50:50 to 100:0) gave the title compound as a white foam (90 mg, 53% yield). HPLC, Rt: 3.04 min (purity: 97.9%). LC/MS, M⁺(ESI): 381.3, M⁻(ESI): 379.2. ¹H NMR (DMSO-d6) δ: 8.39 (brs, 0.4H), 8.18 (m, 1H), 8.08 (brs, 0.6H), 7.48 (m, 1H), 6.66 (m, 2H), 5.53 (brs, 0.4H), 5.01 (brs, 0.6H), 3.63 (m, 5H), 3.36 (m, 6H), 2.14 (m, 2H), 1.49 (sx, J=7.2 Hz, 2H), 0.93 (t, J=7.3 Hz, 3H).

Example 15

[1-({[4-(2-fluorophenyl)piperazin-1-yl]sulfonyl}methyl)oct-2-yn-1-yl]hydroxyformamide (15)

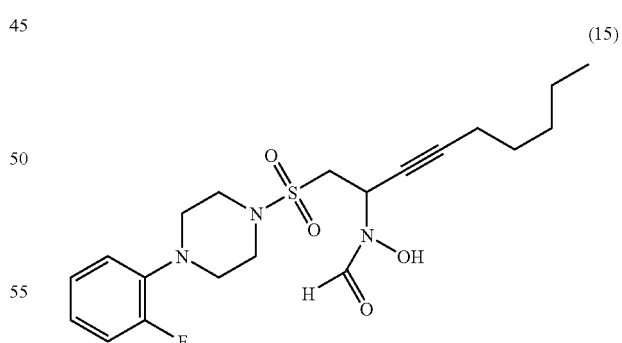

The title compound was prepared, following the procedure described in Example 13, but starting from 1-(2-fluorophenyl)-4-(methylsulfonyl)piperazine (300 mg; 1.16 mmol) and 1-octynal (0.17 mL, 1.22 mmol), as an orange oil (102 mg, 20% yield). HPLC, Rt: 4.12 min (purity: 99.9%). LC/MS, M⁺(ESI): 426.3, M⁻(ESI): 424.2.

Example 16

Hydroxy(1-{[(4-pyridin-2-ylpiperazin-1-yl)sulfonyl]methyl}oct-2-yn-1-yl)formamide (16)

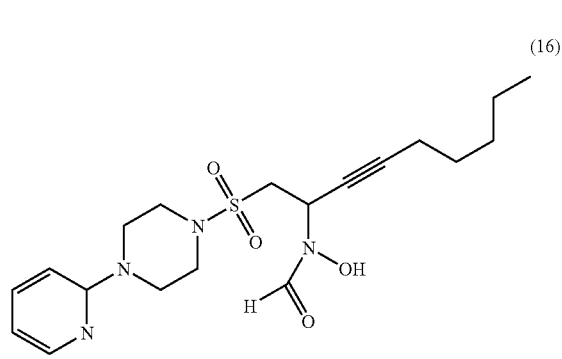

The title compound was prepared, following the procedure described in Example 13, but starting from 1-(methylsulfonyl)-4-(2-pyridinyl)piperazine (Intermediate B2; 300 mg; 1.24 mmol) and 2-octynal (0.19 ml; 1.31 mmol), as an orange oil (104 mg, 20% yield). HPLC, Rt: 2.35 min (purity: 95.2%). LC/MS, M+(ESI): 409.3, M-(ESI): 407.1.

Example 17

Hydroxy-N-{1-[({4-[4-(trifluoromethyl)phenyl]piperazin-1-yl}sulfonyl)methyl]oct-2-yn-1-yl}formamide (17)

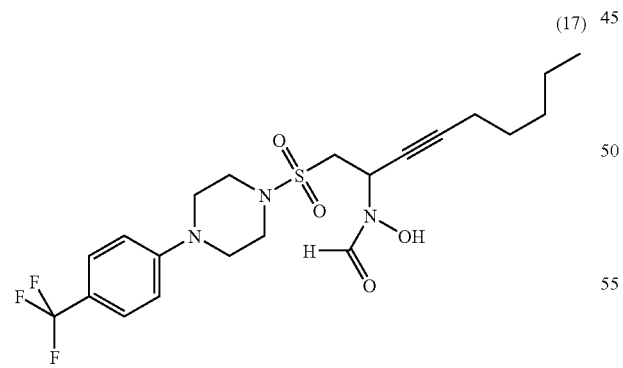

The title compound was prepared, following the procedure described in Example 13, but starting from 1-(methylsulfonyl)-4-[4-(trifluoromethyl)phenyl]piperazine (Intermediate B6; 300 mg; 0.97 mmol) and 2-octynal (0.15 mL; 1.02 mmol) as an orange solid (124 mg, 26% yield). HPLC, Rt: 4.50 min (purity: 99.9%). LC/MS, M+(ESI): 476.2.

Example 18

[1-({[4-(4-fluorophenyl)piperidin-1-yl]sulfonyl}methyl)oct-2-yn-1-yl]-N-hydroxyformamide (18)

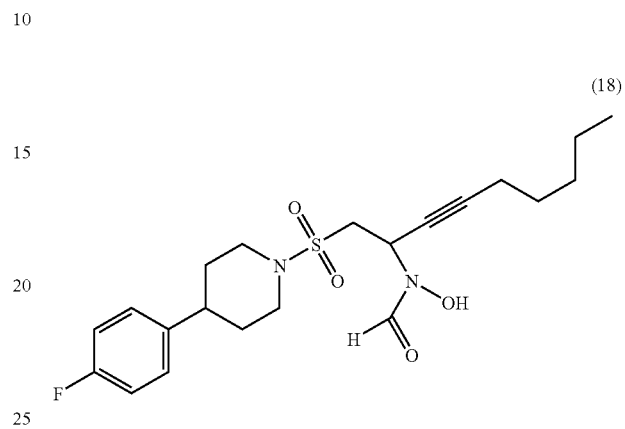

The title compound was prepared, following the procedure described in Example 13, but starting from 4-(4-fluorophenyl)-1-(methylsulfonyl)piperidine (Intermediate B7; 300 mg; 1.17 mmol) and 2-octynal (0.17 mL; 1.22 mmol), as white solid (35 mg, 7% yield). HPLC, Rt: 4.31 min (purity: 98.2%). LC/MS, M+(ESI): 425.3, M-(ESI): 423.1.

Example 19

Hydroxy[1-({[4-4-methyloxyphenyl)piperidin-1-yl]sulfonyl}methyl)oct-2-yn-1-yl]formamide (19)

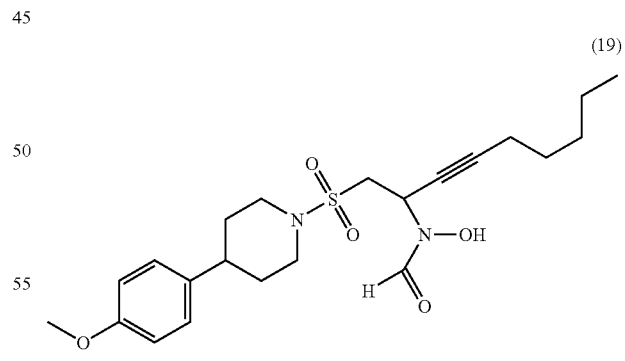

The title compound was prepared, following the procedure described in Example 13, but starting from 4-(4-methoxyphenyl)-1-(methylsulfonyl)piperidine (Intermediate B5; 300 mg; 1.11 mmol) and 2-octynal (0.17 mL; 1.17 mmol), as an orange solid (54 mg, 11% yield). HPLC, Rt: 4.24 min (purity: 100%). LC/MS, M+(ESI): 437.3; M-(ESI): 435.2.

Example 20

[1-({[4-(4-fluorophenyl)piperazin-1-yl]sulfonyl}methyl)-3-(3-methyloxy phenyl)prop-2-yn-1-yl]hydroxyformamide (20)

Step a) Formation of diethyl({[4-(4-fluorophenyl)piperazin-1-yl]sulfonyl}methyl)phosphonate

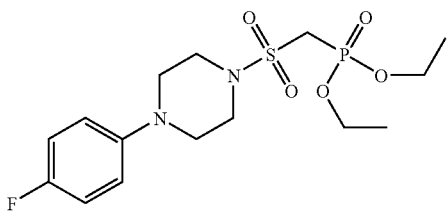

The title compound was prepared, following procedure described in Example 10, but starting from 1-(4-fluorophenyl)-4-(methylsulfonyl)piperazine (10.3 g; 40.0 mmol) as a white powder (11.0 g, 70% yield). HPLC, Rt: 2.88 min (purity: 98.9%).

Step b) Formation of a mixture of 1-(4-fluorophenyl)-4-{[(1E)-4-(3-methyloxyphenyl)but-1-en-3-yn-1-yl]sulfonyl}piperazine and -(4-fluorophenyl)-4-{[(1Z)-4-(3-methyloxyphenyl)but-1-en-3-yn-1-yl]sulfonyl}piperazine

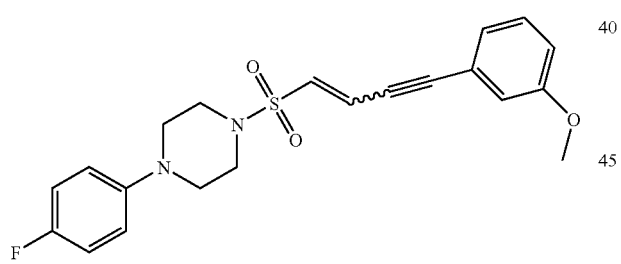

A suspension of diethyl({[4-(4-fluorophenyl)piperazin-1-yl]sulfonyl}methyl)phosphonate (404 mg; 1.02 mmol), 3-methoxyphenylpropargylalcohol (Intermediate A5; 249 mg; 1.54 mmol), MnO$_2$ (890 mg; 10.2 mmol), lithium hydroxide (74 mg; 3.1 mmol) and molecular sieves (4 A, 150 mg) in THF (5 mL) was heated under MW at 150° C. for 2500 s. The mixture was filtered through a celite pad and rinsed with EtOAc. The filtrate was concentrated under reduced pressure and purified by flash chromatography on silica (EtOAc:c-Hex, 5:95) to give the title compound as a brown-orange solid (335 mg, 82% yield). HPLC, Rt: 4.60 min (purity: 93.8%). LC/MS, M$^+$(ESI): 401.2. $^1$H NMR (DMSO-d6) δ: 7.23 (m, 1H), 7.06 (m, 1H), 6.83-6.95 (m, 6H), 6.80 (d, J=15.3 Hz, 0.95H), 6.60 (d, J=15.3 Hz, 0.95H), 6.46 (AB, J=11.1, 33.5 Hz, 0.1H), 3.80 (s, 2.85H), 3.78 (s, 0.15H), 3.35 (m, 4H), 3.17 (m, 4H).

Step c) Formation of 1-(4-fluorophenyl)-4-{[2-(hydroxyamino)-4-(3-methoxyphenyl)but-3-yn-1-yl]sulfonyl}piperazine The title compound was prepared, following procedure described in Example 1, step b), but starting from 1-(4-fluorophenyl)-4-{[4-(3-methoxyphenyl)but-1-en-3-yn-1-yl]sulfonyl}piperazine (335 mg; 0.84 mmol), as a yellow oil (349 mg, 96% yield). HPLC, Rt: 3.47 min (purity: 75%). LC/MS, M$^+$(ESI): 434.2

Step d) Formation of [1-({[4-(4-fluorophenyl)piperazin-1-yl]sulfonyl}methyl)-3-(3-methyloxyphenyl)prop-2-yn-1-yl]hydroxyformamide (20)

A solution of 1-(4-fluorophenyl)-4-{[2-(hydroxyamino)-4-(3-methoxyphenyl)but-3-yn-1-yl]sulfonyl}piperazine (349 mg; 0.81 mmol) and acetyl formate (prepared as described by Koller et al., 1983, above 8; 0.58 mL of a 1.39 M solution in THF; 0.81 mmol) was stirred at rt for 1 h. THF was removed under reduced pressure and replaced by MeOH. The solution was heated at 60° C. for 1 h and concentrated under reduced pressure. Purification of the crude by flash chromatography on silica (EtOAc:c-Hex 60:40 to 100:0) gave the title compound as an orange oil (90 mg, 24% yield). HPLC, Rt: 3.69 min (purity: 99.3%). LC/MS, M$^+$(ESI): 462.3. $^1$H NMR (DMSO-d6) δ: 8.45 (brs, 0.4H), 8.13 (brs, 0.6H), 7.19 (m, 1H), 6.97-7.04 (m, 7H), 5.80 (brs, 0.4H), 5.25 (brs, 0.6H), 3.77 (s, 3H), 3.68 (brs, 1H), 3.44 (m, 6H), 3.14 (m, 4H).

Example 21

[1-({[4-4-fluorophenyl)piperazin-1-yl]sulfonyl}methyl)hex-2-yn-1-yl]hydroxyformamide (21)

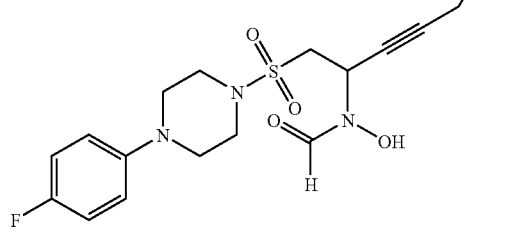

(21)

A suspension of diethyl({[4-(4-fluorophenyl)piperazin-1-yl]sulfonyl}methyl)phosphonate (prepared in Example 20, step a); 428 mg; 1.09 mmol), 2-hexyn-1-ol (179 μl; 1.63 mmol), MnO$_2$ (943 mg; 10.9 mmol), lithium hydroxyde (78 mg; 3.3 mmol) and molecular sieves (4 A, 150 mg) in THF (5 mL) was heated in the MW at 150° C. for 2500 s. The mixture was filtered through a celite pad and rinsed with EtOAc. The filtrate was concentrated under reduced pressure and redissolved in THF (4 mL). Hydroxylamine (1.8 mL) was added and the mixture was heated at 60° C. for 2 h. THF was removed under reduced pressure and the residue was dissolved in EtOAc, washed with saturated NH$_4$Cl and brine. Organic phase was then dried over magnesium sulfate, filtrated and concentrated to give 396 mg of a colorless oil. Formylation was performed following the procedure described in example 20, step b). The title compound was obtained as a white solid (125 mg, 29% yield). HPLC, Rt: 3.25 min (purity: 98.4%). LC/MS, M$^+$(ESI): 398.2, $^1$H NMR (DMSO-d6) δ: 8.40 (brs, 0.4H), 8.07 (brs, 0.6H), 6.87-6.99 (m, 4H), 5.52 (brs, 0.4H), 5.02 (brs, 0.6H), 3.13-3.80 (m, 11H), 2.17 (m, 2H), 1.52 (sx, J=7.2 Hz, 2H), 0.95 (t, J=7.3 Hz, 3H).

Example 22

[1-({[4-(4-fluorophenyl)piperazin-1-yl]sulfonyl}methyl)-3-quinolin-3-yl prop-2-yn-1-yl]hydroxyformamide (22)

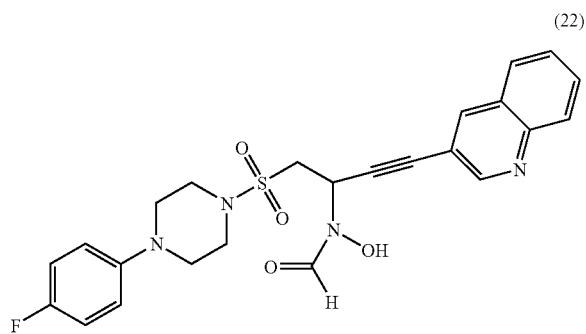

(22)

The title compound was prepared, following procedure described in Example 21, but starting from diethyl({[4-(4-fluorophenyl)piperazin-1-yl]sulfonyl}methyl)phosphonate (399 mg; 1.01 mmol) and 3-Quinolin-3-yl-prop-2-yn-1-ol (278 mg; 1.52 mmol) as a yellow powder (110 mg, 32% yield). HPLC, Rt: 3.08 min (purity: 98.6%). LC/MS, M$^+$(ESI): 483.3. $^1$H NMR (DMSO-d6) δ: 8.89 (s, 1H), 8.55 (s, 0.6H), 8.12 (s, 0.4H), 7.77 (m, 2H), 7.77 (m, 1H), 7.66 (brs, 1H), 7.60 (m, 1H), 6.90-7.00 (m, 4H), 5.95 (brs, 0.6H), 5.35 (brs, 0.4H), 3.75 (m, 1H), 3.52 (m, 6H), 3.19 (m, 4H).

Example 23

[1-({[4-(4-fluorophenyl)piperidin-1-yl]sulfonyl}methyl)-3-phenylprop-2-yn-1-yl]hydroxyformamide (23)

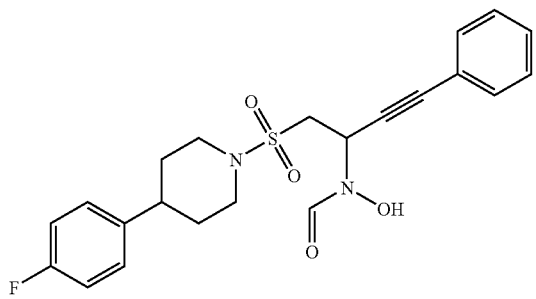

(23)

The title compound was prepared, following the procedure described in Example 13, but starting from 4-(4-fluorophenyl)-1-(methylsulfonyl)piperidine (Intermediate B7; 386 mg; 1.5 mmol) and phenylpropionaldehyde (235 mg, 1.8 mmol), as an yellow powder (228 mg, 35% yield). HPLC, Rt: 4.06 min (purity: 99.8%). LC/MS, M$^+$(ESI): 431.3, M-(ESI): 429.1.

Example 24

Hydroxy(3-phenyl-1-{[(4-pyridin-2-ylpiperazin-1-yl)sulfonyl]methyl}prop-2-yn-1-yl)formamide (24)

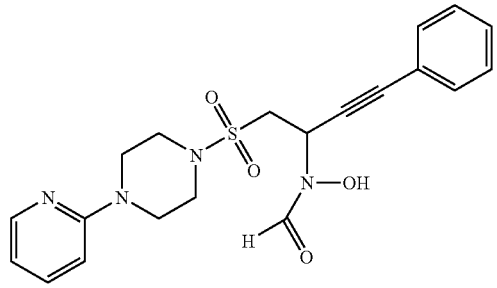

(24)

The title compound was prepared, following the procedure described in Example 13, but starting from 4-(2-pyridinyl)-1-(methylsulfonyl)piperazine (Intermediate B2; 362 mg; 1.5 mmol) and phenylpropionaldehyde (235 mg, 1.8 mmol), as an yellow powder (66 mg, 11% yield). HPLC, Rt: 1.93 min (purity: 97.5%). LC/MS, M+(ESI): 415.2, M−(ESI): 413.1.

Example 25

Hydroxy{3-phenyl-1-[({4-[4-(trifluoromethyl)phenyl]piperazin-1-yl}sulfonyl)methyl]prop-2-yn-1-yl}formamide (25)

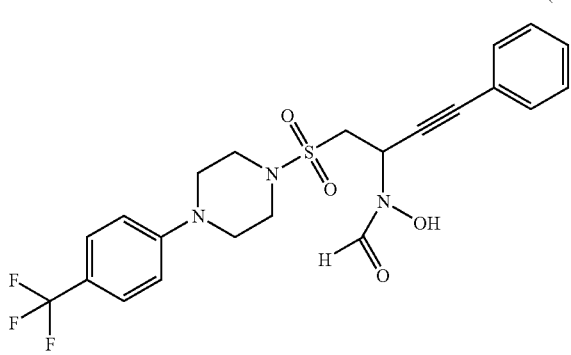

(25)

The title compound was prepared, following the procedure described in Example 13, but starting from 4-(2-pyridinyl)-1-(methylsulfonyl)piperazine (Intermediate B6; 462 mg; 1.5 mmol) and phenylpropionaldehyde (235 mg, 1.8 mmol), as a beige powder (209 mg, 29% yield). HPLC, Rt: 4.27 min (purity: 100%). LC/MS, M+(ESI): 482.2.

Example 26

Hydroxy[1-({[4-(4-methyloxyphenyl)piperazin-1-yl]sulfonyl}methyl)-3-phenylprop-2-yn-1-yl]formamide (26)

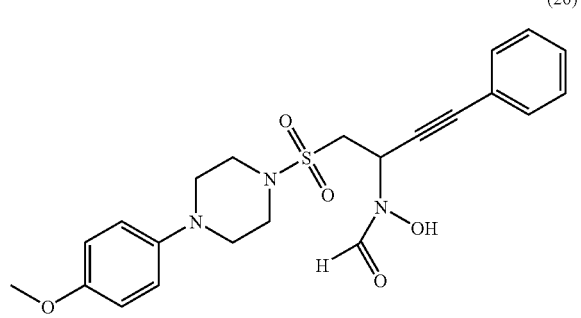

(26)

The title compound was prepared, following the procedure described in Example 13, but starting from 1-(4-methoxyphenyl)-4-(methylsulfonyl)piperazine (Intermediate B4; 405 mg; 1.5 mmol) and phenylpropionaldehyde (235 mg, 1.8 mmol), as a yellow powder (75 mg, 11% yield). HPLC, Rt: 2.88 min (purity: 99.26%). LC/MS, M+(ESI): 444.3, M-(ESI): 442.1.

Example 27

{1-({[4-(4-fluorophenyl)piperazin-1-yl]sulfonyl}methyl)-3-[4-(1,2,4-oxadiazol-3-yl)phenyl]prop-2-yn-1-yl}hydroxyformamide (27)

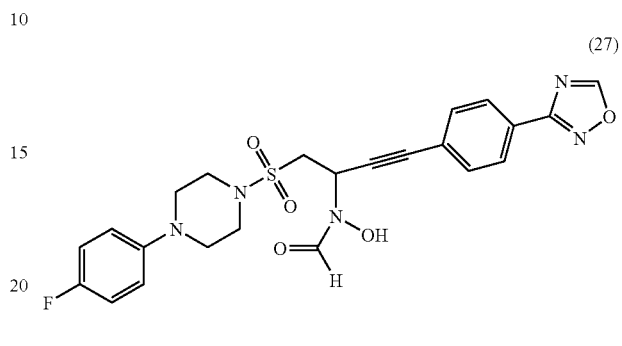

(27)

The title compound was prepared, following procedure described in Example 21, but starting from diethyl({[4-(4-fluorophenyl)piperazin-1-yl]sulfonyl}methyl)phosphonate (prepared in Example 20, step a); 468 mg; 1.19 mmol) and 3-hydroxyprop-1-ynyl)benzonitrile (279 mg; 1.78 mmol) as a yellow foam (84 mg, 14% yield). HPLC, Rt: 3.57 min (purity: 94.7%). LC/MS, M+(ESI): 500.2, M−(ESI): 498.1. $^1$H NMR (DMSO-d6) δ: 8.76 (s, 1H), 8.47 (brs, 0.4H), 8.16 (brs, 0.6H), 8.07 (d, J=8.3 Hz, 2H), 7.56 (d, J=8.3 Hz, 2H), 6.85-6.99 (m, 4H), 5.85 (brs, 0.4H), 5.28 (brs, 0.6H), 3.4-3.9 (m, 7H), 3.20 (m, 4H).

Example 28

Hydroxy[1-({[4-(4-methyloxyphenyl)piperazin-1-yl]sulfonyl}methyl)oct-2-yn-1-yl]formamide (28)

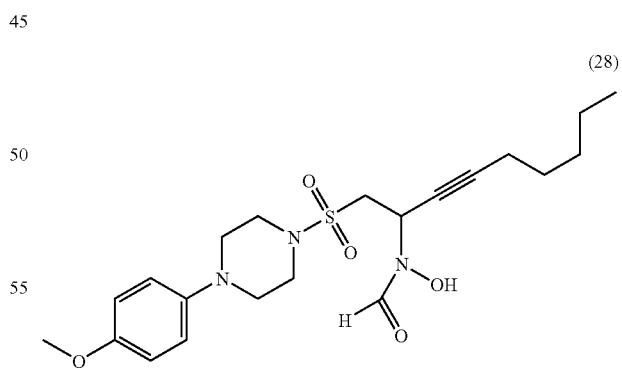

(28)

The title compound was prepared, following the procedure described in example 13, but starting from 1-(4-methoxyphenyl)-4-(methylsulfonyl)piperazine (Intermediate B4; 300 mg; 1.11 mmol) and 2-octynal (0.17 ml; 1.17 mmol), as a white solid (77 mg, 16% yield). HPLC, Rt: 3.25 min (purity: 100%). LC/MS, M+(ESI): 438.3, M-(ESI): 436.1.

Example 29

(1-{[(4-biphenyl-4-ylpiperazin-1-yl)sulfonyl]methyl}-3-phenylprop-2-yn-1-yl)hydroxyformamide (29)

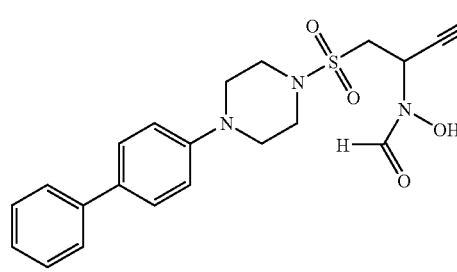

The title compound was prepared, following the procedure described in Example 13, but starting from 1-[1,1'-biphenyl]-4-yl-4-(methylsulfonyl)piperazine (Intermediate B8; 475 mg; 1.5 mmol) and phenylpropionaldehyde (235 mg, 1.8 mmol), as a beige powder (39 mg, 11% yield). HPLC, Rt: 4.32 min (purity: 87.4%). LC/MS, M$^+$(ESI): 490.2, M-(ESI): 488.0.

Example 30

[1-({[4-(5-chloropyridin-2-yl)piperazin-1-yl]sulfonyl}methyl)oct-2-yn-1-yl]hydroxyformamide (30)

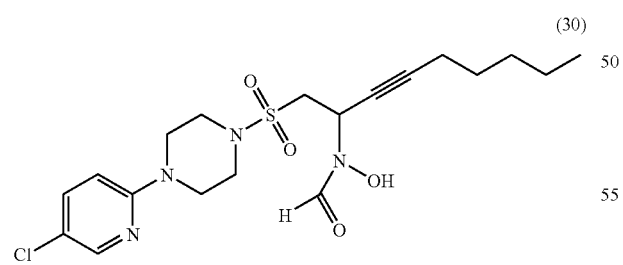

The title compound was prepared, following the procedure described in Example 13, but starting from 1-(5-chloropyridin-2-yl)-4-(methylsulfonyl)piperazine (Intermediate B9; 379 mg; 1.37 mmol) and 2-octynal (0.17 mL; 1.20 mmol), as a white powder (248 mg, 41% yield). HPLC, Rt: 3.61 min (purity: 100%). LC/MS, M$^+$(ESI): 443.2, M-(ESI): 441.0.

Example 31

Hydroxy(1-{[(4-pyrimidin-2-ylpiperazin-1-yl)sulfonyl]methyl}oct-2-yn-1-yl)formamide (31)

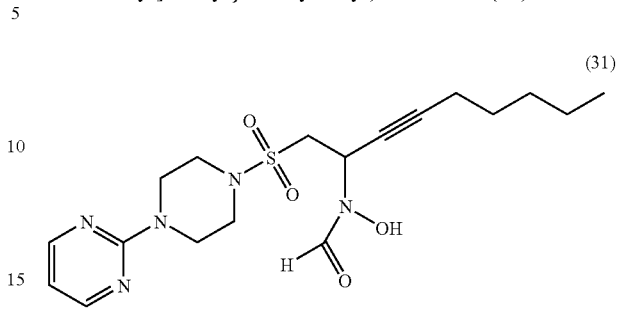

The title compound was prepared, following the procedure described in Example 13, but starting from 2-[4-(methylsulfonyl)piperazin-1-yl]pyrimidine (Intermediate B10; 400 mg; 1.65 mmol) and 2-octynal (0.28 mL; 1.98 mmol), as a pink powder (155 mg, 23% yield). HPLC, Rt: 3.11 min (purity: 100%). LC/MS, M$^+$(ESI): 410.3, M-(ESI): 408.1.

Example 32

Hydroxy(1-{[(4-phenylpiperazin-1-yl)sulfonyl]methyl}oct-2-yn-1-yl)formamide (32)

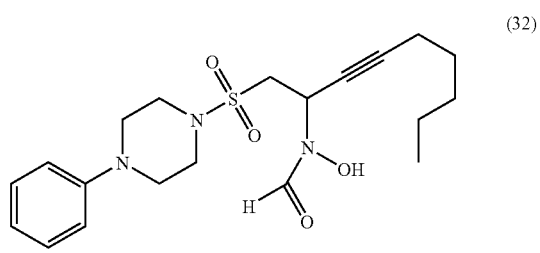

The title compound was prepared, following the procedure described in Example 13, but starting from 1-(methylsulfonyl)-4-phenylpiperazine (400 mg; 1.66 mmol) and 2-octynal (0.29 mL; 2.0 mmol), as an off-white powder (258 mg, 38% yield). HPLC, Rt: 3.72 min (purity: 100%). LC/MS, M$^+$(ESI): 408.3, M$^-$(ESI): 406.2.

Example 33

[1-({[4-(4-chlorophenyl)piperazin-1-yl]sulfonyl}methyl)oct-2-yn-1-yl]hydroxyformamide (33)

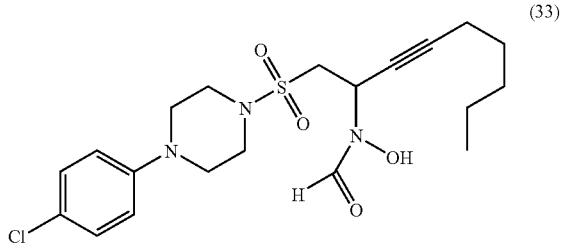

The title compound was prepared, following the procedure described in Example 13, but starting from 1-(4-chlorophenyl)-4-(methylsulfonyl)piperazine (Intermediate B11, 400 mg; 1.46 mmol) and 2-octynal (0.25 mL; 1.75 mmol), as an orange powder (192 mg, 30% yield). HPLC, Rt: 4.26 min (purity: 99.5%). LC/MS, M+(ESI): 442.2, M−(ESI): 440.1.

Example 34 hydroxy[1-({[4-(2-methyloxyphenyl)piperazin-1-yl]sulfonyl}methyl)oct-2-yn-1-yl]formamide (34)

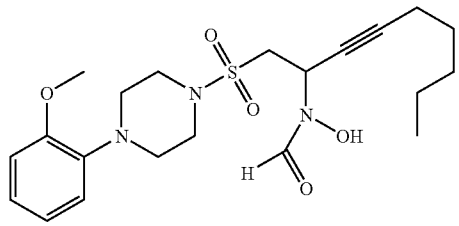

(34)

The title compound was prepared, following the procedure described in Example 13, but starting from 1-(2-methoxyphenyl)-4-(methylsulfonyl)piperazine (400 mg; 1.48 mmol) and 2-octynal (0.25 mL; 1.75 mmol), as a beige powder (159 mg, 25% yield). HPLC, Rt: 3.30 min (purity: 98.25%). LC/MS, M+(ESI): 438.2, M−(ESI): 435.9.

Example 35

Hydroxy[1-({[4-(3-methyloxyphenyl)piperazin-1-yl]sulfonyl}methyl)oct-2-yn-1-yl]formamide (35)

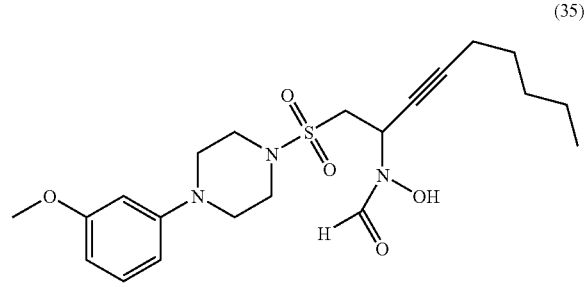

(35)

The title compound was prepared, following the procedure described in Example 13, but starting from 1-(3-methoxyphenyl)-4-(methylsulfonyl)piperazine (Intermediate B12; 500 mg; 1.85 mmol) and 2-octynal (0.32 mL; 2.22 mmol), as a beige powder (451 mg, 56% yield). HPLC, Rt: 3.85 min (purity: 99.0%). LC/MS, M+(ESI): 438.3, M−(ESI): 436.2.

Example 36

[1-({[4-(4-fluorophenyl)piperazin-1-yl]sulfonyl}methyl)-2,2-dimethyl-5-phenylpent-4-yn-1-yl]hydroxyformamide (36)

Step a) Formation of 1-(4-fluorophenyl)-4-{[2-(hydroxyamino)-3,3-dimethyl-6-phenylhex-5-yn-1-yl]sulfonyl}piperazine

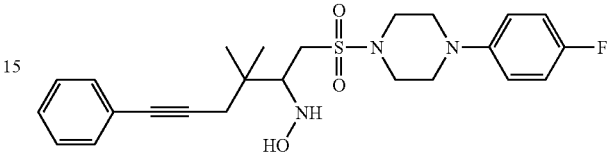

To a solution of 1-(4-fluorophenyl)-4-(methylsulfonyl)piperazine (Intermediate B1; 600 mg; 2.32 mmol) in THF (10 mL) was added Lithiumbis(trimethylsilyl)amide (4.65 mL of a 1.00 M solution in THF; 4.65 mmol) at −78° C. under $N_2$. After 30 min, diethylchlorophosphate (0.38 mL; 2.56 mmol) was added and the mixture was stirred at −78° C. for one hour. A solution of 2,2-dimethyl-5-phenylpent-4-ynal (prepared as described by Cossy et al., 1997, *Journal of Organic Chemistry*, 62(23), 7900-7901, 432 mg; 2.32 mmol) in THF (5 mL) was cannulated and the reaction mixture was allowed to warm to rt and stirred for 12 h. Hydroxylamine (4.1 mL; 70 mmol was then added and the mixture was heated at 60° C. for 3 h. It was finally concentrated under reduced pressure, redissolved in is EtOAc, washed with a saturated solution of $NH_4Cl$ and with brine, dry over magnesium sulfate, filtrated and concentrated. Purification of the crude by flash chromatography on silica (EtOAc:c-Hex; gradient from 20:80 to 50:50) gave the title compounds as a yellow oil (710 mg, 66% yield). HPLC, Rt: 4.15 min (purity: 95.9%). LC/MS, M+(ESI): 460.2. $^1$H NMR (DMSO-d6) δ: 7.37 (m, 2H), 7.23 (m, 3H), 6.96 (m, 2H), 6.86 (m, 2H), 3.60 (dd, J=14.2, 10.1 Hz, 1H), 3.61 (m, 4H), 3.34 (dd, J=10.1, 1.8 Hz, 1H), 3.12 (m, 5H), 2.37 (AB, J=15.9, Δ=49.3 Hz, 2H), 1.12 (s, 3H), 1.14 (s, 3H).

Step b) Formation of [1-({[4-(4-fluorophenyl)piperazin-1-yl]sulfonyl}methyl)-2,2-dimethyl-5-phenylpent-4-yn-1-yl]hydroxyformamide

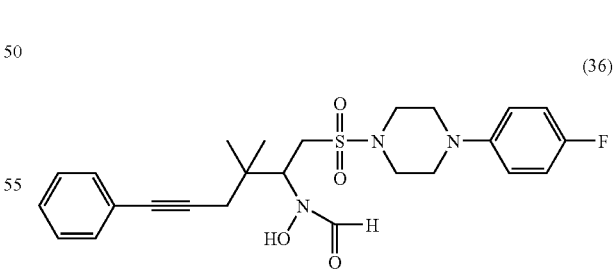

(36)

The title compound (36) was prepared, following procedure described in Example 1, step c), but starting from 1-(4-fluorophenyl)-4-{[2-(hydroxyamino)-3,3-dimethyl-6-phenylhex-5-yn-1-yl]sulfonyl}piperazine (710 mg; 1.54 mmol) as a white powder (268 mg, 36% yield). HPLC, Rt: 4.08 min (purity: 98.8%). LC/MS, M+(ESI): 488.1, M−(ESI): 486.0. $^1$H NMR (DMSO-d6) δ: 9.99 (s, 0.3H), 9.78 (s, 0.7H), 8.28 (s, 0.3H), 7.93 (s, 0.7H), 7.28-7.37 (m, 5H), 6.88-7.07 (m, 4H), 4.72 (d, J=8.3 Hz, 0.3H), 7.03 (d, J=8.3 Hz, 0.7H), 3.48 (m, 2H), 3.41 (m, 4H), 3.10 (m, 4H), 2.41-2.47 (m, 2H), 1.05 (m, 6H).

Example 37

[4-(diethylamino)-1-({[4-(4-methyloxyphenyl)piperidin-1-yl]sulfonyl}methyl)but-2-yn-1-yl]hydroxyformamide (37)

Step a) diethyl({[4-(4-methoxyphenyl)piperidin-1-yl]sulfonyl}methyl)phosphonate

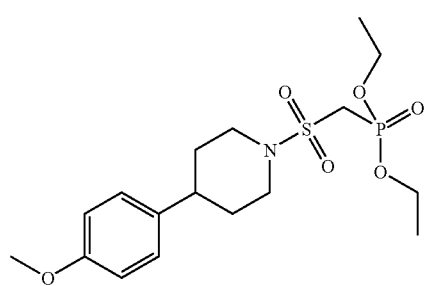

The title compound was prepared, following procedure described in Example 10, step a) but starting from 4-(4-methoxyphenyl)-1-(methylsulfonyl)piperidine (Intermediate B4; 2.92 g; 10.9 mmol) as a white powder (3.86 g, 88% yield). HPLC, Rt: 3.65 min (purity: 100%). LC/MS, M+(ESI): 406.3, M−(ESI): 404.2. $^1$H NMR (DMSO-d6) δ: 7.12 (d, J=8.6 Hz, 2H), 6.86 (d, J=8.6 Hz, 2H), 4.31-4.21 (m, 4H), 3.97 (m, 2H), 3.8 (s, 3H), 3.56 (d, J=17.3 Hz, 2H), 2.97 (m, 2H), 2.59 (m, 1H), 1.94-1.78 (m, 4H), 1.40 (t, J=7.0 Hz, 6H).

Step b) Formation of N,N-diethyl-4-(hydroxyamino)-5-{[4-(4-methoxyphenyl)piperidin-1-yl]sulfonyl}pent-2-yn-1-amine

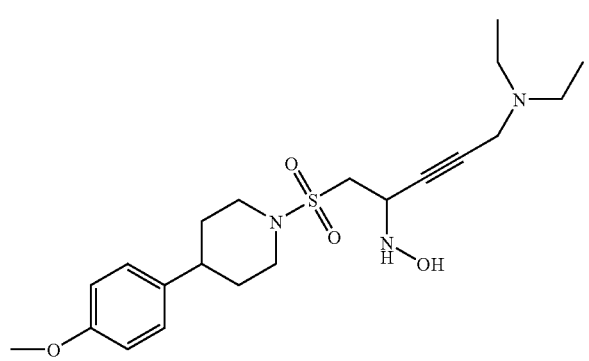

A suspension of diethyl({[4-(4-methoxyphenyl)piperidin-1-yl]sulfonyl}methyl) phosphonate (558 mg; 1.38 mmol), MnO$_2$ (1.2 g, 13.8 mmol), lithium hydroxyde (99 mg; 4.13 mmol), molecular sieves (4A, 300 mg) and 4-diethylamino-2-butyl-1-ol (306.21 μl; 2.06 mmol) in THF (5 mL) was heated in the MW at 150° C. for 2500 s. The mixture was filtered through a celite pad and rinsed with EtOAc. The filtrate was concentrated under reduced pressure and redissolved in THF (15 mL), hydroxylamine (2.44 mL) was added and the reaction mixture was heated at 60° C. for 2 h. The solvent was removed under reduced pressure and the residue was dissolved in EtOAc, washed with a saturated solution of NH$_4$Cl and with brine. The organic phase was dried over magnesium sulfate, filtrated and concentrated. Purification of this crude (524 mg) by flash chromatography on silica (DCM: MeOH:NH$_4$OH 90:10:0.1) gave the title compound as a brown oil (97 mg, 17% yield). HPLC, Rt: 2.50 min (purity: 80%). LC/MS, M+(ESI): 424.0. $^1$H NMR (DMSO-d6) δ 7.10 (d, J=8.7 Hz, 2H), 6.84 (d, J=8.7 Hz, 2H), 4.31 (m, 1H), 3.91 (m, 2H), 3.77 (s, 3H), 3.52 (dd, J=13.9, 8.3 Hz, 1H), 3.44 (d, J=1.9 Hz, 2H), 3.16 (dd, J=13.9, 4.3 Hz, 1H), 2.91 (m, 2H), 2.56 (qd, J=7.2 Hz, 4H), 2.53 (m, 1H), 1.95 (m, 2H), 1.74-1.88 (m, 2H), 1.07 (t, J=7.2Hz, 6H).

Step c) Formation of [4-(diethylamino)-1-({[4-(4-methoxyphenyl)piperidin-1-yl]sulfonyl}methyl)but-2-yn-1-yl]hydroxyformamide

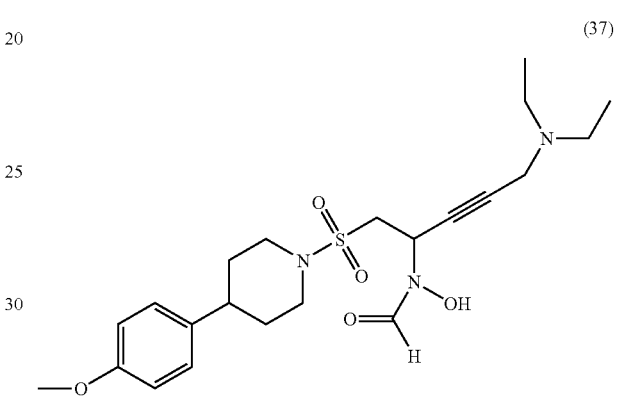

The title compound (37) was prepared, following procedure described in Example 1, step c) but starting from N,N-diethyl-4-(hydroxyamino)-5-{[4-(4-methoxyphenyl)piperidin-1-yl]sulfonyl}pent-2-yn-1-amine (97 mg; 0.23 mmol) as an orange oil (64 mg, 49% yield). HPLC, Rt: 2.58 min (purity: 100%). LC/MS, M+(ESI): 452.2, M−(ESI): 450.1. $^1$H NMR (DMSO-d6) δ 11.80 (brs, 1H), 8.6 (brs, 1H), 8.35 (s, 1H), 7.09 (d, J=8.7 Hz, 2H), 6.83 (d, J=8.5 Hz, 2H), 5.67 (m, 0.6H), 5.10 (brs, 0.2H), 4.50 (brs, 0.2H), 3.87-4.00 (m, 4H), 3.77 (s, 3H), 3.20-4.42 (m, 6H), 2.86 (t, J=11.9 Hz, 2H), 2.56 (m, 1H), 1.72-1.87 (m, 4H), 1.34 (m, 6H).

Example 38 hydroxy{1-[({4-[5-(trifluoromethyl)pyridin-2-yl]piperazin-1-yl}sulfonyl)methyl]oct-2-yn-1-yl}formamide (38)

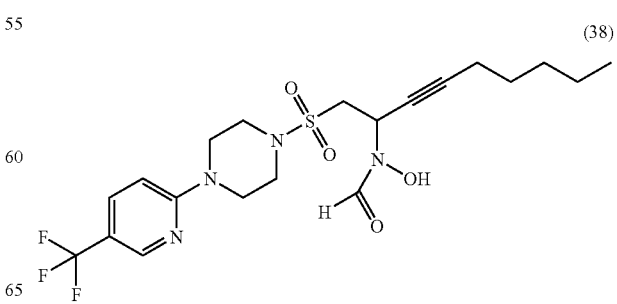

The title compound was prepared, following the procedure described in Example 13, but starting from 1-methanesulfonyl-4-(5-trifluoromethylpyridin-2-yl)piperazine (Intermediate B13; 500 mg; 1.62 mmol) and 2-octynal (0.28 mL; 1.94 mmol), as a beige powder (124 mg, 16% yield). HPLC, Rt: 4.29 min (purity: 96.7%). LC/MS, M⁺(ESI): 477.4, M⁻(ESI): 475.2.

Example 39

Hydroxy[1-({[4-(4-phenoxyphenyl)piperazin-1-yl]sulfonyl}methyl)oct-2-yn-1-yl]formamide (39)

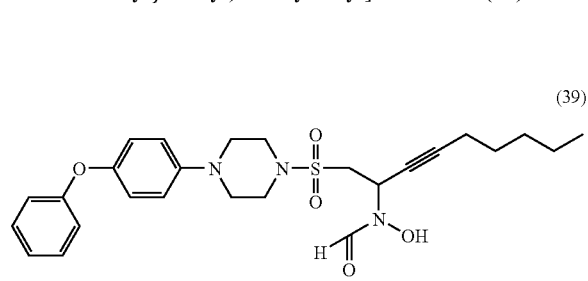

(39)

The title compound was prepared, following the procedure described in Example 13, but starting from 1-(methylsulfonyl)-4-(4-phenoxyphenyl)piperazine (Intermediate B14; 500 mg; 1.50 mmol) and 2-octynal (0.26 mL; 1.80 mmol), as a white powder (273 mg, 36% yield). HPLC, Rt: 4.58 min (purity: 99.7%). LC/MS, M⁺(ESI): 500.3, M⁻(ESI): 498.2.

Example 40

[1-({[4-(4-fluorophenyl)piperazin-1-yl]sulfonyl}methyl)hept-2-yn-1-yl]hydroxyformamide (41)

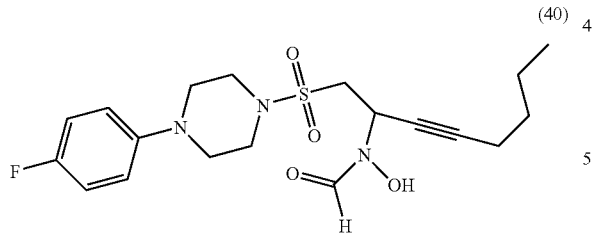

(40)

The title compound was prepared, following procedure described in Example 20, but starting from diethyl({[4-(4-fluorophenyl)piperazin-1-yl]sulfonyl}methyl)phosphonate (prepared in Example 21, step a); 534 mg; 1.35 mmol) and 2-heptyn-1-ol (228 mg; 2.03 mmol), as a beige solid (372 mg, 67% yield). HPLC, Rt: 3.60 min (purity: 97.4%). LC/MS, M⁺(ESI): 412.2, M⁻(ESI): 410.2. ¹H NMR (DMSO-d6) δ: 10.22 (brs, 0.5H), 9.84 (brs, 0.5H), 8.12 (brs, 1H), 7.06 (t, J=8.7 Hz, 2H), 6.97 (dd, J=9.2, 4.7 Hz, 2H), 5.40 (brs, 0.5H), 5.18 (brs, 0.5H), 3.38-3.54 (m, 2H), 3.29 (m, 4H), 3.13 (m, 4H), 2.18 (m, 2H), 1.30-1.45 (m, 4H), 0.84 (t, J=7.0 Hz, 3H).

Example 41

[3-(2-fluorophenyl)-1-({[4-(4-methyloxyphenyl)piperidin-1-yl]sulfonyl}methyl)prop-2-yn-1-yl]hydroxyformamide (41)

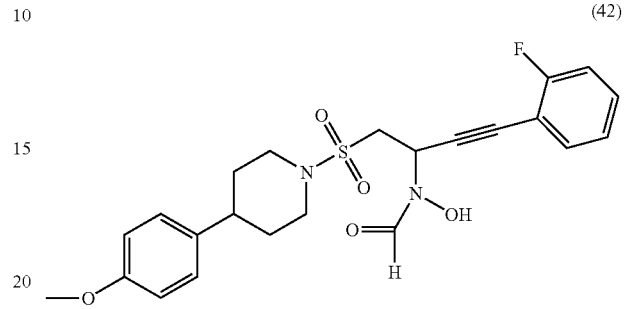

(42)

The title compound was prepared, following procedure described in Example 21, but starting from diethyl({[4-(4-methoxyphenyl)piperidin-1-yl]sulfonyl}methyl)phosphonate (prepared in Example 37, step a); 345 mg; 0.85 mmol), 3-(2-fluorophenyl)pro-2-yn-1-ol (192 mg; 1.28 mmol), as a beige solid (169 mg, 43% yield). HPLC, Rt: 3.99 min (purity: 99.9%). LC/MS, M⁺(ESI): 461.3, M⁻(ESI): 459.1. ¹H NMR (DMSO-d6) δ: 10.42 (brs, 0.5H), 10.0 (brs, 0.5H), 8.30 (m, 1H), 7.57 (m, 1H), 7.47 (m, 1H), 7.31 (t, J=8.7 Hz, 1H), 7.25 (t, J=7.5 Hz, 1H), 7.13 (d, J=8.7 Hz, 2H), 6.83 (d, J=8.7 Hz, 2H), 5.56 (m, 1H), 3.61-3.94 (m, 7H), 2.97 (m, 2H), 2.60 (m, 1H), 1.79 (brd, J=11.3 Hz, 2H), 1.61 (m, 2H).

Example 42

[3-(4-fluorophenyl)-1-({[4-(4-methyloxyphenyl)piperidin-1-yl]sulfonyl}methyl)prop-2-yn-1-yl]hydroxyformamide (42)

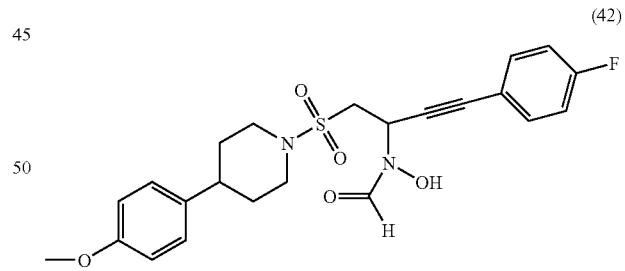

(42)

The title compound (42) was prepared, following procedure described in Example 21, but starting from diethyl({[4-(4-methoxyphenyl)piperidin-1-yl]sulfonyl}methyl)phosphonate (prepared in Example 37, step a); 359 mg; 0.89 mmol), 3-(4-fluorophenyl)pro-2-yn-1-ol (199 mg; 1.33 mmol), as a beige solid (153 mg, 37% yield). HPLC, Rt: 4.03 min (purity: 100%). LC/MS, M⁺(ESI): 461.4, M⁻(ESI) 459.2. ¹H NMR (DMSO-d6) δ: 10.44 (brs, 0.5H), 9.99 (brs, 0.5H), 8.18 (m, 1H), 7.53 (dd, J=8.7, 5.7 Hz, 2H), 7.25 (t, J=9.0 Hz, 2H), 7.13 (d, J=8.7 Hz, 2H), 6.84 (d, J=8.7 Hz, 2H), 5.66 (brs, 0.5H), 5.48 (brs, 0.5H), 3.59-3.94 (m, 7H), 2.92 (m, 2H), 2.60 (m, 1H), 1.79 (brd, J=11.3 Hz, 2H), 1.61 (m, 2H).

Example 43

[1-({[4-(4-chlorophenyl)piperidin-1-yl]sulfonyl}methyl)oct-2-yn-1-yl]hydroxyformamide (43)

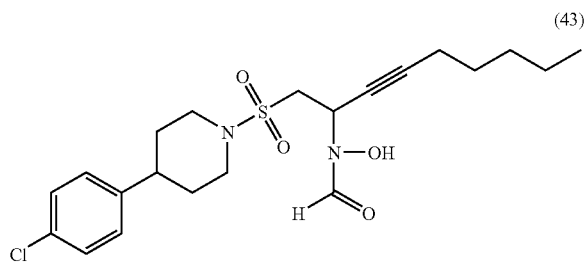

(43)

The title compound was prepared, following the procedure described in Example 13, but starting from 4-(4-chlorophenyl)-1-(methylsulfonyl)piperidine (Intermediate B15; 458 mg; 1.67 mmol) and 2-octynal (0.29 mL; 2.01 mmol), as an white powder (162 mg, 22%). HPLC, Rt: 4.68 min (purity: 94.0%). LC/MS, M$^+$(ESI): 441.3, M$^-$(ESI): 439.2.

Example 44

Hydroxy[1-({[4-(4-methylphenyl)piperidin-1-yl]sulfonyl}methyl)oct-2-yn-1-yl]formamide (44)

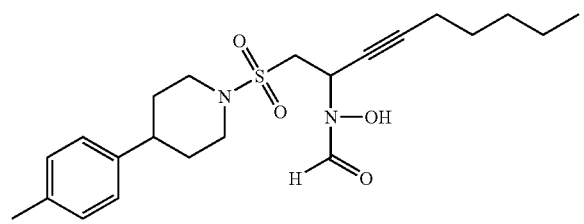

(44)

The title compound was prepared, following the procedure described in Example 13, but starting from 4-(4-methylphenyl)-1-(methylsulfonyl)piperidine (Intermediate B16; 423 mg; 1.67 mmol) and 2-octynal (0.29 mL; 2.01 mmol), as an white powder (246 mg, 35%). HPLC, Rt: 4.64 min (purity: 97.6%). LC/MS, M$^+$(ESI): 421.4, M$^-$(ESI): 419.2.

Example 45

[3-(3-fluorophenyl)-1-({[4-(4-methyloxyphenyl)piperidin-1-yl]sulfonyl}methyl)prop-2-yn-1-yl]hydroxyformamide (45)

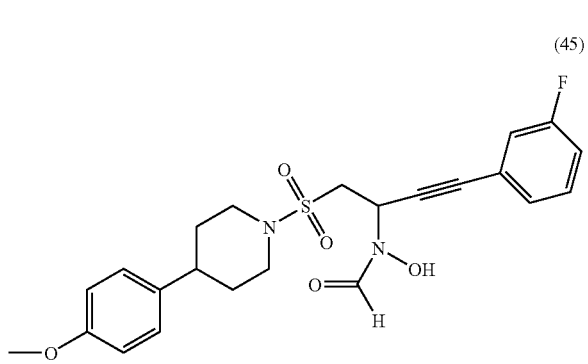

(45)

The title compound was prepared, following procedure described in Example 21, but starting from diethyl({[4-(4-methoxyphenyl)piperidin-1-yl]sulfonyl}methyl)phosphonate (prepared in Example 37, step a); 330 mg; 0.81 mmol), 3-(3-fluorophenyl)pro-2-yn-1-ol (183 mg; 1.22 mmol), as a beige powder (25 mg, 7% yield). HPLC, Rt: 4.04 min (purity: 99.6%). LC/MS, M$^+$(ESI): 461.3, M$^-$(ESI) 459.2. $^1$H NMR (DMSO-d6) δ: 10.46 (brs, 0.5H), 9.96 (brs, 0.5H), 8.18-8.31 (m, 1H), 7.45 (m, 1H), 7.26-7.33 (m, 3H), 7.14 (d, J=8.7 Hz, 2H), 6.84 (d, J=8.7 Hz, 2H), 5.68 (brs, 0.5H), 5.50 (brs, 0.5H), 3.61-4.03 (m, 7H), 2.92 (m, 2H), 2.56 (m, 1H), 1.80 (m, 2H), 1.16 (m, 2H).

Example 46

Hydroxy-1-[({4-[5-(trifluoromethyl)pyridin-2-yl]-1,4-diazepan-1-yl}sulfonyl)methyl]oct-2-yn-1-yl}formamide (46)

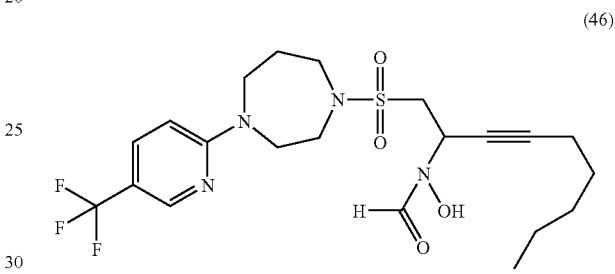

(46)

The title compound was prepared, following the procedure described in Example 13, but starting from 1-(methylsulfonyl)-4-[5-(trifluoromethyl)pyridin-2-yl]-1.4-diazepane (Intermediate B17; 441 mg; 1.36 mmol) and 2-octynal (203 mg; 1.64 mmol), as an white powder (216 mg, 33%). HPLC, Rt: 3.86 min (purity: 100%). LC/MS, M$^+$(ESI): 491.4, M$^-$ (ESI): 489.1.

Example 47

[1-({[4-(4-ethyloxyphenyl)piperazin-1-yl]sulfonyl}methyl)oct-2-yn-1-yl]hydroxyformamide (47)

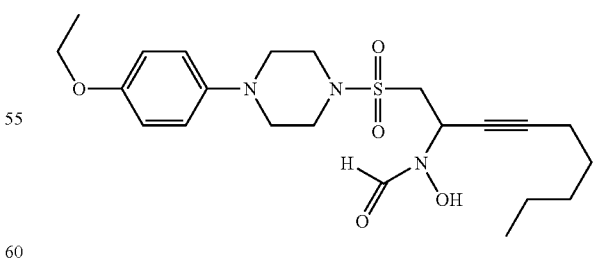

(47)

The title compound was prepared, following the procedure described in Example 13, but starting from 1-(4-ethoxyphenyl)-4-(methylsulfonyl)piperazine (Intermediate B18; 426 mg; 1.5 mmol) and 2-octynal (225 mg; 1.8 mmol), as an white powder (135 mg, 20%). HPLC, Rt: 3.58 min (purity: 98.4%). LC/MS, M$^+$(ESI): 452.3, M$^-$(ESI): 450.3.

Example 48

[1-({[4-(5-bromopyridin-2-yl)piperazin-1-yl]
sulfonyl}methyl)oct-2-yn-1-yl-]hydroxyformamide
(48)

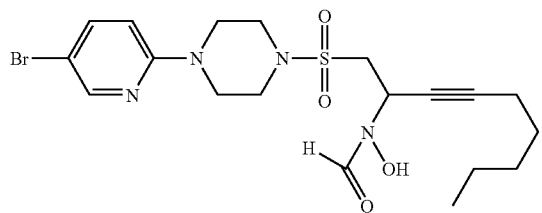

The title compound was prepared, following the procedure described in Example 13, but starting from 1-(5-bromo-pyridin-2-yl)-4-(methanesulfonyl)piperazine (Intermediate B19; 400 mg; 1.25 mmol) and 2-octynal (186 mg; 1.5 mmol), as an white powder (258 mg, 41%). HPLC, Rt: 3.85 min (purity: 99.3%). LC/MS, M$^+$(ESI): 488.9, M$^-$(ESI): 487.9.

Example 49

[1-({[4-(4-fluorophenyl)piperazin-1-yl]
sulfonyl}methyl)-4-morpholin-4-ylbut-2-yn-1-yl]
hydroxyformamide (49)

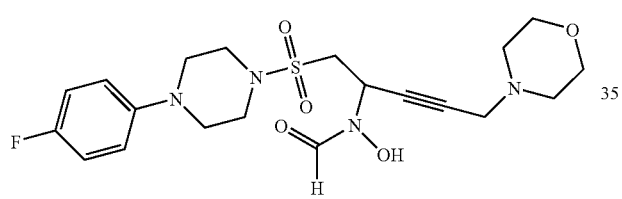

The title compound was prepared, following procedure described in Example 20, but starting from diethyl({[4-(4-fluorophenyl)piperazin-1-yl]sulfonyl}methyl)phosphonate (prepared in Example 21, step a); 558 mg; 1.41 mmol) and 4-morpholin-4-ylbut-2-yn-1-ol 329 mg; 2.12 mmol), as a white powder (67 mg, 58% yield). HPLC, Rt: 1.91 min (purity: 100%). LC/MS, M$^+$(ESI): 455.3. $^1$H NMR (DMSO-d6) δ: 10.35 (brs, 5H), 9.95 (brs, 5H), 8.15 (m, 1H), 6.95-7.09 (m, 4H), 5.45 (brs, 5H), 5.30 (brs, 5H), 3.40-3.60 (m, 6H), 3.27 (m, 6H), 3.14 (m, 4H), 2.43 (m, 4H).

Example 50

[1-({[4-(3-chlorophenyl)piperazin-1-yl]
sulfonyl}methyl)oct-2-yn-1-yl]hydroxyformamide
(50)

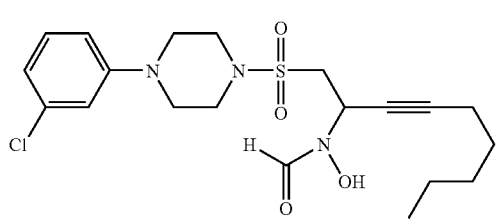

The title compound was prepared, following the procedure described in Example 13, but starting from 1-(3-chlorophenyl)-4-(methylsulfonyl)piperazine (500 mg; 1.8 mmol) and 2-octynal (270 mg; 2.2 mmol), as a white powder (346 mg, 51%). HPLC, Rt: 4.48 min (purity: 99.9%). LC/MS, M$^+$(ESI): 442.1, M$^-$(ESI): 439.8.

Example 51

[1-({[4-(1,3-benzodioxol-5-yl)piperazin-1-yl]
sulfonyl}methyl)oct-2-yn-1-yl]hydroxyformamide
(51)

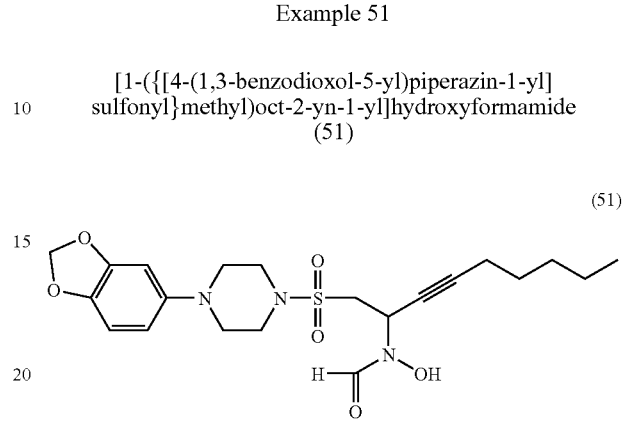

The title compound was prepared, following the procedure described in Example 13, but starting from 1-(1,3-benzodioxol-5-yl)-4-(methylsulfonyl)piperazine (Intermediate B20, 500 mg; 1.76 mmol) and 2-octynal (0.30 mL; 2.11 mmol), as an white powder (184 mg, 23%). HPLC, Rt: 3.78 min (purity: 99.9%). LC/MS, M$^+$(ESI): 452.3, M$^-$(ESI): 450.1.

Example 52 hydroxy[1-({[4-(3-methyloxyphenyl)piperazin-1-yl]
sulfonyl}methyl)-3-phenylprop-2-yn-1-yl]formamide (52)

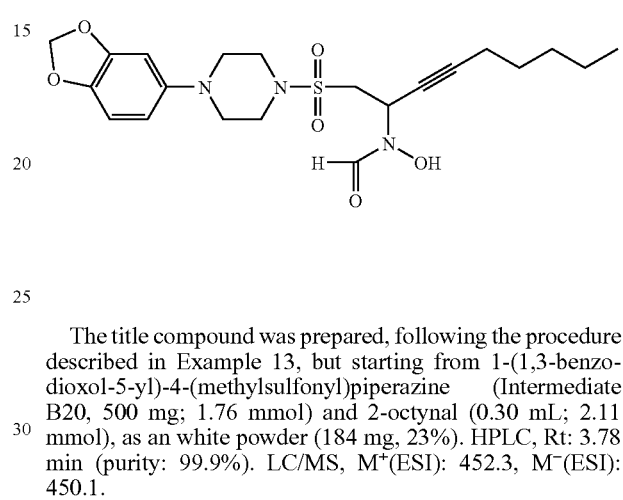

The title compound was prepared, following the procedure described in Example 13, but starting from 1-(3-methoxyphenyl)-4-(methylsulfonyl)piperazine (Intermediate B12; 500 mg; 1.85 mmol) and phenylpropionaldehyde (0.27 mL; 2.22 mmol), as an beige solid (379 mg, 46%). HPLC, Rt: 3.72 min (purity: 97.9%). LC/MS, M$^+$(ESI): 444.4, M$^-$(ESI): 442.2.

Example 53 hydroxy[1-({[4-(4-methylphenyl)piperidin-1-yl]sulfonyl}methyl)-3-phenylprop-2-yn-1-yl]formamide (53)

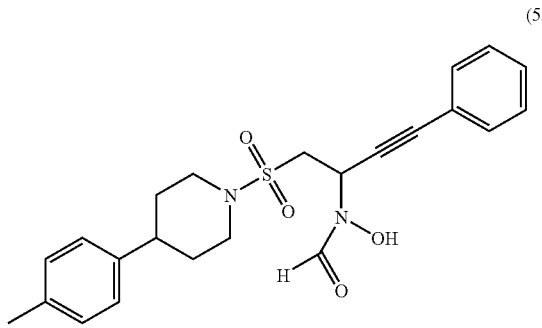

(53)

The title compound was prepared, following the procedure described in Example 13, but starting from 4-(4-methylphenyl)-1-(methylsulfonyl)piperidine (Intermediate B16; 340 mg; 1.34 mmol) and phenylpropionaldehyde (0.20 mL; 1.61 mmol), as an beige solid (252 mg, 44%). HPLC, Rt: 4.20 min (purity: 100%). LC/MS, M$^+$(ESI): 427.4, M$^-$(ESI): 425.3.

Example 54

[1-({[4-(4-chlorophenyl)piperazin-1-yl]sulfonyl}methyl)-3-Phenylprop-2-yn-1-yl]hydroxyformamide (54)

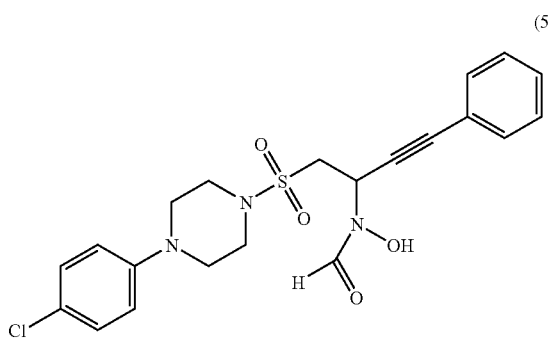

(54)

The title compound was prepared, following the procedure described in Example 13, but starting from 1-(4-chlorophenyl)-4-(methylsulfonyl)piperazine (Intermediate B11; 500 mg; 1.82 mmol) and phenylpropionaldehyde (0.27mL; 2.18 mmol), as an orange solid (445 mg, 55%). HPLC, Rt: 4.20 min (purity: 99.4%). LC/MS, M$^+$(ESI): 448.3, M$^-$(ESI): 446.2.

Example 55

[1-({[4-(4-ethyloxyphenyl)piperazin-1-yl]sulfonyl}methyl)-3-phenylprop-2-yn-1-yl]hydroxyformamide (55)

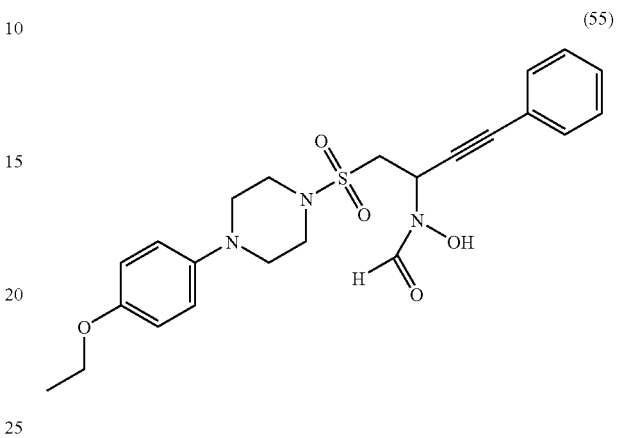

(55)

The title compound was prepared, following the procedure described in Example 13, but starting from 1-(4-ethoxyphenyl)-4-(methylsulfonyl)piperazine (Intermediate B18; 500 mg; 1.76 mmol) and phenylpropionaldehyde (0.26 mL; 2.11 mmol), as an orange solid (265 mg, 32%). HPLC, Rt: 3.22 min (purity: 99.7%). LC/MS, M$^+$(ESI): 458.4, M$^-$(ESI): 456.3.

Example 56

[1-({[4-(5-bromopyridin-2-yl)piperazin-1-yl]sulfonyl}methyl)-2,2-dimethyl-5-phenylpent-4-yn-1-yl]hydroxyformamide (56)

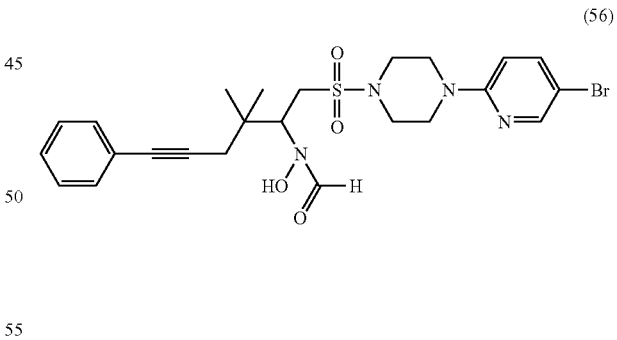

(56)

The title compound was prepared, following procedure described in Example 13, but starting from of 1-(5-bromopyridin-2-yl)-4-methanesulfonylpiperazine (Intermediate B19, 512 mg; 1.60 mmol) and 2,2-dimethyl-5-phenylpent-4-ynal (prepared as described by Cossy et al., 1997, above, 298 mg; 1.60 mmol), as a beige powder (149 mg, 17% yield).HPLC, Rt: 3.94 min (purity: 96.9%). LC/MS, M$^+$(ESI): 551.2. $^1$H NMR (DMSO-d6) δ: 9.98 (s, 0.4H), 9.78 (s, 0.6H), 8.29 (s, 0.4H), 8.19 (m, 1H), 7.95 (s, 0.6H), 7.71 (m, 1H), 7.26-7.36 (m, 5H), 6.85 (m, 1H), 4.73 (d, J=7.9 Hz, 0.4H), 4.04 (d, J=8.7 Hz, 0.6H), 3.57 (m, 4H), 3.39-3.53 (m, 2H), 3.26 (m, 4H), 2.42-2.52 (m, 2H), 1.05 (m, 6H).

Example 57

{2,2-dimethyl-5-phenyl-1-[({4-[4-(trifluoromethyl)phenyl]piperazin-1-yl}sulfonyl)methyl]pent-4-yn-1-yl}hydroxyformamide (57)

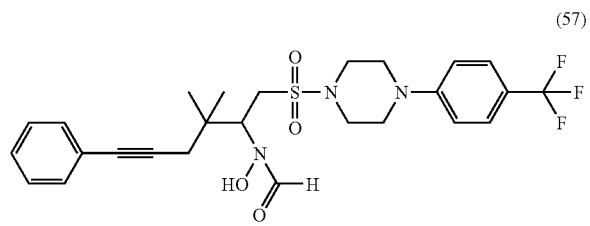

(57)

The title compound was prepared, following procedure described in Example 13, but starting from 1-(methylsulfonyl)-4-[4-(trifluoromethyl)phenyl]piperazine (Intermediate B6, 511 mg; 1.66 mmol) and 2,2-dimethyl-5-phenylpent-4-ynal (prepared as described by Cossy et al., 1997, above, 309 mg; 1.66 mmol), as a beige powder (220 mg, 25% yield). HPLC, Rt: 4.58 min (purity: 92.7%). LC/MS, M+(ESI): 538.5, M−(ESI): 536.4. $^1$H NMR (DMSO-d6) δ: 9.99 (s, 0.3H), 9.79 (s, 0.7H), 8.30 (s, 0.3H), 7.95 (s, 0.7H), 7.50 (m, 2H), 7.25-7.38 (m, 5H), 7.00-7.08 (m, 2H), 4.76 (d, J=8.7 Hz, 0.3H), 4.06 (d, J=8.7 Hz, 0.7H), 3.26-3.55 (m, 10H), 2.37-2.52 (m, 2H), 1.06 (m, 6H).

Example 58

[1-({[4-(5-chloropyridin-2-yl)piperazin-1-yl]sulfonyl}methyl)hex-2-yn-1-yl]hydroxyformamide (58)

Step a) Formation of diethyl({[4-(5-chloropyridin-2-yl)piperazin-1-yl]sulfonyl}methyl)phosphonate

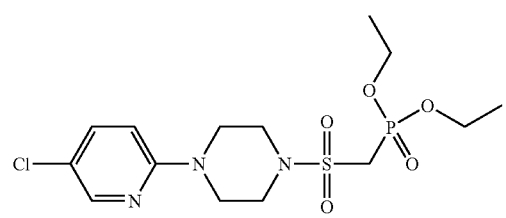

The title compound was prepared, following procedure described in Example 10, step a), but starting from 1-(5-chloropyridin-2-yl)-4-methanesulfonylpiperazine (Intermediate B9; 2.63 g; 9.54 mmol), as yellow powder (2.4 g, 61% yield). HPLC, Rt: 2.58 min (purity: 91.9%). LC/MS, M+(ESI): 412.1, M−(ESI): 410.1. $^1$H NMR (DMSO-d6) δ: 8.09 (d, J=2.3 Hz, 1H), 7.43 (dd, J=9.0, 2.6 Hz, 1H), 6.57 (d, J=9.0 Hz, 1H), 4.23 (m, 4H), 3.62 (m, 4H), 3.51 (d, J=17.3 Hz, 2H), 3.42 (m, 4H), 1.34 (t, J=7.0 Hz, 6H).

Step b) Formation of [1-({[4-(5-chloropyridin-2-yl)piperazin-1-yl]sulfonyl}methyl)hex-2-yn-1-yl]hydroxyformamide

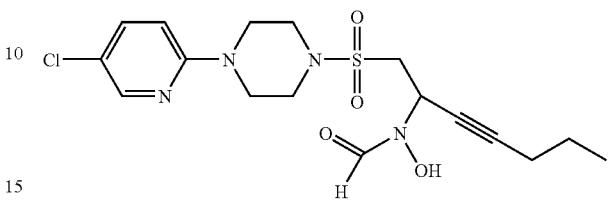

(58)

The title compound (58) was prepared, following procedure described Example 21, but starting from diethyl({[4-(5-chloropyridin-2-yl)piperazin-1-yl]sulfonyl}methyl) phosphonate (485 mg; 1.18 mmol) and 2-hexyn-1-ol (195 µl; 1.77 mmol). Hydrochloride salt was obtained by addition of Et$_2$O/HCl to a solution of the title compound in EtOAc. Filtration of the precipitate gave the compound as a brown powder (228 mg, 43% yield). HPLC, Rt: 2.78 min (purity: 93.0%). LC/MS, M+(ESI): 415.3, M−(ESI): 413.1. $^1$H NMR (DMSO-d6) δ: 10.3 (brs, 1H), 8.15 (brs, 1H), 8.12 (d, J=2.2 Hz, 1H), 7.63 (dd, J=9.0, 2.6 Hz, 1H), 6.93 (d, J=9.0 Hz, 1H), 5.12-5.60 (brm, 2H), 3.59 (m, 4H), 3.16-3.41 (m, 6H), 2.13 (m, 2H), 1.43 (m, 2H), 0.89 (t, J=7.2 Hz, 3H). CHN analysis: [C$_{17}$H$_{23}$N$_4$O$_4$ClS-HCl]calculated: C, 45.24%; H, 5.36%; N, 12.41%. Found: C, 45.04%; H, 5.59%; N, 12.40%.

Example 59

[1-({[4-(4-ethyloxyphenyl)piperazin-1-yl]sulfonyl}methyl)-2,2-dimethyl-5-phenylpent-4-yn-1-yl]hydroxyformamide (59)

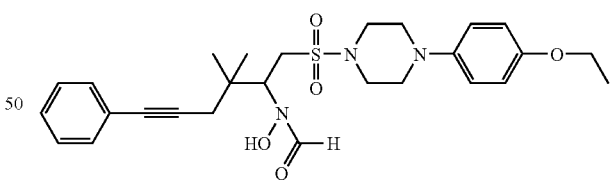

(59)

The title compound was prepared, following procedure described in Example 13, but starting from 1-(4-ethoxyphenyl)-4-(methylsulfonyl)piperazine (Intermediate B18, 457 mg; 1.61 mmol) and 2,2-dimethyl-5-phenylpent-4-ynal (prepared as described by Cossy et al., 1997, above, 299 mg; 1.61 mmol), as a white powder (40 mg, 4% yield). HPLC, Rt: 3.63 min (purity: 100%). LC/MS, M+(ESI): 514.5, M−(ESI): 512.3. $^1$H NMR (DMSO-d6) δ: 9.96 (brs, 1H), 8.30 (s, 0.3H), 7.95 (s, 0.7H), 7.31-7.40 (m, 5H), 6.80-6.90 (m, 4H), 4.30 (brs, 2H), 3.94 (d, J=6.9 Hz, 0.3H), 4.05 (d, J=7.9 Hz, 0.7H), 4.73 (qd, J=9.0 Hz, 2H), 3.43 (m, 2H), 3.32 (m, 4H), 3.06 (m, 4H), 2.48-2.51 (m, 2H), 1.28 (t, J=6.9 Hz, 3H), 1.07 (m, 6H).

Example 60

[1-({[4-(3,4-dimethyloxyphenyl)piperazin-1-yl]sulfonyl}methyl)oct-2-yn-1-yl]hydroxyformamide (60)

(60)

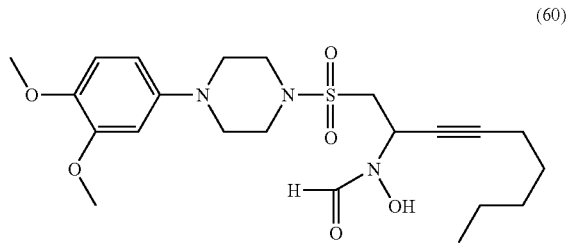

The title compound was prepared, following the procedure described in Example 13, but starting from 1-(3,4-dimethoxyphenyl)-4-(methylsulfonyl)piperazine (Intermediate B21; 450 mg; 1.50 mmol) and 2-octynal (0.26 mL; 1.81 mmol), as a pink powder (110 mg, 13%). HPLC, Rt: 3.14 min (purity: 99.6%). LC/MS, M$^+$(ESI): 468.4, M$^-$(ESI): 466.3.

Example 61

[1-({[4-(4-ethyloxyphenyl)-1,4-diazepan-1-yl]sulfonyl}methyl)oct-2-yn-1-yl]hydroxyformamide (61)

(61)

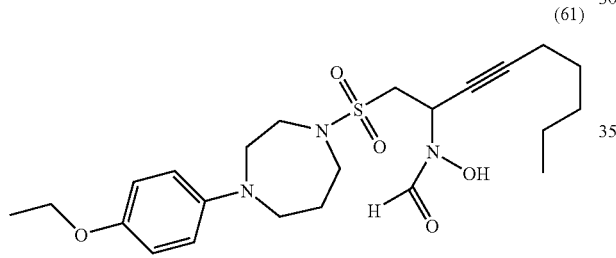

The title compound was prepared, following the procedure described in Example 13, but starting from 1-(4-ethoxyphenyl)-4-(methylsulfonyl)-1,4-diazepane (Intermediate B22; 141 mg; 0.47 mmol) and 2-octynal (0.08 mL; 0.57 mmol), as an orange powder (24 mg, 11%). HPLC, Rt: 3.36 min (purity: 76.4%). LC/MS, M$^+$(ESI): 466.5, M$^-$(ESI): 464.4.

Example 62

[1-({[(2R)-4-(4-fluorophenyl)-2-methylpiperazin-1-yl]sulfonyl}methyl)oct-2-yn-1-yl]hydroxyformamide (62)

(62)

Chiral

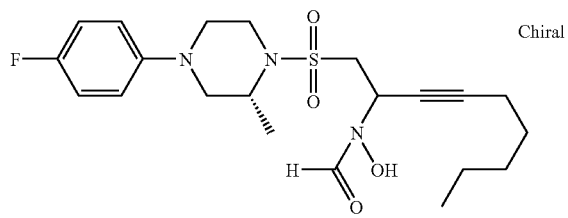

The title compound was prepared, following the procedure described in Example 13, but starting from (2R)-4-(4-fluorophenyl)-2-methyl-1-(methylsulfonyl)piperazine (Intermediate B23; 460 mg; 1.69 mmol) and 2-octynal (0.29 mL; 2.03 mmol), as an orange powder (282 mg, 38%). HPLC, Rt: 4.45 min (purity: 99.4%). LC/MS, M$^+$(ESI): 440.4, M$^-$(ESI): 438.3.

Example 63

[1-({[4-(4-fluorophenyl)piperazin-1-yl]sulfonyl}methyl)-2,2-dimethyl pent-4-yn-1-yl]hydroxyformamide (63)

(63)

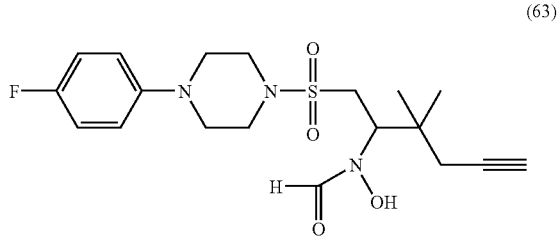

The title compound was prepared, following procedure described in Example 1, but starting from 1-(4-fluorophenyl)-4-(methylsulfonyl)piperazine (Intermediate B1; 411 mg; 1.59 mmol) and 2,2-dimethylpent-4-ynal (prepared as described by Rigby et al., 2004, *J. Org. Chem.*, 69(20), 6751-6760, 175 mg; 1.59 mmol), as a yellow powder (24 mg, 4% yield). HPLC, Rt: 3.00 min (purity: 100%). LC/MS, M$^+$(ESI): 412.3, M$^-$(ESI): 410.3. $^1$H NMR (DMSO-d6) δ: 8.33 (s, 0.2H), 7.89 (s, 0.8H), 6.76-7.12 (m, 4H), 4.65 (brd, 0.2H), 4.20 (d, J=8.7 Hz, 0.8H), 3.56 (m, 1H), 3.26 (m, 4H), 3.02 (m, 4H), 2.92 (m, 1H), 2.12 (m, 2H), 1.97 (m, 1H), 0.95 (m, 6H).

Example 64

[1-({[4-(4-fluorophenyl)piperazin-1-yl]sulfonyl}methyl)-4-pyrrolidin-1-ylbut-2-yn-1-yl]hydroxyformamide (64)

(64)

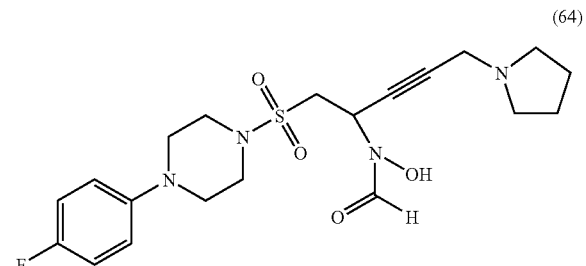

The title compound was prepared, following procedure described in Example 21, but starting from diethyl({[4-(4-fluorophenyl)piperazin-1-yl]sulfonyl}methyl)phosphonate (prepared in Example 21, step a), 351 mg; 0.89 mmol), 4-pyrrolidin-1-ylbut-2-yn-1-ol (prepared as described by Bieber et al., 2004, *Tetrahedron Letters*, 45(45); 8281-8283, 186 mg; 1.34 mmol), as an orange oil (9 mg, 2% yield). HPLC, Rt: 1.87 min (purity: 91.8%). LC/MS, M$^+$(ESI): 439.5.

Example 65

[1-({[4-(4-fluorophenyl)piperazin-1-yl]sulfonyl}methyl)-2,2-dimethyl-6-morpholin-4-yl-hex-4-yn-1-yl]hydroxyformamide (65)

Step a) Formation of 4-[7-{[4-(4-fluorophenyl)piperazin-1-yl]sulfonyl}-6-(hydroxyamino)-5,5-dimethyl-hept-2-yn-1-yl]morpholine

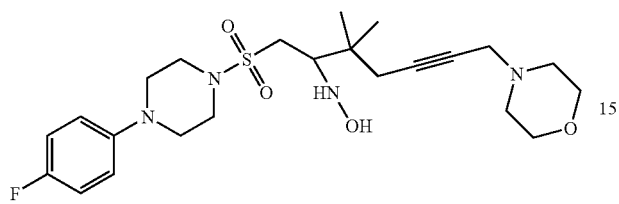

The title compound was prepared, following procedure described in Example 36, step a), but starting from 1-(4-fluorophenyl)-4-(methylsulfonyl)piperazine (Intermediate B1, 380 mg; 1.45 mmol) and 2,2-dimethyl-6-morpholin-4-ylhex-4-ynal (Intermediate A6, 303 mg) as a white powder (250 mg, 36% yield). HPLC, Rt: 2.20 min (purity: 98.2%). LC/MS, M⁺(ESI): 483.6.

Step b) Formation of [1-({[4-(4-fluorophenyl)piperazin-1-yl]sulfonyl}methyl)-2,2-dimethyl-6-morpholin-4-ylhex-4-yn-1-yl]hydroxyformamide (65)

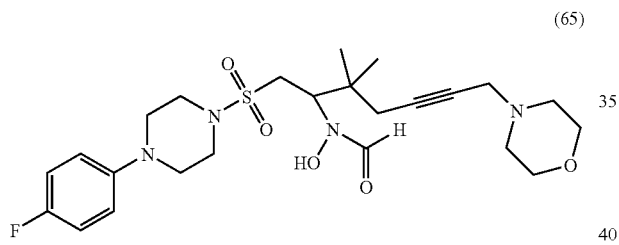

The title compound (65) was prepared, following procedure described in Example 1, step c), but starting from 4-[7-{[4-(4-fluorophenyl)piperazin-1-yl]sulfonyl}-6-(hydroxyamino)-5,5-dimethylhept-2-yn-1-yl]morpholine (250 mg, 0.52 mmol) as a white powder (100 mg, 38% yield). ¹H NMR (DMSO-d6) δ: HPLC, Rt: 2.34 min (purity: 93.8%). LC/MS, M⁺(ESI): 511.4, M⁻(ESI): 509.3.

Example 66

[1-({[4-(4-fluorophenyl)piperazin-1-yl]sulfonyl}methyl)-2,2-dimethyl hept-4-yn-1-yl]hydroxyformamide (66)

Step a) Formation of 1-{[(1E)-3,3-dimethyloct-1-en-5-yn-1-yl]sulfonyl}-4-(4-fluoro phenyl)piperazine

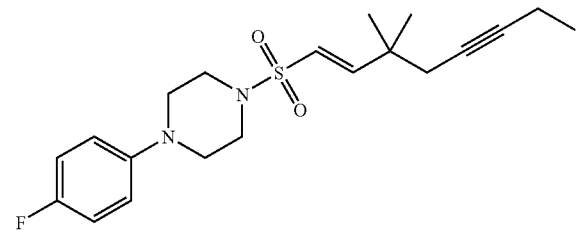

The title compound was prepared, following procedure described in Example 1, step a), but starting from 1-(4-fluorophenyl)-4-(methylsulfonyl)piperazine (Intermediate B1, 855 mg; 3.31 mmol) and of 2,2-dimethyl-hept-4-ynal, 457 mg; 3.31 mmol), as a white powder (764 mg, 61% yield). HPLC, Rt: 4.75 min (purity: 97.7%). LC/MS, M⁺(ESI): 379.4, ¹H NMR (DMSO-d6) δ: 6.97-6.82 (m, 4H), 6.74 (d, J=15.4 Hz, 1H), 6.07 (d, J=14.9 Hz, 3.26 (m, 4H), 3.15 (m, 4H), 2.21 (m, 2H), 2.01-2.16 (m, 2H), 1.15 (s, 6H), 1.06 (t, J=7.4 Hz, 3H).

Step b) Formation of 1-(4-fluorophenyl)-4-{[2-(hydroxyamino)-3,3-dimethyloct-5-yn-1-yl]sulfonyl}piperazine

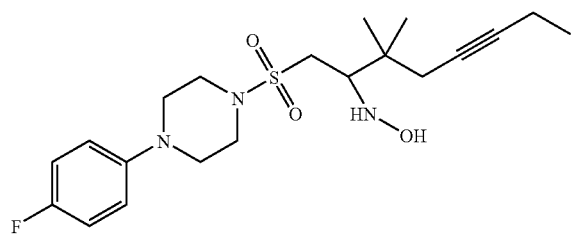

The title compound was prepared, following procedure described in Example 1, step b), but starting from 1-{[(1E)-3,3-dimethyloct-1-en-5-yn-1-yl]sulfonyl}-4-(4-fluorophenyl)piperazine (760 mg; 2.01 mmol), as a beige oil (836 mg, quantitative). HPLC, Rt: 3.49 min (purity: 95.0%). LC/MS, M⁺(ESI): 412.4.

Step c) Formation of [1-({[4-(4-fluorophenyl)piperazin-1-yl]sulfonyl}methyl)-2,2-dimethylhept-4-yn-1-yl]hydroxyformamide (66)

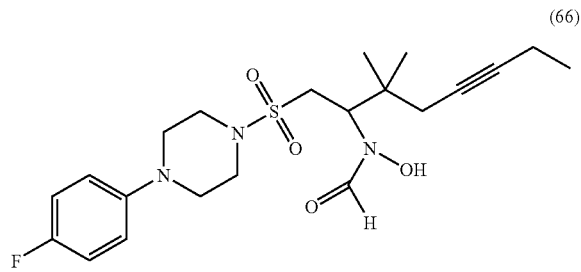

The title compound was prepared, following procedure described in Example 1, step c), but starting from 1-(4-fluorophenyl)-4-{[2-(hydroxyamino)-3,3-dimethyloct-5-yn-1-yl]sulfonyl}piperazine (836 mg; 2.03 mmol), as a white solid (241 mg, 27% yield). HPLC, Rt: 3.82 min (purity: 93.6%). LC/MS, M⁺(ESI): 440.6, M⁻(ESI): 438.5. ¹H NMR (DMSO-d6) δ: 9.93 (s, 0.3H), 9.71 (s, 0.7H), 8.26 (s, 0.3H), 8.26 (s, 0.7H), 6.95-7.90 (m, 4H), 4.60 (d, J=9.0 Hz, 0.3H), 3.96 (d, J=8.7 Hz, 0.7H), 3.35-3.98 (m, 6H), 3.15 (m, 4H), 2.15 (m, 4H), 1.04 (t, J=7.2 Hz, 3H), 0.98 (m, 6H).

According to a further general process, compounds of Formula (I) and its precursors of Formulae (II) to (XII) can be converted to alternative compounds of Formula (I) respectively, employing suitable interconversion techniques well known by a person skilled in the art.

If the above set of general synthetic methods are not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999. Those skilled in the art will recognize that certain reactions are best carried out when potentially reactive functionality on the molecule is masked or protected, thus avoiding side reactions and/or increasing the yield of the reaction. Examples of protecting group moieties may be found in Philip J. Kocienski, 1994 above and in Greene et al., 1999, above. The need and choice of protecting groups for a particular reaction is known to those skilled in the art and depends on the nature of the functional group to be protected (hydroxy, amino, carboxy, etc.), the structure and the stability of the molecule of which the substituent is part of the reaction conditions.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

Biological Assays:

The compounds of the present invention may be subjected to the following assays:

Example 67

Enzyme Inhibition Assays

Compounds of the invention were tested to assess their activities as inhibitors of MMP-1, MMP-2, MMP-9 and MMP-12.

MMP-9 Assay Protocol

Compounds of the invention were tested for inhibitory activity against 92 kDa gelatinase (MMP-9) in an assay using a coumarin-labeled peptide substrate, (7-methoxycoumarin-4-yl)acetyl-Pro-Leu-Gly-Leu-(3-[2,4-dinitrophenyl]-L-2, 3diaminopropionyl)-Ala-Arg-NH2 (McaPLGLDpaAR) (Knight et al, 1992, *FEBS Lett.*, 263-266).

Stock solutions were made up as follows: Assay Butter: 100 mM Tris-HCl pH 7.6 containing 100 mM NaCl, 10 mM $CaCl_2$, and 0.05% Brij 35.

Substrate: 0.4 mM McaPLGLDpaAR (from Bachem) (0.437 mg/ml) stock solution in 100% DMSO (stored at $-20°$ C.). Dilute to 8 µM in assay butter.

Enzyme: Recombinant human 92 kDa gelatinase (MMP-9; APMA (4-aminophenyl mercuric acetate)—activated if necessary) appropriately diluted in assay butter.

Test Compounds were prepared initially as 10 mM compound solution in 100% DMSO, diluted to 1 mM in 100% DMSO, then serially diluted 3-fold in 100% DMSO across columns 1-10 of a 96-well microtitre plate Assay concentration range, 100 µM (column 1) to 5.1 nM (column 10).

The assay was performed in a total volume of 100 µL per well in 96-well microtitre plates. Activated enzyme (20 µL) was added to the wells followed by 20 µL of assay butter. Appropriate concentrations of test compounds dissolved in 10 µL of DMSO were then added followed by 50 µL of McaPLGLDpaAR (8 µM, prepared by dilution of DMSO stock in assay butter). For each as say ten concentrations of test compound were examined in duplicate. Control wells lack either enzyme or test compound. The reactions were incubated at 37° C. for 2 hours. The fluorescence at 405 nm was measured immediately with an SLT Fluostar fluorometer (SL T Labinstruments GmbH, Grödig, Austria) using 320 nm excitation, without stopping the reaction.

The effect of the test compound was determined from the dose response curve generated by the 10 duplicate concentrations of inhibitor. The $IC_{50}$ (the concentration of compound required to give a 50% decrease in enzyme activity) was obtained by fitting data to the equation, $Y=a+((b-a)/(1+(c/X)^d))$. (Y=inhibition achieved for a particular dose; X=the dose in nM; a=minimum y or zero % inhibition; b=maximum y or 100% inhibition; c=is the $IC_{50}$; d=is the slope). The result was rounded to one significant figure.

MMP-12 Assay Protocol

Compounds of the invention were tested for inhibitory activity against metalloelastase (MMP-12) in an assay using a coumarin-labelled peptide substrate, (7-methoxycoumarin-4-yl)acetyl-Pro-Leu-Gly-Leu-(3-[2,4dinitrophenyl]-L-2,3-diaminopropionyl)-Ala-Arg-NH2 (McaPLGLDpaAR) (Knight et al, 1992, above). The protocol for this assay was as described for the MMP-9 assay above.

MMP-1Assay Protocol

Compounds of the invention were tested for inhibitory activity against collagenase (MMP-1) in an assay using a coumarin-labelled peptide substrate, (7-methoxycoumarin-4-yl)acetyl-Pro-Leu-Gly-Leu-(3-[2,4-dinitrophenyl]-L-2, 3diaminopropionyl)-Ala-Arg-NH2 (McaPLGLDpaAR) (Knight et al, 1992, above). The protocol for this assay was as described for the MMP-9 assay above.

MMP-2 Assay Protocol

Compounds of the invention were tested for inhibitory activity against gelatinase B (MMP-2) in an assay using a coumarin-labelled peptide substrate, (7-methoxycoumarin-4-yl)acetyl-Pro-Leu-Gly-Leu-(3-[2,4-dinitrophenyl]-L-2, 3diaminopropionyl)-Ala-Arg-NH2 (Mca PLGLDpaAR) (Knight et al, 1992, above). The protocol for this assay was as described for the MMP-9 assay above.

The results are expressed in terms of $IC_{50}$ (the concentration of compound required to give a 50% decrease in enzyme activity) and are presented in Table 1 below:

TABLE 1

| | $IC_{50}$ on different MMPs: | |
|---|---|---|
| Examples | MMP-1 $IC_{50}$ (nM) | MMP-12 $IC_{50}$ (nM) |
| Example 1 | >5000 | 46 |
| Example 4 | >5000 | 58 |
| Example 6 | >5000 | 21 |
| Example 7 | >5000 | 20 |
| Example 9 | >5000 | 48 |
| Example 10 | >5000 | 33 |
| Example 19 | >5000 | 18 |
| Example 27 | >5000 | 95 |
| Example 36 | >5000 | 20 |

TABLE 1-continued

IC$_{50}$ on different MMPs:

| Examples | MMP-1 IC$_{50}$ (nM) | MMP-12 IC$_{50}$ (nM) |
|---|---|---|
| Example 37 | >5000 | 6 |
| Example 61 | >5000 | 24 |
| Example 64 | >5000 | 40 |

Example 68

IL-2-Induced Peritoneal Recruitment of Lymphocytes

Administration of IL-2 intraperitoneally causes migration of lymphocytes into the intraperitoneal cavity. This is a model for the cellular migration that occurs during inflammation.
Protocol C3H/HEN mice (Elevage Janvier, France) were intraperitoneally injected with IL-2 (Serono Pharmaceutical Research Institute, 20 µg/kg, in saline).

Compounds of the invention were suspended in 0.5% carboxymethylcellulose (CMC)/0.25% tween-20 and were administered by s.c. or p.o. route (10 ml/kg) 15 min prior to administration of IL-2.

Twenty-four hours after administration of IL-2, peritoneal white blood cells were collected by 3 successive lavages of the peritoneal cavity with 5 ml phosphate buffered saline (PBS)-1 mM EDTA (+4° C.). The suspension was centrifuged (1700 g×10 min at +4° C.). The resulting pellet was suspended in 1 ml PBS-1 mM EDTA.

Lymphocytes were identified and counted using a Beckman/Coulter counter.
Experimental Design The animals were divided into 6 groups (6 mice each group):
Group 1: (baseline) received 0.5% CMC/0.25% tween-20 (vehicle of compound of the invention) and saline (vehicle of IL-2);
Group 2: (control IL-2) received 0.5% CMC/0.25% tween-20 and injection of IL-2;
Group 3: Experimental group (Compound of the invention Dose 1) received a compound of the invention and injection of IL-2;
Group 4: Experimental group (Compound of the invention Dose 2) received a compound of the invention and injection of IL-2;
Group 5: Experimental group (Compound of the invention Dose 3) received a compound of the invention and injection of IL-2;
Group 6: Reference group received reference compound dexamethasone and injection of IL-2.
Calculation Inhibition of lymphocyte recruitment was calculated as follows:

$$\% \text{ inhibition} = \frac{1 - (LyX - Ly1)}{(Ly2 - Ly1)} \times 100\%$$

Where Ly 1=Number of lymphocytes in group 1 (E3/µl), Ly 2=Number of lymphocytes in group 2 (E3/µl), Ly X=Number of lymphocytes in group X (3-5) (E3/µl).

The ED$_{50}$ (the concentration of compound required to result in 50% of the inhibitory activity) are calculated and presentated in Table 2 below.

TABLE 2

ED$_{50}$ in IL-2-induced peritoneal recruitment of lymphocytes model:

| Examples | ED$_{50}$ (mg/kg) | Route |
|---|---|---|
| Example 1 | 0.8 | po |
| Example 7 | 2 | po |

Example 68

Chronic Obstructive Pulmonary Disease (COPD) Model

Compounds of the invention can be evaluated for their ability to prevent cigarette smoke-induced COPD.

Female AJ mice (Harlan, 17-25 g) are exposed daily to cigarette smoke (CS) for 11 consecutive days in groups of 5, in individual clear chambers. Animals are weighed prior to treatment, on day 6 of exposure and on day 12. The CS was generated using 1R1 cigarettes purchased from the Institute of Tobacco Research, University of Kentucky, USA and is allowed to enter the chambers at a flow rate of 100 ml/min.

In order to minimise any potential problems caused by repeated exposure to a high level of daily CS, the exposure of the mice to TS is increased gradually over the time to a maximum of 6 cigarettes from day 5 to day 11 (approximately 48 min exposure).

A sham group of mice is also exposed to air on a daily basis for equivalent lengths of time as controls (no CS exposure).
Treatment Compounds of the invention are prepared in 0.5% carboxymethylcellulose Na salt (CMC, Sigma reference C-4888) as vehicle.

Animals are orally dosed twice daily by gavage in a dose volume of 5 ml/kg, 1 h prior to air or CS exposure and 6 h after the cessation of the exposure.

Sham animals (n=10) received vehicle and are exposed to air for up to a maximum of 50 minutes per day. The control group (n=10) received vehicle and is exposed to CS (up to a maximum of 6 cigarettes per day). Additional groups are exposed to CS (from up to a maximum of 6 cigarettes per day) and treated with one of the test compounds or the reference compound.
Bronchoalveolar Lavage and Cytospin Analysis Twenty-four hours after the last CS exposure, bronchoalveolar lavage is performed as follows:

The trachea is dissected under deep anesthesia (sodium pentobarbitone) and cannulated using a Portex nylon intravenous cannula shortened to approximately 8 mm. Phosphate buffered saline (PBS, Gibco) containing 10 units/ml heparin (0.4 ml) is gently instilled and withdrawn 3 times. The lavage fluid is placed in an Eppendorf tube and kept on ice prior to subsequent determinations. Then, lavage fluid is separated from cells by centrifugation. The supernatant is removed and frozen for subsequent analysis. The cell pellet is resuspended in PBS and total cell numbers were calculated by counting a stained aliquot (Turks stain) under a microscope using a haemocytometer.

Differential cell count is then performed as follows: The residual cell pellet is diluted to approximately 105 cells per ml. A volume of 500 µl is placed in the funnel of a cytospin slide and was centrifuged for 8 min at 800 rpm. The slide is air-dried and stained using 'Kwik-Diff' solutions (Shandon) following purchaser instructions. Slides are dried and cover-slipped and differential cell count is done using light microscopy. Up to 400 cells are counted for each slide. Cells were differentiated using standard morphometric techniques.

Statistical Analysis

The mean+/−S.D. is calculated for each experimental group. Results are analyzed using a one-way analysis of variance (ANOVA), followed by a Bonferroni correction for multiple comparisons. Statistical significance is considered with $p<0.05$.

Example 69

Experimental Allergic Encephalomyelitis (EAE) Model

Compounds according to the invention can be evaluated for their activity in a model for multiple sclerosis in mice.

Animals

C57BL/6NCrlBR female mice are used. Mice are kept in wire cages (cm 32×14×13 h) with stainless steel feeders and fed on a standard diet (4RF21, Charles River, Italy) and water ad libitum. From day 7, wet pellets are also placed every day on the bottom of the cage. Plastic is bottles are used in addition to the automatic water system.

Experimental Procedure

Mice are immunized (day=0) by injecting s.c. in the left flank 0.2 ml of an emulsion composed of 200 µg $MOG_{35-55}$ peptide (Neosystem, Strasbourg, France) in Complete Freund's Adjuvant (CFA, Difco, Detroit, U.S.A.) containing 0.5 mg of *Mycobacterium tuberculosis*. Immediately after, they receive an i.p. injection of 500 ng pertussis toxin (List Biological Lab., Campbell, Calif., U.S.A.) dissolved in 400 µL of buffer (0.5 M NaCl, 0.017% Triton X-100, 0.015 M Tris, pH=7.5). On day 2, the animals are given a second injection of 500 ng pertussis toxin.

On day 7, the mice receive a second dose of 200 µg of $MOG_{35-55}$ peptide in CFA injected s.c. in the right flank. Starting approximately from day 8-10, this procedure results in a progressing paralysis, arising from the tail and ascending up to the forelimbs.

Animals are individually weighed and are examined for the presence of paralysis that is scored according to the following score-system (1):
0=no signs of disease
0.5=partial tail paralysis
1=tail paralysis
1.5=tail paralysis+partial unilateral hindlimb paralysis
2=tail paralysis+bilateral hindlimb weakness or partial paralysis
2.5=tail paralysis+partial hindlimb paralysis (lowered pelvi)
3=tail paralysis+complete hindlimb paralysis
3.5=tail paralysis+hindlimb paralysis+incontinence
4=tail paralysis+hindlimb paralysis+weakness or partial paralysis of forelimbs
5=moribund or dead Mortality and clinical signs are monitored daily in each group of treatment, by a technician who is unaware of treatments.

Daily treatment with compounds, their vehicle or with a reference compound starts on day 7 and continued for 15 or 21 consecutive days in all groups.

Histopathological Examination

At the end of the treatment period, each animal is anesthetised with sodium pentobarbital and is transcardially perfused-fixed with 4% paraformaldehyde via the left ventricle. Fixed spinal cords are then carefully dissected out.

Spinal cord slices are embedded in paraffin blocks. Sectioning and staining with hematoxylin and eosin and CD45 staining for inflammation, and with Kluver-PAS (Luxol fast blue plus Periodic Acid Schiff staining) and Bielchowski's staining for the detection of demyelination and axonal loss, are performed.

In the spinal cord, the total area of all slices is measured for each animal as points of intersection of a 10×10 grid at a magnification of 0.4×0.4 mm per grid. The perivascular inflammatory infiltrates are counted in each slice in order to obtain a total value for each animal and evaluated as number of infiltrates per $mm^2$. Demyelination and axonal loss areas are measured for each animal as points of intersection of 10×10 grid at a magnification of 0.1×0.1 mm per grid and are expressed as a percentage of total demyelination area over the total area of the slices.

Data Evaluation and Statistical Analysis

The results of clinical and histopathological observations are expressed as the mean (±SEM) scores in each treatment group. Values obtained in the test drug-treated groups are compared with that of the positive control group. Significance of differences among groups relating to clinical score are analysed by one-way ANOVA, followed in case of significance ($p<0.05$) by Fisher test.

Differences among groups for the presence of perivascular inflammatory infiltrates and the extent of demyelination and axonal loss in the spinal cord as well as body weight data are analysed by one-way ANOVA, followed in case of significance ($p<0.05$) by Fisher test.

Example 70

Preparation of a Pharmaceutical Formulation

The following formulation examples illustrate representative pharmaceutical compositions according to the present invention being not restricted thereto.

Formulation 1—Tablets

A compound of the invention is admixed as a dry powder with a dry gelatin binder in an approximate 1:2 weight ration. A minor amount of magnesium stearate is added as a lubricant. The mixture is formed into 240-270 mg tablets (80-90 mg) of active sulfonyl amino cyclic derivative per tablet) in a tablet press.

Formulation 2—Capsules

A compound of the invention is admixed as a dry powder with a starch diluent in an approximate 1:1 weight ratio. The mixture is filled into 250 mg capsules (125 mg of active sulfonyl amino cyclic derivative per capsule).

Formulation 3—Liquid

A compound of the invention (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active sulfonyl amino cyclic derivative) in a tablet press.

Formulation 5—Injection

A compound of the invention is dissolved in a buffered sterile saline injectable aqueous medium to a concentration of approximately 5 mg/ml.

The invention claimed is:
1. A sulfonyl amino cyclic derivative according to the Formula:

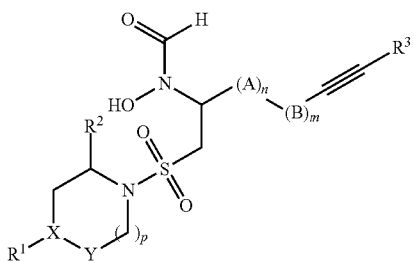

wherein:
A is $CR^4R^5$;
B is $CR^{4'}R^{5'}$;
$R^1$ is selected from aryl, heteroaryl, $C_3$-$C_8$-cycloalkyl and heterocycloalkyl;
$R^2$ is selected from H, $C_1$-$C_6$-alkyl, $C_2$-$C_6$-alkenyl and $C_2$-$C_6$-alkynyl;
$R^3$ is selected from H, —Si($C_1$-$C_6$-alkyl)$_3$, amino-$C_1$-$C_6$-alkyl, $C_1$-$C_6$-alkyl, aryl, heteroaryl, aryl-$C_1$-$C_6$-alkyl, heteroaryl-$C_1$-$C_6$-alkyl, $C_3$-$C_8$-cycloalkyl-$C_1$-$C_6$-alkyl, heterocycloalkyl-$C_1$-$C_6$-alkyl, $C_3$-$C_8$-cycloalkyl and heterocycloalkyl;
$R^4$, $R^5$, $R^{4'}$ and $R^{5'}$ are independently selected from H, halogen, $C_1$-$C_6$-alkyl, $C_2$-$C_6$-alkenyl and $C_2$-$C_6$-alkynyl;
X is N;
Y is $CH_2$;
the group —X—Y— is —N—$CH_2$—;
m is selected from 0, 1 and 2;
n is selected from 0 and 1; and
p is 1;
or an enantiomer, diastereomer, or a pharmaceutically acceptable salt thereof.

2. A sulfonyl amino cyclic derivative according to claim 1, wherein $R^1$ is aryl.

3. A sulfonyl amino cyclic derivative according to claim 2, wherein $R^1$ is phenyl.

4. A sulfonyl amino cyclic derivative according to claim 1, wherein $R^1$ is heteroaryl.

5. A sulfonyl amino cyclic derivative according to claim 1, wherein $R^2$ is H or methyl.

6. A sulfonyl amino cyclic derivative according to claim 1, wherein $R^3$ is selected from aryl and heteroaryl.

7. A sulfonyl amino cyclic derivative according to claim 1, wherein $R^3$ is selected from $C_1$-$C_6$-alkyl, aryl-$C_1$-$C_6$-alkyl, heteroaryl-$C_1$-$C_6$-alkyl, $C_3$-$C_8$-cycloalkyl-$C_1$-$C_6$-alkyl and heterocycloalkyl-$C_1$-$C_6$-alkyl.

8. A sulfonyl amino cyclic derivative according to claim 1, wherein $R^3$ is H.

9. A sulfonyl amino cyclic derivative according to claim 1, wherein n is 0.

10. A sulfonyl amino cyclic derivative according to claim 1, wherein m is 0.

11. A sulfonyl amino cyclic derivative according to claim 1, wherein m and n are 1.

12. A sulfonyl amino cyclic derivative according to claim 1, wherein $R^1$ is selected from aryl and heteroaryl; and $R^2$ is H or methyl.

13. A sulfonyl amino cyclic derivative according to claim 12 wherein A is $C(CH_3)_2$; B is $CH_2$; and both m and n are 1.

14. A sulfonyl amino cyclic derivative selected from the group consisting of:
3-(1,3-benzodioxol-5-yl)-1-({[4-(4-fluorophenyl)-1-piperazinyl]sulfonyl}methyl)-2-propynyl(hydroxy)formamide;
1-({[4-(4-fluorophenyl)-1-piperazinyl]sulfonyl}methyl)-3-(trimethylsilyl)-2-propynyl(hydroxy)formamide;
hydroxy[1-{[(4-pyridin-2-ylpiperazin-1-yl)sulfonyl]methyl}-3-(trimethylsilyl)prop-2-yn-1-yl]formamide;
1-({[4-(4-fluorophenyl)-1-piperazinyl]sulfonyl}methyl)-3-phenyl-2-propynyl(hydroxy)formamide;
1-[({4-[4-(benzyloxy)phenyl]-1-piperazinyl}sulfonyl)methyl]-2-octynyl(hydroxy)formamide;
1-({[4-(4-fluorophenyl)-1-piperazinyl]sulfonyl}methyl)-4-phenyl-2-butynyl(hydroxy)formamide;
1-({[4-(4-fluorophenyl)-1-piperazinyl]sulfonyl}methyl)-2-octynyl(hydroxy)formamide;
1-({[4-(4-fluorophenyl)-1-piperazinyl]sulfonyl}methyl)-3-(3-pyridinyl)-2-propynyl(hydroxy)formamide;
hydroxy[1-({[4-(4-methoxyphenyl)-1-piperazinyl]sulfonyl}methyl)-3-(3-pyridinyl)-2-propynyl]formamide;
hydroxy[3-(3-methoxyphenyl)-1-({[4-(4-methoxyphenyl)-1-piperazinyl]sulfonyl}methyl)-2-propynyl]formamide;
4-(diethylamino)-1-({[4-(4-methoxyphenyl)-1-piperazinyl]sulfonyl}methyl)-2-butynyl(hydroxy)formamide;
hydroxy(1-{[(4-pyridin-2-ylpiperazin-1-yl)sulfonyl]methyl}prop-2-yn-1-yl)formamide;
hydroxy(1-{[(4-pyridin-2-ylpiperazin-1-yl)sulfonyl]methyl}hex-2-yn-1-yl)formamide;
[1-({[4-(2-fluorophenyl)piperazin-1-yl]sulfonyl}methyl)oct-2-yn-1-yl]hydroxy formamide;
hydroxy(1-{[(4-pyridin-2-ylpiperazin-1-yl)sulfonyl]methyl}oct-2-yn-1-yl)formamide;
hydroxy{1-[({4-[4-(trifluoromethyl)phenyl]piperazin-1-yl}sulfonyl)methyl]-oct-2-yn-1-yl}formamide;
{1-({[4-(4-fluorophenyl)piperazin-1-yl]sulfonyl}methyl)-3-[3-(methyloxy)phenyl]prop-2-yn-1-yl}hydroxyformamide;
[1-({[4-(4-fluorophenyl)piperazin-1-yl]sulfonyl}methyl)hex-2-yn-1-yl]hydroxy formamide;
[1-({[4-(4-fluorophenyl)piperazin-1-yl]sulfonyl}methyl)-3-quinolin-3-ylprop-2-yn-1-yl]hydroxyformamide;
hydroxy(3-phenyl-1-{[(4-pyridin-2-ylpiperazin-1-yl)sulfonyl]methyl}prop-2-yn-1-yl)formamide;
hydroxy{3-phenyl-1-[({4-[4-(trifluoromethyl)phenyl]piperazin-1-yl}sulfonyl)methyl]prop-2-yn-1-yl}formamide;
hydroxy{1-[({4-[4-(methyloxy)phenyl]piperazin-1-yl}sulfonyl)methyl]-3-phenylprop-2-yn-1-yl}formamide;
{1-({[4-(4-fluorophenyl)piperazin-1-yl]sulfonyl}methyl)-3-[4-(1,2,4-oxadiazol-3-yl)phenyl]prop-2-yn-1-yl}hydroxyformamide;
hydroxy{1-[({4-[4-(methyloxy)phenyl]piperazin-1-yl}sulfonyl)methyl}oct-2-yn-1-yl}formamide;
(1-{[(4-biphenyl-4-ylpiperazin-1-yl)sulfonyl]methyl}-3-phenylprop-2-yn-1-yl)hydroxy formamide;
[1-({[4-(5-chloropyridin-2-yl)piperazin-1-yl]sulfonyl}methyl)oct-2-yn-1-yl]hydroxy formamide;

hydroxy(1-{[(4-pyrimidin-2-ylpiperazin-1-yl)sulfonyl]
methyl}oct-2-yn-1-yl)formamide;
hydroxy(1-{[(4-phenylpiperazin-1-yl)sulfonyl]
methyl}oct-2-yn-1-yl)formamide;
[1-({[4-(4-chlorophenyl)piperazin-1-yl]sulfonyl}methyl)
oct-2-yn-1-yl]hydroxy formamide;
hydroxy{1-[({4-[2-(methyloxy)phenyl]piperazin-1-
yl}sulfonyl)methyl]oct-2-yn-1-yl}formamide;
hydroxy{1-[({4-[3-(methyloxy)phenyl]piperazin-1-
yl}sulfonyl)methyl]oct-2-yn-1-yl}formamide;
[1-({[4-(4-fluorophenyl)piperazin-1-yl]sulfonyl}methyl)-
2,2-dimethyl-5-phenylpent-4-yn-1-yl]hydroxyformamide;
hydroxy{1-[({4-[5-(trifluoromethyl)pyridin-2-yl]piper-
azin-1-yl}sulfonyl)methyl]oct-2-yn-1-yl}formamide;
hydroxy{1-[({4-[4-(phenyloxy)phenyl]piperazin-1-
yl}sulfonyl)methyl]oct-2-yn-1-yl}formamide;
[1-({[4-(4-fluorophenyl)piperazin-1-yl]sulfonyl}methyl)
hept-2-yn-1-yl]hydroxy formamide;
{1-[({4-[4-(ethyloxy)phenyl]piperazin-1-yl}sulfonyl)me-
thyl]oct-2-yn-1-yl}hydroxy formamide;
[1-({[4-(5-bromopyridin-2-yl)piperazin-1-yl]
sulfonyl}methyl)oct-2-yn-1-yl]hydroxy formamide;
[1-({[4-(4-fluorophenyl)piperazin-1-yl]sulfonyl}methyl)-
4-morpholin-4-ylbut-2-yn-1-yl]hydroxyformamide;
[1-({[4-(3-chlorophenyl)piperazin-1-yl]sulfonyl}methyl)
oct-2-yn-1-yl]hydroxy formamide;
[1-({[4-(1,3-benzodioxol-5-yl)piperazin-1-yl]
sulfonyl}methyl)oct-2-yn-1-yl]hydroxy formamide;
hydroxy{1-[({4-[3-(methyloxy)phenyl]piperazin-1-
yl}sulfonyl)methyl]-3-phenylprop-2-yn-1-
yl}formamide;
[1-({[4-(4-chlorophenyl)piperazin-1-yl]
sulfonyl}methyl)-3-phenylprop-2-yn-1-yl]hydroxyformamide;
{1-[({4-[4-(ethyloxy)phenyl]piperazin-1-yl}sulfonyl)me-
thyl]-3-phenylprop-2-yn-1-yl}hydroxyformamide;
[1-({[4-(5-bromopyridin-2-yl)piperazin-1-yl]
sulfonyl}methyl)-2,2-dimethyl-5-phenylpent-4-yn-1-
yl]hydroxyformamide;
{2,2-dimethyl-5-phenyl-1-[({4-[4-(trifluoromethyl)phe-
nyl]piperazin-1-yl}sulfonyl)methyl]pent-4-yn-1-
yl}hydroxyformamide;
[1-({[4-(5-chloropyridin-2-yl)piperazin-1-yl]
sulfonyl}methyl)hex-2-yn-1-yl]hydroxy formamide;
{1-[({4-[4-(ethyloxy)phenyl]piperazin-1-yl}sulfonyl)me-
thyl]-2,2-dimethyl-5-phenylpent-4-yn-1-
yl}hydroxyformamide;
[1-({[4-(3,4-dimethoxyphenyl)piperazin-1-yl]
sulfonyl}methyl)oct-2-yn-1-yl]hydroxy formamide;
[1-({[(2R)-4-(4-fluorophenyl)-2-methylpiperazin-1-yl]
sulfonyl}methyl)oct-2-yn-1-yl]hydroxyformamide;
[1-({[4-(4-fluorophenyl)piperazin-1-yl]sulfonyl}methyl)-
2,2-dimethylpent-4-yn-1-yl]hydroxyformamide;
[1-({[4-(4-fluorophenyl)piperazin-1-yl]sulfonyl}methyl)-
4-pyrrolidin-1-ylbut-2-yn-1-yl]hydroxyformamide;
[1-({[4-(4-fluorophenyl)piperazin-1-yl]sulfonyl}methyl)-
2,2-dimethyl-6-morpholin-4-yl hex-4-yn-1-yl]hydroxyformamide; and
[1-({[4-(4-fluorophenyl)piperazin-1-yl]sulfonyl}methyl)-
2,2-dimethyl hept-4-yn-1-yl]hydroxyformamide;
and an enantiomer, diastereomer, or pharmaceutically
acceptable salt thereof.

15. A method for treating inflammation in a mammal comprising administering to the mammal an effective amount of a sulfonyl amino cyclic derivative according to claim 1.

16. A method for treating a mammal with a disease or disorder comprising administering to the mammal an effective amount of a sulfonyl amino cyclic derivative according to claim 1, wherein the disease or disorder is selected from rheumatoid arthritis and multiple sclerosis.

17. A pharmaceutical composition comprising a sulfonyl amino cyclic derivative according to claim 1 and a pharmaceutically acceptable carrier, diluent or excipient thereof.

18. A process for the manufacture of a compound according to claim 1, said process comprising the step of reacting a compound of Formula (II) with a formylating agent of Formula (FA):

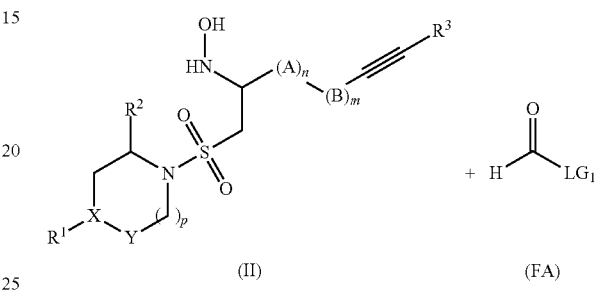

and thereby forming a compound according to claim 1;
wherein A, B, $R^1$, $R^2$, $R^3$, X, Y, m, n and p are as defined claim 1; and
$LG_1$ is a leaving group selected from the group consisting of —OH, —OAc, —OPiv, —OCH$_2$CN, —OCH$_2$CF$_3$, —OPh and —OPfp.

19. A compound according to the Formula:

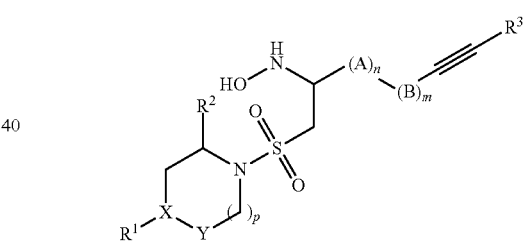

wherein:
A is $CR^4R^5$;
B is $CR^{4'}R^{5'}$;
$R^1$ is selected from aryl, heteroaryl, $C_3$-$C_8$-cycloalkyl and heterocycloalkyl;
$R^2$ is selected from H, $C_1$-$C_6$-alkyl, $C_2$-$C_6$-alkenyl and $C_2$-$C_6$-alkynyl;
$R^3$ is selected from H, —Si($C_1$-$C_6$-alkyl)$_3$, amino-$C_1$-$C_6$-alkyl, $C_1$-$C_6$-alkyl, aryl, heteroaryl, aryl-$C_1$-$C_6$-alkyl, heteroaryl-$C_1$-$C_6$-alkyl, $C_3$-$C_8$-cycloalkyl-$C_1$-$C_6$-alkyl, heterocycloalkyl-$C_1$-$C_6$-alkyl, $C_3$-$C_8$-cycloalkyl and heterocycloalkyl;
$R^4$, $R^5$, $R^{4'}$ and $R^{5'}$ are independently selected from H, halogen, $C_1$-$C_6$-alkyl, $C_2$-$C_6$-alkenyl and $C_2$-$C_6$-alkynyl;
X is N;
Y is CH$_2$;
the group —X—Y— is —N—CH$_2$—;
m is selected from 0, 1 and 2;
n is selected from 0 and 1; and
p is 1;

or an enantiomer, diastereomer, or a pharmaceutically acceptable salt thereof.

20. A compound selected from the group consisting of:
N-[3-(1,3-benzodioxol-5-yl)-1-({[4-(4-fluorophenyl)-1-piperazinyl]sulfonyl}methyl)-2-propynyl]hydroxylamine;
1-(4-fluorophenyl)-4-{[2-(hydroxyamino)-4-(trimethylsilyl)-3-butynyl]sulfonyl}piperazine;
1-{[2-(hydroxyamino)-4-(trimethylsilyl)-3-butynyl]sulfonyl}-4-(2-pyridinyl)piperazine;
1-(4-fluorophenyl)-4-{[2-(hydroxyamino)-4-phenyl-3-butynyl]sulfonyl}piperazine;
1-[4-(benzyloxy)phenyl]-4-{[2-(hydroxyamino)-3-nonynyl]sulfonyl}piperazine;
1-(4-fluorophenyl)-4-{[2-(hydroxyamino)-5-phenyl-3-pentynyl]sulfonyl}piperazine;
1-(4-fluorophenyl)-4-{[2-(hydroxyamino)-3-nonynyl]sulfonyl}piperazine;
1-(4-fluorophenyl)-4-{[2-(hydroxyamino)-4-(3-pyridinyl)-3-butynyl]sulfonyl}piperazine;
1-{[2-(hydroxyamino)-4-(3-pyridinyl)-3-butynyl]sulfonyl}-4-(4-methoxyphenyl)piperazine;
1-{[2-(hydroxyamino)-4-(3-methoxyphenyl)-3-butynyl]sulfonyl}-4-(4-methoxyphenyl)piperazine;
N,N-diethyl-4-(hydroxyamino)-5-{[4-(4-methoxyphenyl)-1-piperazinyl]sulfonyl}-2-pentyn-1-amine;
1-{[2-(hydroxyamino)but-3-yn-1-yl]sulfonyl}-4-pyridin-2-ylpiperazine;
1-{[2-(hydroxyamino)hept-3-yn-1-yl]sulfonyl}-4-pyridin-2-ylpiperazine;
1-(2-fluorophenyl)-4-{[2-(hydroxyamino)non-3-yn-1-yl]sulfonyl}piperazine;
1-{[2-(hydroxyamino)non-3-yn-1-yl]sulfonyl}-4-pyridin-2-ylpiperazine;
1-{[2-(hydroxyamino)non-3-yn-1-yl]sulfonyl}-4-[4-(trifluoromethyl)phenyl]piperazine;
1-(4-fluorophenyl)-4-{[2-(hydroxyamino)-4-(3-methoxyphenyl)but-3-yn-1-yl]sulfonyl}piperazine;
1-(4-fluorophenyl)-4-{[2-(hydroxyamino)hept-3-yn-1-yl]sulfonyl}piperazine;
1-{[2-(hydroxyamino)-4-phenylbut-3-yn-1-yl]sulfonyl}-4-[4-(trifluoromethyl)phenyl]piperazine;
3-[4-{[4-(4-fluorophenyl)piperazin-1-yl]sulfonyl}-3-(hydroxyamino)but-1-yn-1-yl]quinoline;
1-{[2-(hydroxyamino)-4-phenylbut-3-yn-1-yl]sulfonyl}-4-pyridin-2-ylpiperazine;
1-{[2-(hydroxyamino)-4-phenylbut-3-yn-1-yl]sulfonyl}-4-(4-methoxyphenyl)piperazine;
1-(4-fluorophenyl)-4-({2-(hydroxyamino)-4-[4-(1,2,4-oxadiazol-3-yl)phenyl]but-3-yn-1-yl}sulfonyl)piperazine;
1-{[2-(hydroxyamino)non-3-yn-1-yl]sulfonyl}-4-(4-methoxyphenyl)piperazine;
1-biphenyl-4-yl-4-{[2-(hydroxyamino)-4-phenylbut-3-yn-1-yl]sulfonyl}piperazine;
1-(5-chloropyridin-2-yl)-4-{[2-(hydroxyamino)non-3-yn-1-yl]sulfonyl}piperazine;
2-(4-{[2-(hydroxyamino)non-3-yn-1-yl]sulfonyl}piperazin-1-yl)pyrimidine;
1-{[2-(hydroxyamino)non-3-yn-1-yl]sulfonyl}-4-phenylpiperazine;
1-(4-chlorophenyl)-4-{[2-(hydroxyamino)non-3-yn-1-yl]sulfonyl}piperazine;
1-{[2-(hydroxyamino)non-3-yn-1-yl]sulfonyl}-4-(2-methoxyphenyl)piperazine;
1-{[2-(hydroxyamino)non-3-yn-1-yl]sulfonyl}-4-(3-methoxyphenyl)piperazine;
1-(4-fluorophenyl)-4-{[2-(hydroxyamino)-3,3-dimethyl-6-phenylhex-5-yn-1-yl]sulfonyl}piperazine;
1-{[2-(hydroxyamino)non-3-yn-1-yl]sulfonyl}-4-[5-(trifluoromethyl)pyridin-2-yl]piperazine;
1-{[2-(hydroxyamino)non-3-yn-1-yl]sulfonyl}-4-(4-phenoxyphenyl)piperazine;
1-(4-fluorophenyl)-4-{[2-(hydroxyamino)oct-3-yn-1-yl]sulfonyl}piperazine;
1-(4-ethoxyphenyl)-4-{[2-(hydroxyamino)non-3-yn-1-yl]sulfonyl}piperazine;
1-(5-bromopyridin-2-yl)-4-{[2-(hydroxyamino)non-3-yn-1-yl]sulfonyl}piperazine;
4-[5-{[4-(4-fluorophenyl)piperazin-1-yl]sulfonyl}-4-(hydroxyamino)pent-2-yn-1-yl]morpholine;
1-(3-chlorophenyl)-4-{[2-(hydroxyamino)non-3-yn-1-yl]sulfonyl}piperazine;
1-(1,3-benzodioxol-5-yl)-4-{[2-(hydroxyamino)non-3-yn-1-yl]sulfonyl}piperazine;
1-{[2-(hydroxyamino)-4-phenylbut-3-yn-1-yl]sulfonyl}-4-(3-methoxyphenyl)piperazine;
1-(4-chlorophenyl)-4-{[2-(hydroxyamino)-4-phenylbut-3-yn-1-yl]sulfonyl}piperazine;
1-(4-ethoxyphenyl)-4-{[2-(hydroxyamino)-4-phenylbut-3-yn-1-yl]sulfonyl}piperazine;
1-(5-bromopyridin-2-yl)-4-{[2-(hydroxyamino)-3,3-dimethyl-6-phenylhex-5-yn-1-yl]sulfonyl}piperazine;
1-{[2-(hydroxyamino)-3,3-dimethyl-6-phenylhex-5-yn-1-yl]sulfonyl}-4-[4-(trifluoromethyl)phenyl]piperazine;
1-(5-chloropyridin-2-yl)-4-{[2-(hydroxyamino)hept-3-yn-1-yl]sulfonyl}piperazine;
1-(4-ethoxyphenyl)-4-{[2-(hydroxyamino)-3,3-dimethyl-6-phenylhex-5-yn-1-yl]sulfonyl}piperazine;
1-(3,4-dimethoxyphenyl)-4-{[2-(hydroxyamino)non-3-yn-1-yl]sulfonyl}piperazine;
(2R)-4-(4-fluorophenyl)-1-{[2-(hydroxyamino)non-3-yn-1-yl]sulfonyl}-2-methyl piperazine;
1-(4-fluorophenyl)-4-{[2-(hydroxyamino)-3,3-dimethylhex-5-yn-1-yl]sulfonyl}piperazine;
1-(4-fluorophenyl)-4-{[2-(hydroxyamino)-5-pyrrolidin-1-ylpent-3-yn-1-yl]sulfonyl}piperazine;
4-[7-{[4-(4-fluorophenyl)piperazin-1-yl]sulfonyl}-6-(hydroxyamino)-5,5-dimethyl hept-2-yn-1-yl]morpholine; and
1-(4-fluorophenyl)-4-{[2-(hydroxyamino)-3,3-dimethyloct-5-yn-1-yl]sulfonyl}piperazine;

and an enantiomer, diastereomer, or pharmaceutically acceptable salt thereof.

21. A process for the manufacture of a compound, according to claim 19, said process comprising the step of reacting a compound of Formula (III) with an aqueous solution of hydroxylamine of Formula (HA):

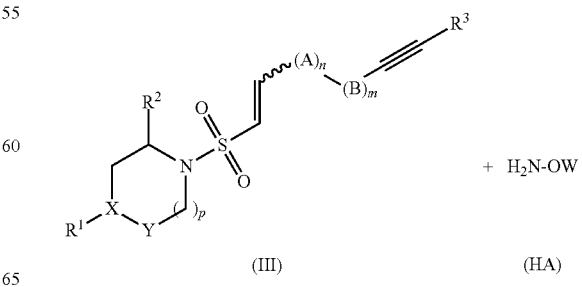

and thereby forming a compound according to claim 19;

wherein A, B, R¹, R², R³, X, Y, m, n and p are as in claim 19; and

W is selected from H, Benzyl, TMS, TBDMS and THP.

22. A compound according to the Formula:

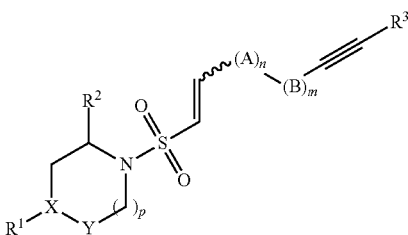

wherein:

A is $CR^4R^5$;

B is $CR^{4'}R^{5'}$;

$R^1$ is selected from aryl, heteroaryl, $C_3$-$C_8$-cycloalkyl and heterocycloalkyl;

$R^2$ is selected from H, $C_1$-$C_6$-alkyl, $C_2$-$C_6$-alkenyl and $C_2$-$C_6$-alkynyl;

$R^3$ is selected from H, —Si($C_1$-$C_6$-alkyl)$_3$, amino-$C_1$-$C_6$-alkyl, $C_1$-$C_6$-alkyl, aryl, heteroaryl, aryl-$C_1$-$C_6$-alkyl, heteroaryl-$C_1$-$C_6$-alkyl, $C_3$-$C_8$-cycloalkyl-$C_1$-$C_6$-alkyl, heterocycloalkyl-$C_1$-$C_6$-alkyl, $C_3$-$C_8$-cycloalkyl and heterocycloalkyl;

$R^4$, $R^5$, $R^{4'}$ and $R^{5'}$ are independently selected from H, halogen, $C_1$-$C_6$-alkyl, $C_2$-$C_6$-alkenyl and $C_2$-$C_6$-alkynyl;

X is N;

Y is $CH_2$;

the group —X—Y— is —N—$CH_2$—;

m is selected from 0, 1 and 2;

n is selected from 0 and 1; and p is 1;

or an enantiomer, diastereomer, or a pharmaceutically acceptable salt thereof.

23. A compound selected from the group consisting of:

1-{[(1E)-4-(1,3-benzodioxol-5-yl)-1-buten-3-ynyl]sulfonyl}-4-(4-fluorophenyl)piperazine;

1-{[(1Z)-4-(1,3-benzodioxol-5-yl)-1-buten-3-ynyl]sulfonyl}-4-(4-fluorophenyl)piperazine;

1-(4-fluorophenyl)-4-{[(1E)-4-(trimethylsilyl)-1-buten-3-ynyl]sulfonyl}piperazine;

1-(4-fluorophenyl)-4-{[(1Z)-4-(trimethylsilyl)-1-buten-3-ynyl]sulfonyl}piperazine;

1-(2-pyridinyl)-4-{[(1E)-4-(trimethylsilyl)-1-buten-3-ynyl]sulfonyl}piperazine;

1-(2-pyridinyl)-4-{[(1Z)-4-(trimethylsilyl)-1-buten-3-ynyl]sulfonyl}piperazine;

1-(4-fluorophenyl)-4-{[(1E)-4-phenyl-1-buten-3-ynyl]sulfonyl}piperazine;

1-(4-fluorophenyl)-4-{[(1Z)-4-phenyl-1-buten-3-ynyl]sulfonyl}piperazine;

benzyl 4-{4-[(1E)-1-nonen-3-ynylsulfonyl]-piperazinyl}phenyl ether;

benzyl 4-{4-[(1Z)-1-nonen-3-ynylsulfonyl]-1-piperazinyl}phenyl ether;

1-(4-fluorophenyl)-4-{[(1E)-5-phenyl-1-penten-3-ynyl]sulfonyl}piperazine;

1-(4-fluorophenyl)-4-{[(1Z)-5-phenyl-1-penten-3-ynyl]sulfonyl}piperazine;

1-(4-fluorophenyl)-4-[(1E)-1-nonen-3-ynylsulfonyl]piperazine;

1-(4-fluorophenyl)-4-[(1Z)-1-nonen-3-ynylsulfonyl]piperazine;

1-(4-fluorophenyl)-4-{[(1E)-4-(3-pyridinyl)-1-buten-3-ynyl]sulfonyl}piperazine;

1-(4-fluorophenyl)-4-{[(1Z)-4-(3-pyridinyl)-1-buten-3-ynyl]sulfonyl}piperazine;

1-(4-methoxyphenyl)-4-{[(1E)-4-(3-pyridinyl)-1-buten-3-ynyl]sulfonyl}piperazine;

1-(4-methoxyphenyl)-4-{[(1Z)-4-(3-pyridinyl)-1-buten-3-ynyl]sulfonyl}piperazine;

1-(4-methoxyphenyl)-4-{[(1E)-4-(3-methoxyphenyl)-1-buten-3-ynyl]sulfonyl}piperazine;

1-(4-methoxyphenyl)-4-{[(1Z)-4-(3-methoxyphenyl)-1-buten-3-ynyl]sulfonyl}piperazine;

N,N-diethyl-N-((4E)-5-{[4-(4-methoxyphenyl)-1-piperazinyl]sulfonyl}-4-penten-2-ynyl)amine;

N,N-diethyl-N-((4Z)-5-{[4-(4-methoxy phenyl)-1-piperazinyl]sulfonyl}-4-penten-2-ynyl)amine;

1-[(1E)-but-1-en-3-yn-1-ylsulfonyl]-4-pyridin-2-ylpiperazine;

1-[(1Z)-but-1-en-3-yn-1-ylsulfonyl]-4-pyridin-2-ylpiperazine;

1-[-hept-1-en-3-yn-1-ylsulfonyl]-4-pyridin-2-ylpiperazine;

1-(2-fluorophenyl)-4-[-non-1-en-3-yn-1-ylsulfonyl]piperazine;

1-[-non-1-en-3-yn-1-ylsulfonyl]-4-pyridin-2-ylpiperazine;

1-[-non-1-en-3-yn-1-ylsulfonyl]-4-[4-(trifluoromethyl)phenyl]piperazine;

1-(4-fluorophenyl)-4-{[-4-(3-methoxyphenyl)but-1-en-3-yn-1-yl]sulfonyl}piperazine;

1-(4-fluorophenyl)-4-[-hept-1-en-3-yn-1-ylsulfonyl]piperazine;

1-{[-4-phenylbut-1-en-3-yn-1-yl]sulfonyl}-4-[4-(trifluoromethyl)phenyl]piperazine;

3-((3E)-4-{[4-(4-fluorophenyl)piperazin-1-yl]sulfonyl}but-3-en-1-yn-1-yl)quinoline;

1-{[-4-phenylbut-1-en-3-yn-1-yl]sulfonyl}-4-pyridin-2-ylpiperazine;

1-(4-methoxyphenyl)-4-{[-4-phenylbut-1-en-3-yn-1-yl]sulfonyl}piperazine;

1-(4-fluorophenyl)-4-({-4-[4-(1,2,4-oxadiazol-3-yl)phenyl]but-1-en-3-yn-1-yl}sulfonyl)piperazine;

1-(4-methoxyphenyl)-4-[-non-1-en-3-yn-1-ylsulfonyl]piperazine;

1-biphenyl-4-yl-4-{[-4-phenylbut-1-en-3-yn-1-yl]sulfonyl}piperazine;

1-(5-chloropyridin-2-yl)-4-[-non-1-en-3-yn-1-ylsulfonyl]piperazine;

2-{4-[-non-1-en-3-yn-1-ylsulfonyl]piperazin-1-yl}pyrimidine;

1-[-non-1-en-3-yn-1-ylsulfonyl]-4-phenylpiperazine;

1-(4-chlorophenyl)-4-[-non-1-en-3-yn-1-ylsulfonyl]piperazine;

1-(2-methoxyphenyl)-4-[-non-1-en-3-yn-1-ylsulfonyl]piperazine;

1-(3-methoxyphenyl)-4-[-non-1-en-3-yn-1-ylsulfonyl]piperazine;

1-{[-3,3-dimethyl-6-phenylhex-1-en-5-yn-1-yl]sulfonyl}-4-(4-fluorophenyl)piperazine;

1-[-non-1-en-3-yn-1-ylsulfonyl]-4-[5-(trifluoromethyl)pyridin-2-yl]piperazine;

1-[-non-1-en-3-yn-1-ylsulfonyl]-4-(4-phenoxyphenyl)piperazine;

1-(4-fluorophenyl)-4-[-oct-1-en-3-yn-1-ylsulfonyl]piperazine;

1-(4-ethoxyphenyl)-4-[-non-1-en-3-yn-1-ylsulfonyl]piperazine;

1-(5-bromopyridin-2-yl)-4-[-non-1-en-3-yn-1-ylsulfonyl]piperazine;

4-(-5-{[4-(4-fluorophenyl)piperazin-1-yl]sulfonyl}pent-4-en-2-yn-1-yl)morpholine;

1-(3-chlorophenyl)-4-[-non-1-en-3-yn-1-ylsulfonyl]piperazine;

1-(1,3-benzodioxol-5-yl)-4-[-non-1-en-3-yn-1-ylsulfonyl]piperazine;

1-(3-methoxyphenyl)-4-{[-4-phenylbut-1-en-3-yn-1-yl]sulfonyl}piperazine;

1-(4-chlorophenyl)-4-{[-4-phenylbut-1-en-3-yn-1-yl]sulfonyl}piperazine;

1-(4-ethoxyphenyl)-4-{[-4-phenylbut-1-en-3-yn-1-yl]sulfonyl}piperazine;

1-(5-bromopyridin-2-yl)-4-{[-3,3-dimethyl-6-phenylhex-1-en-5-yn-1-yl]sulfonyl}piperazine;

1-{[-3,3-dimethyl-6-phenylhex-1-en-5-yn-1-yl]sulfonyl}-4-[4-(trifluoromethyl)phenyl]piperazine;

1-(5-chloropyridin-2-yl)-4-[-hept-1-en-3-yn-1-ylsulfonyl]piperazine;

1-{[-3,3-dimethyl-6-phenylhex-1-en-5-yn-1-yl]sulfonyl}-4-(4-ethoxyphenyl)piperazine;

1-(3,4-dimethoxyphenyl)-4-[-non-1-en-3-yn-1-ylsulfonyl]piperazine;

(2R)-4-(4-fluorophenyl)-2-methyl-1-[-non-1-en-3-yn-1-ylsulfonyl]piperazine;

1-{[-3,3-dimethylhex-1-en-5-yn-1-yl]sulfonyl}-4-(4-fluorophenyl)piperazine;

1-(4-fluorophenyl)-4-{[-5-pyrrolidin-1-ylpent-1-en-3-yn-1-yl]sulfonyl}piperazine;

4-(7-{[4-(4-fluorophenyl)piperazin-1-yl]sulfonyl}-5,5-dimethylhept-6-en-2-yn-1-yl)morpholine; and 1-{[-3,3-dimethyloct-1-en-5-yn-1-yl]sulfonyl}-4-(4-fluorophenyl)piperazine;

and an enantiomer, diastereomer, or pharmaceutically acceptable salt thereof.

24. A method for treating a mammal with a disease or disorder comprising administering to the mammal an effective amount of a sulfonyl amino cyclic derivative according to claim 1, wherein the disease or disorder is Chronic Obstructive Pulmonary Disease.

* * * * *

UNITED STATES PATENT AND TRADEMARK OFFICE
CERTIFICATE OF CORRECTION

PATENT NO.       : 7,973,039 B2  
APPLICATION NO.  : 11/793474  
DATED            : July 5, 2011  
INVENTOR(S)      : Dominique Swinnen et al.

Page 1 of 1

It is certified that error appears in the above-identified patent and that said Letters Patent is hereby corrected as shown below:

In Column 107, Claim 23, line 59, before "piperazinyl}phenyl" insert -- 1- --.

Signed and Sealed this
Twenty-seventh Day of September, 2011

David J. Kappos
*Director of the United States Patent and Trademark Office*